(12) United States Patent
Pringle et al.

(10) Patent No.: US 11,031,222 B2
(45) Date of Patent: Jun. 8, 2021

(54) CHEMICALLY GUIDED AMBIENT IONISATION MASS SPECTROMETRY

(71) Applicant: Micromass UK Limited, Wilmslow (GB)

(72) Inventors: Steven Derek Pringle, Darwen (GB); Emrys Jones, Manchester (GB); Michael Raymond Morris, Glossop (GB); Julia Balog, Solymar (HU); James Ian Langridge, Sale (GB); Keith Richardson, High Peak (GB); Daniel Simon, Morichida (HU); Lajos Godorhazy, Erd (HU); Daniel Szalay, Budapest (HU); Zoltan Takats, Cambridge (GB)

(73) Assignee: Micromass UK Limited, Wilmslow (GB)

(*) Notice: Subject to any disclaimer, the term of this patent is extended or adjusted under 35 U.S.C. 154(b) by 298 days.

(21) Appl. No.: 15/556,064

(22) PCT Filed: Mar. 7, 2016

(86) PCT No.: PCT/GB2016/050608
§ 371 (c)(1),
(2) Date: Sep. 6, 2017

(87) PCT Pub. No.: WO2016/142679
PCT Pub. Date: Sep. 15, 2016

(65) Prior Publication Data
US 2018/0042583 A1 Feb. 15, 2018

(30) Foreign Application Priority Data

Mar. 6, 2015 (GB) .................................. 1503863.1
Mar. 6, 2015 (GB) .................................. 1503864.9
(Continued)

(51) Int. Cl.
*G01N 33/92* (2006.01)
*G01N 3/00* (2006.01)
(Continued)

(52) U.S. Cl.
CPC ............ *H01J 49/049* (2013.01); *A61B 1/041* (2013.01); *A61B 1/2736* (2013.01);
(Continued)

(58) Field of Classification Search
CPC ......... H01J 49/049; A61B 90/13; G01N 3/00; G01N 9/00
See application file for complete search history.

(56) References Cited

U.S. PATENT DOCUMENTS 525,799 A 9/1894 Rymes
3,479,545 A 11/1969 Wilson
(Continued)

FOREIGN PATENT DOCUMENTS

CA 2882003 A1 2/2014
CN 101170043 A 4/2008
(Continued)

OTHER PUBLICATIONS

Summons to Attend Oral Proceedings Pursuant to Rule 115(1) EPC of EP Application No. 12726643.5, dated Apr. 20, 2018, 7 pages.
(Continued)

*Primary Examiner* — Brian J. Sines
(74) *Attorney, Agent, or Firm* — Kacvinsky Daisak Bluni PLLC

(57) ABSTRACT

A method is disclosed comprising obtaining or acquiring chemical or other non-mass spectrometric data from one or more regions of a target using a chemical sensor. The chemical or other non-mass spectrometric data may be used to determine one or more regions of interest of the target. An ambient ionisation ion source may then be used to generate
(Continued)

aerosol, smoke or vapour from one or more regions of the target.

12 Claims, 14 Drawing Sheets

(30) Foreign Application Priority Data

| | | | |
|---|---|---|---|
| Mar. 6, 2015 | (GB) | ................................. | 1503867.2 |
| Mar. 6, 2015 | (GB) | ................................. | 1503876.3 |
| Mar. 6, 2015 | (GB) | ................................. | 1503877.1 |
| Mar. 6, 2015 | (GB) | ................................. | 1503878.9 |
| Mar. 6, 2015 | (GB) | ................................. | 1503879.7 |
| Sep. 9, 2015 | (GB) | ................................. | 1516003.9 |
| Oct. 16, 2015 | (GB) | ................................. | 1518369.2 |

(51) Int. Cl.

| | |
|---|---|
| *G01N 9/00* | (2006.01) |
| *A61B 90/13* | (2016.01) |
| *H01J 49/04* | (2006.01) |
| *A61B 10/02* | (2006.01) |
| *A61B 17/32* | (2006.01) |
| *A61B 18/00* | (2006.01) |
| *A61B 18/14* | (2006.01) |
| *A61B 18/20* | (2006.01) |
| *G01N 33/68* | (2006.01) |
| *H01J 49/00* | (2006.01) |
| *H01J 49/06* | (2006.01) |
| *H01J 49/16* | (2006.01) |
| *A61B 1/04* | (2006.01) |
| *A61B 1/273* | (2006.01) |
| *A61B 5/00* | (2006.01) |
| *A61B 5/01* | (2006.01) |
| *A61B 5/0507* | (2021.01) |
| *A61B 5/055* | (2006.01) |
| *A61B 6/03* | (2006.01) |
| *A61B 8/13* | (2006.01) |
| *A61B 10/00* | (2006.01) |
| *A61B 17/00* | (2006.01) |
| *A61B 18/04* | (2006.01) |
| *A61B 18/18* | (2006.01) |
| *A61F 13/38* | (2006.01) |
| *C12Q 1/02* | (2006.01) |
| *C12Q 1/04* | (2006.01) |
| *C12Q 1/18* | (2006.01) |
| *C12Q 1/24* | (2006.01) |
| *G01N 1/22* | (2006.01) |
| *G01N 27/622* | (2021.01) |
| *G01N 27/624* | (2021.01) |
| *G01N 30/72* | (2006.01) |
| *G01N 33/487* | (2006.01) |
| *H01J 49/02* | (2006.01) |
| *H01J 49/10* | (2006.01) |
| *H01J 49/14* | (2006.01) |
| *H01J 49/24* | (2006.01) |
| *H01J 49/26* | (2006.01) |
| *G16B 20/00* | (2019.01) |
| *G16H 10/40* | (2018.01) |
| *G16H 15/00* | (2018.01) |
| *G16H 50/20* | (2018.01) |
| *A61B 1/00* | (2006.01) |
| *A61B 1/31* | (2006.01) |
| *A61B 5/145* | (2006.01) |
| *G06F 19/00* | (2018.01) |

(52) U.S. Cl.
CPC .......... *A61B 5/0066* (2013.01); *A61B 5/0075* (2013.01); *A61B 5/015* (2013.01); *A61B 5/055* (2013.01); *A61B 5/0507* (2013.01); *A61B 6/032* (2013.01); *A61B 6/037* (2013.01); *A61B 8/13* (2013.01); *A61B 10/00* (2013.01); *A61B 10/0041* (2013.01); *A61B 10/0233* (2013.01); *A61B 10/0283* (2013.01); *A61B 17/00* (2013.01); *A61B 17/320068* (2013.01); *A61B 18/00* (2013.01); *A61B 18/04* (2013.01); *A61B 18/042* (2013.01); *A61B 18/14* (2013.01); *A61B 18/1445* (2013.01); *A61B 18/1815* (2013.01); *A61B 18/20* (2013.01); *A61B 90/13* (2016.02); *A61F 13/38* (2013.01); *C12Q 1/025* (2013.01); *C12Q 1/04* (2013.01); *C12Q 1/18* (2013.01); *C12Q 1/24* (2013.01); *G01N 1/2202* (2013.01); *G01N 3/00* (2013.01); *G01N 9/00* (2013.01); *G01N 27/622* (2013.01); *G01N 27/624* (2013.01); *G01N 30/724* (2013.01); *G01N 33/487* (2013.01); *G01N 33/6848* (2013.01); *G01N 33/6851* (2013.01); *G01N 33/92* (2013.01); *H01J 49/0004* (2013.01); *H01J 49/0027* (2013.01); *H01J 49/0031* (2013.01); *H01J 49/0036* (2013.01); *H01J 49/025* (2013.01); *H01J 49/044* (2013.01); *H01J 49/0404* (2013.01); *H01J 49/0422* (2013.01); *H01J 49/0445* (2013.01); *H01J 49/0459* (2013.01); *H01J 49/0463* (2013.01); *H01J 49/0468* (2013.01); *H01J 49/061* (2013.01); *H01J 49/068* (2013.01); *H01J 49/10* (2013.01); *H01J 49/14* (2013.01); *H01J 49/16* (2013.01); *H01J 49/164* (2013.01); *H01J 49/24* (2013.01); *H01J 49/26* (2013.01); *A61B 1/00013* (2013.01); *A61B 1/31* (2013.01); *A61B 5/14542* (2013.01); *A61B 2010/0083* (2013.01); *A61B 2017/320069* (2017.08); *A61B 2018/00577* (2013.01); *A61B 2018/00589* (2013.01); *A61B 2018/00994* (2013.01); *A61B 2218/002* (2013.01); *A61B 2218/008* (2013.01); *G01N 33/48735* (2013.01); *G01N 2001/2223* (2013.01); *G01N 2333/195* (2013.01); *G01N 2405/00* (2013.01); *G01N 2405/04* (2013.01); *G01N 2405/08* (2013.01); *G01N 2570/00* (2013.01); *G01N 2800/26* (2013.01); *G06F 19/324* (2013.01); *G06F 19/3481* (2013.01); *G16B 20/00* (2019.02); *G16H 10/40* (2018.01); *G16H 15/00* (2018.01); *G16H 50/20* (2018.01)

(56) References Cited

U.S. PATENT DOCUMENTS

| | | |
|---|---|---|
| 3,770,954 A | 11/1973 | Davis |
| 4,408,125 A | 10/1983 | Meuzelaar |
| H000414 H | 1/1988 | Young et al. |
| 4,835,383 A | 5/1989 | Mahoney et al. |
| 4,845,367 A | 7/1989 | Amirav et al. |
| 4,883,958 A | 11/1989 | Vestal |
| 4,935,624 A | 6/1990 | Henion et al. |
| 5,033,541 A | 7/1991 | O'Silva |
| 5,053,343 A | 10/1991 | Vora et al. |
| 5,257,991 A | 11/1993 | Fletcher et al. |
| 5,308,977 A | 5/1994 | Oishi et al. |
| 5,374,755 A | 12/1994 | Neue et al. |
| 5,454,274 A | 10/1995 | Zhu |
| 5,509,916 A | 4/1996 | Taylor |

(56) References Cited

U.S. PATENT DOCUMENTS

| | | |
|---|---|---|
| 5,559,326 A | 9/1996 | Goodley et al. |
| 5,696,352 A | 12/1997 | Kourimsky |
| 5,800,597 A | 9/1998 | Perrotta et al. |
| 5,828,062 A | 10/1998 | Jarrell et al. |
| 5,830,214 A | 11/1998 | Flom et al. |
| 5,836,909 A | 11/1998 | Cosmescu |
| 5,969,352 A | 10/1999 | French et al. |
| 5,989,015 A | 11/1999 | Guerin et al. |
| 6,032,673 A | 3/2000 | Savage et al. |
| 6,333,632 B1 | 12/2001 | Yang et al. |
| 6,348,688 B1 | 2/2002 | Vestal |
| 6,825,464 B2 | 11/2004 | De La Mora |
| 6,998,622 B1 | 2/2006 | Wang et al. |
| 7,238,936 B2 | 7/2007 | Okamura et al. |
| 7,247,845 B1 | 7/2007 | Gebhardt et al. |
| 7,329,253 B2 | 2/2008 | Brounstein et al. |
| 7,335,897 B2 | 2/2008 | Takats et al. |
| 7,365,309 B2 | 4/2008 | Denny et al. |
| 7,517,348 B2 | 4/2009 | Vetter et al. |
| 7,564,028 B2 | 7/2009 | Vestal |
| 7,718,958 B2 | 5/2010 | Shiea et al. |
| 7,828,948 B1 | 11/2010 | Hatch et al. |
| 7,947,039 B2 | 5/2011 | Sartor |
| 7,960,711 B1 | 6/2011 | Sheehan et al. |
| 8,156,151 B2 | 4/2012 | Sidman |
| 8,193,487 B2 | 6/2012 | Briglin et al. |
| 8,232,520 B2 | 7/2012 | Cristoni |
| 8,253,098 B2 | 8/2012 | Hiraoka et al. |
| 8,286,260 B2 | 10/2012 | Vertes et al. |
| 8,314,382 B2 | 11/2012 | Takats |
| 8,334,504 B2 | 12/2012 | Finlay et al. |
| 8,431,409 B1 | 4/2013 | Meinhart et al. |
| 8,448,493 B2 | 5/2013 | McIntyre et al. |
| 8,481,922 B2 | 7/2013 | Musselman |
| 8,778,695 B2 | 7/2014 | Caprioli |
| 8,803,085 B2 | 8/2014 | Ouyang et al. |
| 8,834,462 B2 | 9/2014 | Johnson et al. |
| 8,970,840 B2 | 3/2015 | Kulkarni et al. |
| 9,046,448 B2 | 6/2015 | Takats |
| 9,053,914 B2 | 6/2015 | Pringle et al. |
| 9,082,603 B2 | 7/2015 | Bajic |
| 9,120,083 B2 | 9/2015 | Wyndham et al. |
| 9,255,907 B2 | 2/2016 | Heanue et al. |
| 9,281,174 B2 | 3/2016 | Takats |
| 9,287,100 B2 | 3/2016 | Szalay et al. |
| 9,709,529 B2 | 7/2017 | Takats |
| 9,731,219 B2 | 8/2017 | Wang et al. |
| 9,947,524 B2 | 4/2018 | Pringle |
| 10,186,626 B2 | 1/2019 | Song et al. |
| 2002/0008871 A1 | 1/2002 | Poustka et al. |
| 2002/0070338 A1 | 6/2002 | Loboda |
| 2002/0076824 A1 | 6/2002 | Haglund et al. |
| 2003/0001084 A1 | 1/2003 | Bateman et al. |
| 2003/0008404 A1 | 1/2003 | Tomita et al. |
| 2003/0015657 A1 | 1/2003 | Takada et al. |
| 2003/0042412 A1 | 3/2003 | Park |
| 2003/0080278 A1 | 5/2003 | Okada et al. |
| 2003/0119193 A1 | 6/2003 | Hess et al. |
| 2003/0135222 A1 | 7/2003 | Baska |
| 2003/0136918 A1 | 7/2003 | Hartley |
| 2003/0193023 A1 | 10/2003 | Marsh |
| 2004/0007673 A1 | 1/2004 | Coon et al. |
| 2004/0079881 A1 | 4/2004 | Fischer et al. |
| 2004/0124352 A1 | 7/2004 | Kashima et al. |
| 2004/0197899 A1 | 10/2004 | Gomez et al. |
| 2004/0217274 A1* | 11/2004 | Bai ................. H01J 49/164 250/282 |
| 2004/0235395 A1 | 11/2004 | Hashish et al. |
| 2005/0017091 A1 | 1/2005 | Olsen et al. |
| 2005/0032471 A1 | 2/2005 | Pfarr et al. |
| 2005/0061779 A1 | 3/2005 | Blumenfeld et al. |
| 2005/0067565 A1 | 3/2005 | Takada et al. |
| 2005/0072916 A1 | 4/2005 | Park |
| 2005/0074361 A1 | 4/2005 | Tanoshima et al. |
| 2005/0077644 A1 | 4/2005 | Bryan et al. |
| 2005/0124986 A1 | 6/2005 | Brounstein et al. |
| 2005/0138861 A1 | 6/2005 | O'Connor |
| 2005/0154490 A1 | 7/2005 | Blaine et al. |
| 2005/0159765 A1 | 7/2005 | Moutafis et al. |
| 2005/0178962 A1 | 8/2005 | Guevremont et al. |
| 2005/0178975 A1 | 8/2005 | Glukhoy |
| 2005/0230634 A1 | 10/2005 | Bajic et al. |
| 2005/0230635 A1 | 10/2005 | Takats et al. |
| 2005/0258358 A1 | 11/2005 | Thakur |
| 2005/0269518 A1 | 12/2005 | Bajic et al. |
| 2005/0274885 A1 | 12/2005 | Brown et al. |
| 2006/0035570 A1 | 2/2006 | Chisum et al. |
| 2006/0054806 A1 | 3/2006 | Yamada et al. |
| 2006/0091308 A1 | 5/2006 | Boyle et al. |
| 2006/0097084 A1 | 5/2006 | Gromer et al. |
| 2006/0108539 A1 | 5/2006 | Franzen |
| 2006/0113463 A1 | 6/2006 | Rossier et al. |
| 2006/0122593 A1 | 6/2006 | Jun |
| 2006/0138321 A1 | 6/2006 | Ahem et al. |
| 2006/0145089 A1 | 7/2006 | Cristoni et al. |
| 2006/0186334 A1 | 8/2006 | Jolliffe et al. |
| 2006/0250138 A1 | 11/2006 | Sparkman et al. |
| 2006/0255264 A1 | 11/2006 | Belford |
| 2007/0023631 A1 | 2/2007 | Takats et al. |
| 2007/0023677 A1 | 2/2007 | Perkins et al. |
| 2007/0094389 A1 | 4/2007 | Nussey et al. |
| 2007/0114388 A1 | 5/2007 | Ogawa et al. |
| 2007/0114394 A1 | 5/2007 | Combs et al. |
| 2007/0114437 A1 | 5/2007 | Kovtoun |
| 2007/0176113 A1 | 8/2007 | Shiea et al. |
| 2008/0001081 A1 | 1/2008 | Jindai et al. |
| 2008/0015278 A1 | 1/2008 | Malik et al. |
| 2008/0042056 A1 | 2/2008 | Fischer et al. |
| 2008/0067352 A1 | 3/2008 | Wang |
| 2008/0073503 A1 | 3/2008 | Wu |
| 2008/0073512 A1 | 3/2008 | Siuzdak et al. |
| 2008/0149822 A1 | 6/2008 | Vertes et al. |
| 2008/0172075 A1 | 7/2008 | Ammann |
| 2008/0173809 A1 | 7/2008 | Wu |
| 2008/0234579 A1 | 9/2008 | Halevy-Politch et al. |
| 2008/0312651 A1 | 12/2008 | Pope et al. |
| 2009/0065714 A1 | 3/2009 | Keady |
| 2009/0082637 A1 | 3/2009 | Galperin |
| 2009/0126891 A1 | 5/2009 | Koivunen et al. |
| 2009/0159790 A1 | 6/2009 | Kostiainen et al. |
| 2009/0272893 A1 | 11/2009 | Hieftje et al. |
| 2009/0302211 A1 | 12/2009 | Takats |
| 2010/0012830 A1 | 1/2010 | Cristoni |
| 2010/0072359 A1 | 3/2010 | Briglin et al. |
| 2010/0078550 A1 | 4/2010 | Wiseman et al. |
| 2010/0101304 A1 | 4/2010 | McIntyre et al. |
| 2010/0176290 A1 | 7/2010 | Vidal-de-Miguel |
| 2010/0186524 A1 | 7/2010 | Ariessohn et al. |
| 2010/0229263 A1* | 9/2010 | Vertes ................. B82Y 20/00 850/9 |
| 2011/0036978 A1 | 2/2011 | Franzen |
| 2011/0049352 A1 | 3/2011 | Ding et al. |
| 2011/0059554 A1 | 3/2011 | Albers et al. |
| 2011/0066147 A1 | 3/2011 | He et al. |
| 2011/0087308 A1 | 4/2011 | Morgan et al. |
| 2011/0121173 A1 | 5/2011 | Koenig et al. |
| 2011/0295250 A1 | 12/2011 | Johnson et al. |
| 2012/0018628 A1 | 1/2012 | Wuijckhuijse et al. |
| 2012/0043460 A1 | 2/2012 | Wouters et al. |
| 2012/0048264 A1 | 3/2012 | Finlay et al. |
| 2012/0074306 A1 | 3/2012 | Jesse et al. |
| 2012/0079894 A1 | 4/2012 | Berkel et al. |
| 2012/0080592 A1 | 4/2012 | Wiseman et al. |
| 2012/0085649 A1 | 4/2012 | Sano et al. |
| 2012/0119079 A1 | 5/2012 | Ouyang et al. |
| 2012/0149009 A1 | 6/2012 | Levis et al. |
| 2012/0156712 A1* | 6/2012 | Takats ................. A61B 10/02 435/29 |
| 2012/0295276 A1 | 11/2012 | Cooks et al. |
| 2013/0123919 A1 | 5/2013 | Goldstein et al. |
| 2013/0178845 A1 | 7/2013 | Smith et al. |
| 2013/0181126 A1 | 7/2013 | Jong |
| 2013/0303846 A1 | 11/2013 | Cybulski et al. |
| 2014/0151547 A1 | 6/2014 | Bajic |

(56) References Cited

U.S. PATENT DOCUMENTS

| | | | |
|---|---|---|---|
| 2014/0268134 A1 | 9/2014 | O'Connor | |
| 2014/0276775 A1 | 9/2014 | Funk et al. | |
| 2014/0291506 A1 | 10/2014 | Tikhonski et al. | |
| 2014/0297201 A1 | 10/2014 | Knorr et al. | |
| 2014/0299577 A1 | 10/2014 | Chung et al. | |
| 2014/0326865 A1 | 11/2014 | Pringle et al. | |
| 2014/0353488 A1* | 12/2014 | Takats | H01J 49/0431 250/282 |
| 2014/0353489 A1 | 12/2014 | Szalay et al. | |
| 2015/0021469 A1 | 1/2015 | Bajic | |
| 2015/0048255 A1 | 2/2015 | Jarrell | |
| 2015/0087003 A1 | 3/2015 | Charles et al. | |
| 2015/0144782 A1 | 5/2015 | Fogwill et al. | |
| 2015/0192590 A1 | 7/2015 | Sodeoka et al. | |
| 2015/0201913 A1* | 7/2015 | Takats | A61B 10/02 600/562 |
| 2016/0002696 A1 | 1/2016 | Galiano | |
| 2016/0133450 A1 | 5/2016 | Green et al. | |
| 2016/0215322 A1* | 7/2016 | Goodlett | G01N 33/56961 |
| 2016/0247668 A1* | 8/2016 | Szalay | H01J 49/16 |
| 2016/0341712 A1 | 11/2016 | Agar | |
| 2016/0372313 A1* | 12/2016 | Brown | H01J 49/045 |
| 2017/0103880 A1* | 4/2017 | Syage | H01J 49/0495 |
| 2018/0136091 A1 | 5/2018 | Ryan et al. | |

FOREIGN PATENT DOCUMENTS

| | | |
|---|---|---|
| CN | 101223625 A | 7/2008 |
| CN | 101288146 A | 10/2008 |
| CN | 101413905 A | 4/2009 |
| CN | 101490524 A | 7/2009 |
| CN | 201266145 Y | 7/2009 |
| CN | 101657158 A | 2/2010 |
| CN | 101819179 A | 9/2010 |
| CN | 101871914 A | 10/2010 |
| CN | 102026709 A | 4/2011 |
| CN | 102121921 A | 7/2011 |
| CN | 102137618 A | 7/2011 |
| CN | 102164675 A | 8/2011 |
| CN | 102264404 A | 11/2011 |
| CN | 102367424 A | 3/2012 |
| CN | 102445544 A | 5/2012 |
| CN | 102483369 A | 5/2012 |
| CN | 102800553 A | 11/2012 |
| CN | 102879453 A | 1/2013 |
| CN | 102924993 A | 2/2013 |
| CN | 102928610 A | 2/2013 |
| CN | 103295873 A | 9/2013 |
| CN | 103335984 A | 10/2013 |
| CN | 103597574 A | 2/2014 |
| CN | 104254772 A | 12/2014 |
| CN | 104254901 A | 12/2014 |
| CN | 104582616 A | 4/2015 |
| EP | 0169469 A2 | 1/1986 |
| EP | 0437358 A2 | 7/1991 |
| EP | 1855306 A1 | 11/2007 |
| EP | 1730519 B1 | 7/2010 |
| EP | 3265817 A1 | 1/2018 |
| EP | 3266035 A1 | 1/2018 |
| EP | 3265818 B1 | 2/2020 |
| GB | 2425178 A | 10/2006 |
| GB | 2491486 A | 12/2012 |
| JP | S63243864 A | 10/1988 |
| JP | 03001435 A | 8/1991 |
| JP | H0785834 A | 3/1995 |
| JP | H07130325 A | 5/1995 |
| JP | 10302710 A | 4/1997 |
| JP | H10247472 A | 9/1998 |
| JP | H11164283 A | 3/1999 |
| JP | 2000097913 A | 4/2000 |
| JP | 2000180413 A | 6/2000 |
| JP | 2001183345 A | 7/2001 |
| JP | 2002170518 A | 6/2002 |
| JP | 2004264043 A | 6/2002 |
| JP | 2005205181 A | 8/2005 |
| JP | 2006329710 A | 12/2006 |
| JP | 200751934 A | 3/2007 |
| JP | 2007170870 A | 7/2007 |
| JP | 2007218916 A | 8/2007 |
| JP | 2010169454 A | 8/2010 |
| JP | 2014515831 A | 7/2014 |
| JP | 2015503109 A | 1/2015 |
| JP | 2015504160 A | 2/2015 |
| KR | 1020020013544 A | 4/2007 |
| KR | 1020100106336 | 10/2010 |
| WO | 9734534 A1 | 9/1997 |
| WO | 0160265 A1 | 8/2001 |
| WO | 2008148557 A2 | 12/2008 |
| WO | 2010075265 A2 | 7/2010 |
| WO | 2010136887 A1 | 12/2010 |
| WO | 2011114902 A1 | 9/2011 |
| WO | 20120143737 A1 | 10/2012 |
| WO | 2012164312 A2 | 12/2012 |
| WO | 2012174437 A1 | 12/2012 |
| WO | 2013098642 A2 | 7/2013 |
| WO | 2013098645 A2 | 7/2013 |
| WO | 2013102670 A1 | 7/2013 |
| WO | 2013/148162 | 10/2013 |
| WO | 2013148162 A1 | 10/2013 |
| WO | 2014106165 A | 7/2014 |
| WO | 2014128629 A1 | 8/2014 |
| WO | 2014140601 A1 | 9/2014 |
| WO | 2014142926 A1 | 9/2014 |
| WO | 2014202828 A1 | 12/2014 |
| WO | 2015004457 A1 | 1/2015 |
| WO | 2015132579 A1 | 9/2015 |
| WO | 2016046748 | 3/2016 |
| WO | 2016142674 A1 | 9/2016 |
| WO | 2016156615 | 10/2016 |

OTHER PUBLICATIONS

Chen et al., "Surface desorption atmospheric pressure chemical ionization mass spectrometry for direct ambient sample analysis without toxic chemical contamination", Journal of Mass Spectrometry, 42(8):1045-1056, Jan. 1, 2007.

Chen, H., et al: "Neutral desorption sampling coupled to extractive electrospray ionization mass spectrometry for rapid differentiation of biosamples by metabolomic fingerprinting", Journal of Mass Spectromety, vol. 42, No. 9, Sep. 1, 2007 pp. 1123-1135.

Hensman C., et al: "Chemical Composition of Smoke Produced by High-Frequency Electrosurgery in a Closed Gaseous Environment an in Vitro Study", Surgical Endoscopy, vol. 12, No. 8, Aug. 1, 1998 (Aug. 1, 1998), pp. 1017-1019.

Moot, A. et al: "Composition of Volatile Organic Compouds in Diathermy Plume as Detected by Selected Ion Flow Tube Mass Spectrometry", ANZ Journal of Surgery, vol. 77, No. 1-2, (Jan. 2007) pp. 20-23.

Strittmatter, N.: "Home—Miss Nicole Strittmatter" Retrieved from the Internet URL: http://www.imperial.ac.uklpeople/n.strittmatter12 [retrieved on May 19, 2016] the whole document.

Wehofsky, et al "Automated deconvolution and deisotoping of electrospray mass spectra" J. Mass Spectrom. 2002; 37: pp. 223-229.

Al Sahaf et al., "Chemical Composition of Smoke Produced by High-Frequency Electrosurgery", Irish Journal of Medical Science, vol. 176, No. 3, pp. 229-232, 2007.

Barrett et al., "Surgical Smoke: A Review of the Literature", Surgical Endoscopy, vol. 17, No. 6, pp. 979-987, 2003.

Down, "A DESI-Rable Ionization Revolutionizes Mass Spectrometry", Base Peak, 2005.

International Search Report and Written Opinion for International Application. No. PCT/IB2012/003009, dated Aug. 14, 2013, 17 pages.

PCT International Search Report and Written Opinion for International Appln. No. PCT/IB2010/001261, dated Sep. 21, 2010, 5 pages.

PCT International Search Report and Written Opinion for International Appln. No. PCT/IB2012/002995, dated Sep. 10, 2013, 3 pages.

(56) References Cited

OTHER PUBLICATIONS

Qiao et al., "Electrostatic-Spray Ionization Mass Spectrometry", Analytical Chemistry, vol. 84, No. 17, pp. 7422-7430, 2012.
Lee et al., "Thermally Assisted Electrospray Interface for Liquid Chromatography/Mass Spectrometry", Rapid Communications in Mass Spectrometry, vol. 6, pp. 727-733, 1992.
McEwen et al., "Analysis of Solids, Liquids, and Biological Tissues Using Solids Probe Introduction at Atmospheric Pressure on Commercial LC/MS Instruments", Anal. Chem., vol. 77, pp. 7826-7831, 2005.
Sakairi et al., "Characteristics of a Liquid Chromatograph/Atmospheric Pressure Ionization Mass Spectrometer", Anal. Chem., vol. 60, pp. 774-780, 1988.
Takats et al., "Characterization of DESI-FTICR Mass Spectrometry—From ECD to Accurate Mass Tissue Analysis", Journal of Mass Spectrometry, vol. 43, pp. 196-203, 2008.
Eagles, et al., "Fast Atom Bombardment Mass Spectrometry of Amine Mixtures", John Wiley & Sons, Ltd, 1988.
Slemr et al., Concentration Profiles of Diamines in Fresh and aerobically Stored Park and Beef, American Chemical Society, 1985.
Mulligan, Christopher C. et al., "Desorption electrospray ionization with a portable mass spectrometer: in situ analysis of ambient surfaces", Chemical Communications—Chemcom, No. 16, pp. 1709-1711, (Jan. 2006).
Van Berke!, "Thin-Layer Chromatography and El3ectrospray Mass Spectrometry Coupled Using a Surface Sampling probe". Anal. Chem. 2002.
Takats et al., "Mass Spectrometry Sampling Under Ambient Conditions with Desorption Electrospray Ionization", Science, vol. 306, 2004.
Tottszer et al., "Laser Heating Versus Resistive Heating in the Field-Desorption Mass Spectrometry of Organic Polymers", J. Phys. D: Appl. Phys., vol. 21, pp. 1713-1720, 1988.
Zhou, X., et al., "Development of miniature mass spectrometry systems for bioanalysis outside the conventional laboratories." Bioanalysis, 6 (11) 1497-1508 (2014).
Bolt, F., et al., "Automated High-Throughput Identification and Characterization of Clinically Important Bacteria and Fungi using Rapid Evaporative Ionization Mass Spectrometry," American Chemical Socieity, 88 9419-9426 (2016).
McJimpsey, E.L., et al., "Parameters Contributing to Efficient Ion Generation in Aerosol MALDI Mass Spectrometry," American Society for Mass Spectrometry pp. 1044-0305 (2007).
Mutters, N.T., et al., "Performance of Kiestra Total Laboratory Automation Combined with MS in Clinical Microbiology Practice," Annals of Laboratory Medicine 34: 111-117 (2014).
Longuespée, R., et al., Tissue Proteomics for the Next Decade? Towards a Molecular Dimension in Histology, OMICS A Journal of Integrative Biology 28(9): 539-552 (2014).
Lu, K., et al., "Arsenic Exposure Perturbs the Gut Microbiome and its Metabolic Profile in Mice: An Integrated Metagenomics and Metabolomics Analysis," Environmental Health Perspectives, 122(3): 284-291 (2014).
Suarez, S., et al., Ribosomal proteins as biomarkers for bacterial identification by mass spectrometry in the clinical microbiology laboratory, Journal of microbiological Methods, 94: 390-396 (2013).
Trimpin, S. et al., New Ionization Method for Analysis on Atmospheric Pressure Ionization Mass Spectrometers Requiring Only Vacuum and Matrix Assistance, Analytical Chemistry, 85:2005-2009 (2013).
Cha, S., Laser desorption/ionization mass spectrometry for direct profiling and imaging of small moledcules from raw biological materials, Doctoral Dissertation, Iowa State University (2008).
Asano et al., "Self-aspirating atmospheric pressure chemical ionization source for direct sampling of analytes on Surfaces in liquid solution", Rapid Communications in Mass Spectrometry 2005.
International Search Report and Written Opinion for application No. PCT/GB2017/051050, dated Jun. 27, 2017, 15 pages.

Gerbig, Stefanie et al, "Spatially resolved investigation of systemic and contact pesticides in plant material by desorption electrospray ionization mass spectrometry imagine", Analytical and Bioanalytical Chemistry, 407 (24):7379-7389 (2015).
Lesiak, A., et al.,"Rapid detection by direct analysis in real time-mass spectrometry (DART-MS) of psychoactive plant drugs of abuse: the case of *Mitragyna speciosa* aka "Kratom"", 242:210-218 (2014).
Bartels, B. et al., "Spatially resolved in vivo plant metabolomics by laser ablation-based mass spectrometry imaging (MSI) techniques: LDI-MSI and LAESI", Frontiers in Plant Science vol. 6 (2015).
Nielen, M et al., "Desorption electrospray ionization mass spectrometry in the analysis of chemical food contaminants in food", Trac Trends in Analytical Chemistry, 30(2):165-180 (2011).
Boughton, B. et al., "Mass spectrometry imaging for plant biology: a review", Phytochemistry Reviews, 15(3):445-488 (2015).
Schäfer, K.C., et al., "In Situ, Real-Time Identification of Biological Tissue by Ultraviolet and Infrared Laser Desorption Ionization Mass Spectrometry", Analytical Chemistry, 83(5):1632-1640, Mar. 1, 2011.
International Search Report and Written Opinion for International Application No. PCT/GB2016/052956, dated Jan. 26, 2017, 16 pages.
Hsu, et al., "Microscopy ambient ionization top-down mass spectrometry reveals developmental patterning", Proceedings of the National Academy of Sciences, vol. 110, No. 37, pp. 14855-14860, Aug. 22, 2013.
Na, et al., "Development of a Dielectric Barrier Discharge Ion Source for Ambient Mass Spectrometry", Journal of the American Society for Mass Spectrometry, Elsevier Science Inc, vol. 18, No. 10, pp. 1859-1862, Sep. 20, 2007.
Ellis, S. et al., "Surface Analysis of Lipids by Mass Spectrometry: More Than Just Imaging", Progress in Lipid Research Pergamon Press, vol. 52, No. 4, pp. 329-353 (Oct. 2013).
Dong, Y., et al., "Sample Preparation for Mass Spectrometry Imaging of Plant Tissues: A Review", Frontiers in Plant Science 7(60): 1-16 (2016).
Communication pursuant to Article 94(3) EPC, for application No. 16710788.7, dated Jun. 13, 2019, 9 pages.
Examination Report under Section 18(3), for application No. GB1714122.7, dated May 9, 2019, 6 pages.
Bagley, B.M., et al., "Evaluation of archival time on shotgun proteomics of formalin-fixed and paraffin-embedded tissues", Journal of Proteome Research 8(2):917-925, (2009).
Cho, YT., et al. "Differentiation of Virulence of Helicobacter Pyloriby Matrix-Assited Laser Desorption/Ionization Mass Spectrometry and Multivariate Analyses" Clinica Chimica ACTA, Elsevier BV, 424:123-130, May 26, 2013.
Agar, Nathalie et al., "*Development of Stereotactic Mass Spectrometry for Brain Tumor Surgery*", Biosis, Neurosurgery Online, vol. 68, No. 2, (2011).
Ahlf, Dorothy R. et al., "*Correlated Mass Spectrometry Imaging and Confocal Raman Microscopy for Studies of Three-Dimensional Cell Culture Sections*", Analyst, vol. 139, No. 18, pp. 4578 (2014).
Azimzadeh, Omid et al., "*Formalin-Fixed Paraffin-Embedded (FFPE) Proteome Analysis Using Gel-Free and Gel-Based Proteomics*", Journal of Proteome Research, vol. 9, No. 9, pp. 4710-4720 (2010).
Balgley, Brian M. et al., "*Evaluation of Archival Time on Shotgun Proteomics of Formalin-Fixed and Paraffin-Embedded Tissues*", Journal of Proteome Research, vol. 8, No. 2, pp. 917-925 (2009).
Balog, Julia et al., "*Identification of Biological Tissues by Rapid Evaporative Ionization Mass Spectrometry*", Analytical Chemistry, vol. 82, No. 17, pp. 7343-7350 (2010).
Balog, Julia et al., "*Supporting Information for Identification of Biological Tissues by Rapid Evaporative Ionization Mass Spectrometry*", pp. S1-S9, http://pubs.acs.org/doi/suppl/10.1021/ac101, (2013).
Balog, J. et al., "*Intraoperative Tissue Identification Using Rapid Evaporative Ionization Mass Spectrometry*", Science Translational Medicine, vol. 5, No. 194, pp. 194ra93 (2013).
Balog, J. et al., "*Supplementary Materials: Intraoperative Tissue Identification Using Rapid Evaporative Ionization Mass Spectrometry*", Science Translational Medicine, vol. 5, No. 194, pp. 194ra93 (2013).

(56) References Cited

OTHER PUBLICATIONS

Bean, Heather D. et al., "Bacterial Volatile Discovery Using Solid Phase Microextraction and Comprehensive Two-Dimensional Gas Chromatographytime-of-Flight Mass Spectrometry", Journal of Chromatography B, vol. 901, pp. 41-46 (2012).

Bellet, V. et al., "Proteomic Analysis of RCL2 Paraffin-Embedded Tissues", Journal of Cellular and Molecular Medicine, vol. 12, No. 5B, pp. 2027-2036 (2008).

Bocklitz, T.W. et al., "Deeper Understanding of Biological Tissue: Quantitative Correlation of MALDI-TOF and Ranum Imaging", Analytical Chemistry, vol. 85, No. 22, pp. 10829-10834 (2013).

Cole, Laura M. et al., "Mass Spectrometry Imaging for the Proteomic Study of Clinical Tissue", Proteomics-Clinical Applications, vol. 9, No. 3-4, pp. 335-341 (2015).

Crawshaw, Benjamin et al., "Gastrointestinal Surgery: Real-Time Tissue Identification During Surgery", Nature Review/ Gastroenterology & Hepatology Nature, vol. 10, No. 11. pp. 624-625.

Cselik, Z. et al., "Impact of Infrared Laser Light-Induced Ablation at Different Wavelengths on Bovine Intervertebral Disc Ex Vivo: Evaluation with Magnetic Resonance Imaging and Histology", Lasers in Surgery and Medicine, vol. 44, No. 5, pp. 406-412 (2012).

Davies, T.J. et al., "Volatile Products from Acetylcholine as Markers in the Rapid Urine Test Using Head-Space Gas-Liquid Chromatography B: Biomedical Sciences and Applications", Journal of Chromatography, vol. 307, pp. 11-21 (1984).

European Commission, "ISD Report Summary", http://cordis.europa.eu/result/rcn/163435_e, (2016).

Fahy, Eoin, et al., "Lipid Classification, Structures and Tools", Biochimica at Biophysica Acta (BBA)—Molecular and Cell Biology of Lipids, vol. 1811, No. 11, pp. 637-647 (2011).

Gerbig, Stefanie et al., "Analysis of Colorectal Adenocarcinoma Tissue by Desorption Electrospray Ionization Mass Spectrometric Imaging", Analytical and Bioanalytical Chemistry, vol. 403, No. 8, pp. 2315-2325 (2012).

Golf, Ottmar et al., "Rapid Evaporative Ionization Mass Spectrometry Imaging Platform for Direct Mapping from Bulk Tissue and Bacterial Growth Media", Analytical Chemistry, vol. 87, No. 5, pp. 2527-2534 (2015).

Golf, Ottmar et al., "XMS: Cross-Platform Normalization Method for Multimodal Mass Spectrometric Tissue Profiling", Journal of the American Society for Mass Spectrometry, vol. 26, No. 1, pp. 44-54 (2014).

Guenther, Sabine et al., "Electrospray Post-Ionization Mass Spectrometry of Electrosurgical Aerosols", Journal of the American Society for Mass Spectrometry, vol. 22, No. 11, pp. 2082-2089 (2011).

Gustafsson, Ove J.R. et al., "Proteomic Developments in the Analysis of Formalin-Fixed Tissue", Biochimica et Biophysica Acta, vol. 1854, No. 6, pp. 559-580.

Hobbs, S.K. et al., "Magnetic Resonance Image-Guided Proteomics of Human Glioblastoma Multiforme", Journal of Magnetic Resonance Imaging, vol. 18, pp. 530-536 (2003).

Hsu, Cheng-Chih et al., "Visualizing Life with Ambient Mass Spectrometry", Current Opinion in Biotechnology, vol. 31, pp. 24-34 (2015).

Jadoul, L. et al., "Matrix-Assisted Laser Desorption/Ionization Mass Spectrometry and Raman Spectroscopy: An Interesting Complementary Approach for Lipid Detection in Biological Tissues", European Journal of Lipid Science and Technology. vol. 116, No. 8, pp. 1080-1086 (2014).

Jain, M. et al., "Metabolite Profiling Identifies a Key Role for Glycine in Rapid Cancer Cell Proliferation", American Association for the Advancement of Science, vol. 336, No. 6084, pp. 1040-1044 (2012).

Jarmusch, Alan K et al., "Detection of Strep Throat Causing Bacterium Directly from Medical Swabs by Touch Spray-Mass Spectrometry", Analyst, vol. 139, No. 19, pp. 4785 (2014).

Jarmusch, Alan K. et al., "Supplemental Information Detection of Strep Throat Causing Bacterium Directly from Medical Swabs by Touch Spray-Mass Spectrometry", http://www.rsc.org/supdata/an/c4/c4an00959 (2016).

Lazova, Rossitza et al., "Imaging Mass Spectrometry-A New and Promising Method to Differentiate Spitz Nevi From Spitzoid Malignant Melanomas", American Journal of Dermatopathology, vol. 34, No. 1, pp. 82-90 (2012).

Li, Yan et al., "Aberrant Mucin5B Expression in Lung Adenocarcinomas Detected by iTRAQ Labeling Quantitative Proteomics and Immunohistochemistry", Clinical Proteomics, vol. 10, No. 1, pp. 15 (2013).

Lieuwe, D.J. et al., "Volatile Metabolites of Pathogens: A Systematic Review", PLoS Pathogens, vol. 9, No. 5, pp. 1003311.

Luge, S. et al., "Use of a Lower Power, High Frequency Stabilized Capacitive Plasma Combined with Graphite Furnace Vaporization for the Atomic Emission Spectrometric Analysis of Serum Samples", Analytical Chimica Acta, vol. 332, No. 2-3, pp. 193-199 (1996).

Mccullough, Bryan J. et al., "On-Line Reaction Monitoring by Extractive Electrospray Ionisation", Rapid Communications in Mass Spectrometry, vol. 25, No. 10, pp. 1445-1451 (2011).

Murray, Patrick R, "What Is New in Clinical Microbiology-Microbial Identification by MALDI-TOF Mass Spectrometry", Journal of Molecular Diagnostics, vol. 14, No. 5, pp. 419-423 (2012).

Nicholson, Jeremy K. et al., "Metabolic Phenotyping in Clinical and Surgical Environments", Nature, vol. 491, No. 7424 pp. 384-392 (2012).

Pirro, Valentina et al., "Direct Drug Analysis from Oral Fluid Using Medical Swab Touch Spray Mass Spectrometry", Analytica Chimica Acta, vol. 861, pp. 47-54.

Plata, N. et al., "Aerosols Sampling Using a New Cryogenic Instrument", Journal of Aerosol Science, vol. 37, No. 12, pp. 1871-1875 (2006).

Rodriguez-Rigueiro, Teresa et al., "A Novel Procedure for Protein Extraction from Formalin-Fixed Paraffin-Embedded Tissues", Proteomics, vol. 11, No. 12, pp. 2555-2559 (2011).

Schafer, Karl-Christian et al., "In Vivo, In Situ Tissue Analysis Using Rapid Evaporative Ionization Mass Spectrometry", Angewandte Chemie International, vol. 48, No. 44, pp. 8240-8242 (2009).

Shane, Ellis R. et al., "Surface Analysis of Lipids by Mass Spectrometry: More Than Just Imaging", Progress in Lipid Research Pergamon Press, vol. 52, No. 4, pp. 329-353.

Shoemaker, Robert H., "The NCI60 Human Tumour Cell Line Anticancer Drug Screen", (2013).

Strittmatter, N. et al., "Anaylsis of Intact Bacteria Using Rapid Evaporative Ionisation Mass Spectrometry", Chemical Communications, vol. 49, No. 55, pp. 6188 (2013).

Strittmatter, N. et al., "Characterization and Identification of Clinically Relevant Microorganisms Using Rapid Evaporative Ionization Mass Spectrometry", Analytical Chemistry, vol. 86, No. 13, pp. 6555-6562 (2014).

Strittmatter, N. et al., "Taxon-Specific Markers for the Qualitative and Quantitative Detection of Bacteria in Human Samples", http://www.msacl.org/2015_US_Long_Abstract.

Tait, Emma et al., "Identification of Volatile Organic Compounds Produced by Bacteria Using HS-SPME-GC-MS", Journal of Chromatographic Sci, pp. 1-11.

Uribe, D.O. et al., "Piezoelectric Self-Sensing System for Tactile Intraoperative Brain Tumor Delineation in Neurosurgery", Proceedings of the 31$^{st}$ Annual International Conference of the IEEE Engineering in Medicine and Biology Society: Engineering the Future of BioMedicine, pp. 737-740 (2009).

Vander Wilp, W. et al., "Lead in Micro-Samples of Whole Blood by Rhenium-Cup in-Torch Vaporization-Inductively Coupled Plasma-Atomic Emission Spectrometry (ITV-ICP-AES)", Fresenius' Journal of Analytical Chemistry, vol. 368, No. 7, pp. 734-736 (2000).

Vircks, Kyle E. et al., "Rapid Screening of Synthetic Cathinones as Trace Residues and in Authentic Seizures Using a Portable Mass Spectrometer Equipped with Desorption Electrospray Ionization", Rapid Communications in Mass Spectrometry, vol. 26, No. 23, pp. 2665-2672 (2012).

(56) References Cited

OTHER PUBLICATIONS

Jackson, S. N. et al. On-line laser desorption/ionization mass spectrometry of matrix-coated aerosols, Rapid Communications in Mass Spectrometry, vol. 18, pp. 2041-2045 (Year: 2004).
Kohler, M. et al. "Characterization of lipid extracts from brain tissue and tumors using Raman spectroscopy and mass spectrometry," Anal Bioana Chem, 393:1513-1520, Jan. 20, 2009.
Harry, K. H., et al. "Effect of protein coating of flocked swabs on the collection and release of clinically important bacteria", Indian Journal of Medical Microbiology, 32(3):301-303 (2014).
Blais, B. W., "Swab-Based Enzyme Immunoassay System for Detection of Meat Residues on Food Contact Surfaces as a Hygiene Monitoring Tool", Journal of Food Protection, 62(4):386-389 (1999).
Farhat, S. E., et al., "Efficacy of a Swab Transport System in Maintaining Viability of Neisseria gonorrhoeae and *Streptococcus pneumoniae*", Journal of Clinical Microbiology, 39(8):2958-2960 (2001).
Chen et al. "Desorption Electrospray Ionization Mass spectrometry for high-thoughput analysis of Pharamaceutical samples in the ambient environment" (Year: 2005).
Hachmoeller et al., "Element bioimaging of liver needle biopsy specimens from patients with Wilsons disease by laser ablation-inductively coupled plasma-mass spectrometry", Journal of Trace Elements in Medicine and Biology, 35:97-102, Feb. 10, 2016.
Guenther et al., "Spatially Resolved Metabolic Phenotyping of Breast Cancer by Desorption Electrospray Ionization Mass Spectrometry", Cancer Research, 75:1828-1837, Feb. 17, 2015.
Extended EP Search Report for EP Patent Application No. 19171058.1, dated Nov. 15, 2019.
Santagata, S., et al.,"Intraoperative mass spectrometry mapping of an onco-metabolite to guide brain tumor surgery", Proceedings of the National Academy of Sciences (PNAS), 111(30):11121-11126, Jun. 30, 2014.
Chipuk, J. E., et al., "Transmission Mode Desorption Electrospray Ionization" , Journal of the American Society for Mass Spectrometry, 19(11):1612-1620, Nov. 1, 2008.
Harry, E. L. et al., "Direct analysis of pharmaceutical formulations from non-bonded reversed-phase thin-layer chromatography plates by desorption electrospray ionisation ion mobility mass spectrometry", Rapid Communications in Mass Spectrometry, 23(17):2597-2604, Jul. 28, 2009.
Chen, H., et al., "What Can We Learn from Ambient Ionization Techniques", Journal of the American Society for Mass Spectrometry, 20:1947-1963, (2009).
Sankaranarayanan, G., et al., "Common Uses and Cited Complications of Energy in Surgery", Surg Endosc., 27:3056-3072, (2013).
Rau, H.G., et al., "The use of water-jet dissection in open and laparoscopic liver resection", HPB, 10: 275280, (2008).
Office Action for CN Patent Application No. 201680025801.0 dated Apr. 7, 2020.
Office Action for CN Patent Application No. 201680025801.0 dated Apr. 7, 2020 translation.
Adams, F., et al, "Inorganic Mass Spectrometry", copyright John Wiley Sons, Inc. pp. 174-180 (1988).
Vemury, S., and Pratsinis, S.E., "Charging and Coagulation During Flame Synthesis of Silica" Journal Aerosol Science 27(6):951-966 (1996).
Examination Report under Section 18(3), for application No. GB1715787.6, dated Jun. 1, 2020, 6 pages.
CNOA for application No. 201680026285.3 dated Jun. 12, 2020, 12 pages (translation and original doc).
Panpradist, N., et al., "Swab Sample Transfer for Point-Of-Care Diagnostics: Characterization of Swab types and Manual Agitation Methods", Plos One 9(9):1-11 (2014).
Partial European Search Report for EP20181905.9, dated Aug. 27, 2020, 14 pages.
Roddy, T., et al., "Imaging of Freeze-Fractured Cells with in Situ Fluorescence and Time-of-Flight Secondary Ion Mass Spectrometry", Analytical Chemistry 74(16):4011-4019(2002).

Petrotchenko, E.V., et al., "Combining Fluorescence Detection and Mass Spectrometric Analysis for Comprehensive and Quantitative Analysis of Redox-Sensitive Cysteines in Native Membrane Proteins", Analytical Chemistry 78(23):7959-7966 (2006).
Ablonczy, Z., et al., "The utilization of fluorescence to identify the components of lipofuscin by imaging mass spectrometry", Proteomics 14(7-8):936-944.
Enthaler, B., et al., "Improved sample preparation for MALDI-MSI of endogenous compounds in skin tissue sections and mapping of exogenous active compounds subsequent to ex-vivo skin penetration" Anal Bioanal Chem 402:1159-1167 (2012).
Extended EP search report for EP Application No. 20172634.6, dated Sep. 14, 2020, 8 pages.
CNOA for application No. CN201680025801.0 dated Oct. 12, 2020 original document and translation.
Adams, F., et al., "Inorganic Mass Spectrometry", (1993) Abstract.
Dong, Y.M.B.A., "Polymer Analysis Handbook", China Petromchemical Press (2004) 8 pages.
Search and Examination Report under Sections 17 and 18(3) for GB1715767.8, dated Nov. 26, 2020, 6 pages.
Waters DESI System Operator's Guide 715004701/Revision A, Waters Corporation, [online] Jan. 2015 [retrieved on Dec. 3, 2020]. Retrieved from Internet URL: https://www.waters.com/webassets/cms/support/docs/715004701ra.pdf. 141 pages.
Shin, Y-S., et al., "Desorption Electrospray Ionization-Mass Spectrometry of Proteins" Analytical Chemistry 79:3514:3518 (2007).
Office Action for Application No. GB1713964.3, dated Oct. 26, 2020, 3 pages.
Office Action for Application No. GB1715787.6, dated Oct. 26, 2020, 3 pages.
Chen, X., ed. "Liquid Chromatography-Mass Spectrometry—Chapter 8", in Principle and Application of Chromatographic Analysis Technology, Chinese People's Public Security University Press, (2014, Jan.) 6 pages.
Song, Y., et al., "Rapid ambient mass spetrometric profiling of intact, untreated bacteria using desoprtion electrospray ionization" ChemComm pp. 61-63 (2007).
Wiseman, J.M. And Li, J.B., "Eluction, Partial Separation, and Identification of Lipids Directly from Tissue Slices on Planar Chromatogrpahy Media by Desoprtion Electrospray Ionization Mass Spectrometry", Anal Chem 82:8866-8874 (2010).
Examination Report under Section 18(3) for Application No. GB2015580.0, dated Jan. 21, 2021, 4 pages.
Krouskop, T., et al., Ultrasonic Imaging, vol. 20, 1998, "Elastic moduli of breast and prostate tissues under compression" Ultrasonic Imaging 20:260-274 (1998).
Aberg, P., et al., "Skin Cancer Identification Using Multifrequency Electrical Impedance—A Potential Screening Tool", IEEE Transactions on Biomedical Engineering, 51(12): 2097-2102 (2004).
Rath, C.M., et al., "Molecular Analysis of Model Gut Microbiotas by Imaging Mass Spectrometry and Nanodesorption Electrospray Ionization Reveals Dietary Metabolite Tranformations" Analytical Chemistry 84(21):9259-9267 (2012).
Fenselau, C.C., "Rapid Characterization of Microorganisms by Mass Spectrometry—What Can Be Learned and How?" Journal of the American Society for Mass Spectrometry 24(8):1161-1166 (2013).
Uetrecht, C. et al., "Modern Biomolecular Mass Spectrometry and its Role in Studying Virus Structure, Dynamics and Assembly" Angewandte Chemie International Edition 50(36):8248-8262 (2011).
Forbes, T.P. et al., "Chemical imaging of artificial Fingerprints by desorption electro-flow focusing ionization mass spectrometry" Analyst 139(12):2982-2985 (2014).
Cornett, D. S., et al, "A Novel Histology-directed Strategy for MALDI-MS Tissue Profiling That Improves Throughput and Cellular Specificity in Human Breast Cancer", American Society for Biochemistry and Molecular Biology, pp. 1975-1983, Jul. 18, 2006.
Extended European Search Report for Application No. 20210062.4, dated Mar. 9, 2021, 13 pages.
Examination Report under Section 18(3) for Application No. GB1715750.4 dated Mar. 22, 2021, 5 pages.
Examination Report for GB Patent Application No. GB2015580.0, dated Mar. 12, 2021,4 pages.

(56) References Cited

OTHER PUBLICATIONS

Examination Report under Section 18(3) for Application No. GB1714165.6, dated Mar. 22, 2021, 6 pages.

* cited by examiner

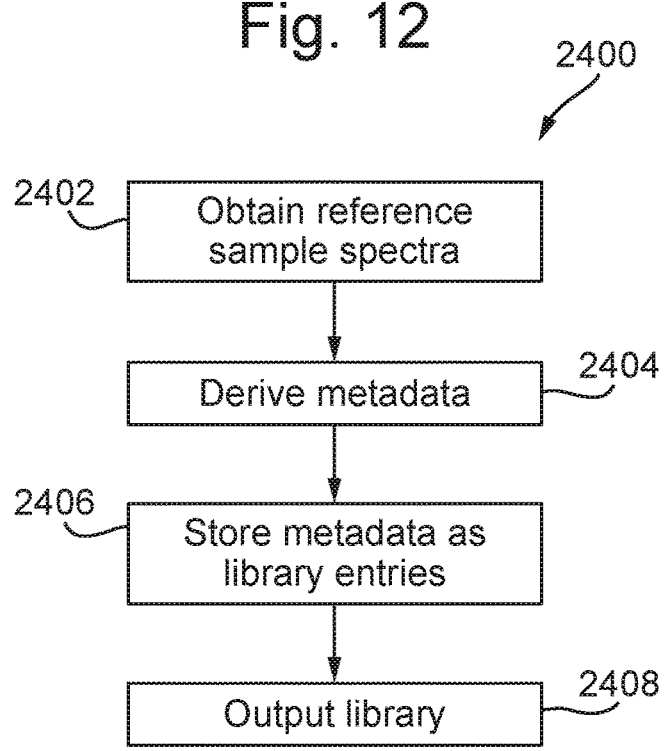
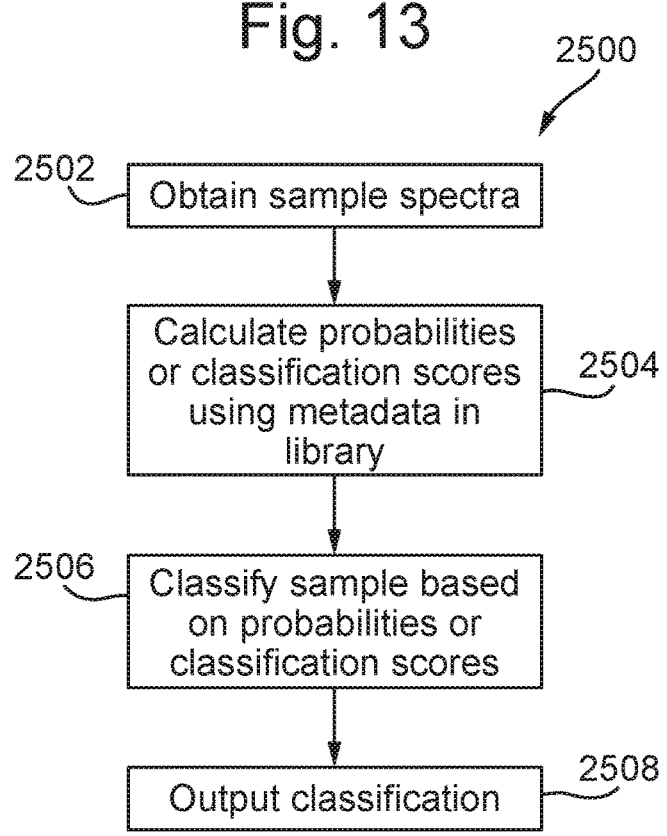

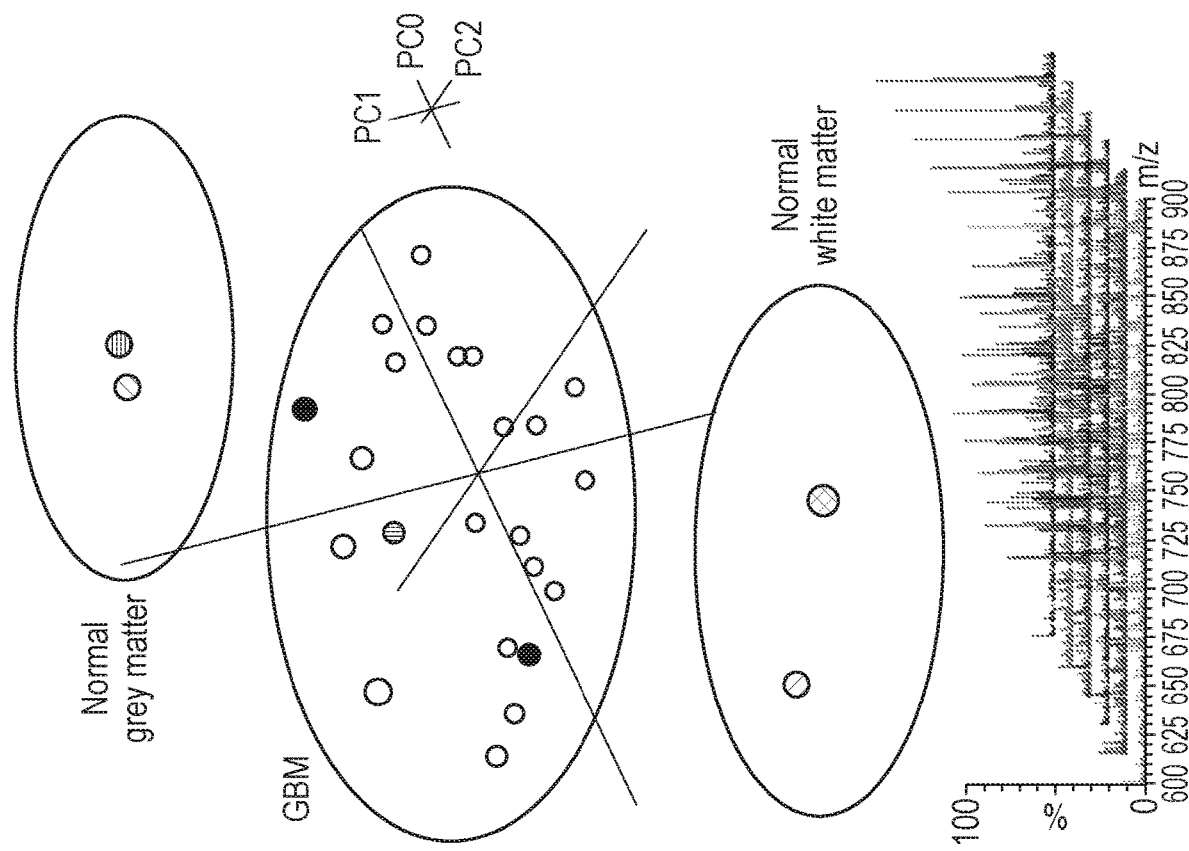
Fig. 16
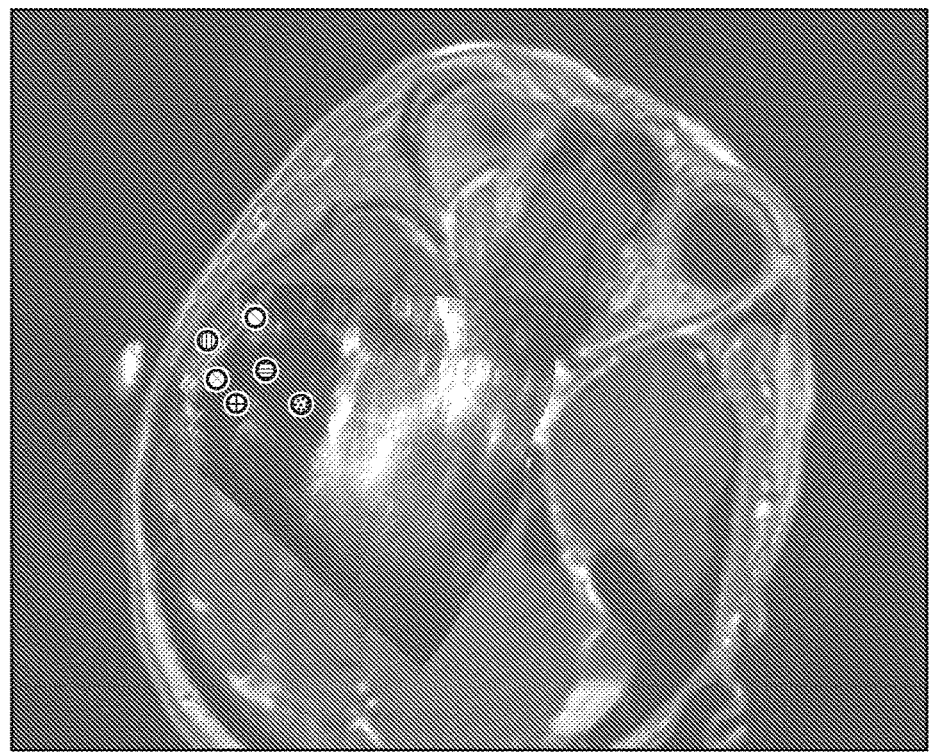

CHEMICALLY GUIDED AMBIENT IONISATION MASS SPECTROMETRY

CROSS-REFERENCE TO RELATED APPLICATIONS

This application represents the U.S. National Phase of International Application number PCT/GB2016/050608 entitled "Chemically Guided Ambient Ionisation Mass Spectrometry" filed 7 Mar. 2016, which claims priority from and the benefit of United Kingdom patent application No. 1503876.3 filed on 6 Mar. 2015, United Kingdom patent application No. 1503864.9 filed on 6 Mar. 2015, United Kingdom patent application No. 1518369.2 filed on 16 Oct. 2015, United Kingdom patent application No. 1503877.1 filed on 6 Mar. 2015, United Kingdom patent application No. 1503867.2 filed on 6 Mar. 2015, United Kingdom patent application No. 1503863.1 filed on 6 Mar. 2015, United Kingdom patent application No. 1503878.9 filed on 6 Mar. 2015, United Kingdom patent application No. 1503879.7 filed on 6 Mar. 2015 and United Kingdom patent application No. 1516003.9 filed on 9 Sep. 2015. The entire contents of these applications are incorporated herein by reference.

FIELD OF THE INVENTION

The present invention relates generally to the analysis of a target (which may, for example, comprise in vivo, ex vivo or in vitro biological tissue, a bacterial or fungal colony or more generally an organic target such as a plastic) by ambient ionisation techniques such as rapid evaporative ionisation mass spectrometry ("REIMS"), methods of analysis and diagnosis and apparatus for analysing a target using an ambient ionisation ion source. Various embodiments are contemplated wherein analyte ions generated by an ambient ionisation ion source are then subjected either to: (i) mass analysis by a mass analyser such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly ion mobility analysis (IMS) and/or differential ion mobility analysis (DMA) and/or Field Asymmetric Ion Mobility Spectrometry (FAIMS) analysis followed by secondly mass analysis by a mass analyser such as a quadrupole mass analyser or a Time of Flight mass analyser (or vice versa). Various embodiments also relate to an ion mobility spectrometer and/or mass analyser and a method of ion mobility spectrometry and/or method of mass analysis.

BACKGROUND

Rapid evaporative ionisation mass spectrometry ("REIMS") is a relatively new technique that is useful for the analysis of many different types of samples including the identification of tissue.

Reference is made to N. Strittmatter et al., Anal. Chem. 2014, 86, 6555-6562 which discloses an investigation into the suitability of using rapid evaporative ionisation mass spectrometry as a general identification system for bacteria and fungi.

The known approach for analysing bacterial colonies by rapid evaporative ionisation mass spectrometry involves using bipolar electrosurgical forceps and an electrosurgical RF generator. A bacterial colony is scraped from the surface of an agar layer using the bipolar electrosurgical forceps and a short burst of RF voltage from the electrosurgical RF generator is applied between the bipolar electrosurgical forceps. For example, it is known to apply 60 W of power in a bipolar mode at a frequency of 470 kHz sinusoid. The RF voltage which is applied to the electrosurgical forceps has the result of rapidly heating the particular portion of the bacterial colony which is being analysed due to its nonzero impedance. The rapid heating of the microbial mass results in an aerosol being generated. The aerosol is transferred directly into a mass spectrometer and the aerosol sample may then be analysed by the mass spectrometer. It is known for the control system of the mass spectrometer to utilise multivariate statistical analysis in order to help distinguish and identify different samples.

Brain cancers are one of the leading causes of cancer-related deaths in children and young adults. Surgical resection of primary brain tumours is still the most often used therapy. However, in many cases the complete removal of the cancer is very difficult without damaging a vital function and it is problematic to accurately determine the margins of cancerous tissue when performing a resection of a brain tumour.

It is desired to provide an improved method of analysing a target or tissue using an ambient ionisation ion source.

SUMMARY

According to an aspect there is provided a method comprising:

obtaining or acquiring chemical or other non-mass spectrometric data from one or more regions of a target; and using a first device to generate aerosol, smoke or vapour from one or more regions of the target.

A workflow has been developed which uses an optical method (such as Raman spectroscopy) followed by a mass spectrometry based method (such as rapid evaporative ionisation mass spectrometry ("REIMS")) for cancer tissue identification within an operating theatre or other environments.

Raman spectroscopy is a non-invasive laser based method which probes the molecular vibrations and excitations of molecules within a target (e.g., tissue).

In particular, various embodiments are disclosed which relate to the combination of Raman spectroscopy and rapid evaporative ionisation mass spectrometry in the context of brain surgery. The approach may be validated by, for example, using an in vivo three dimensional ultrasonic neuronavigational system together with conventional histopathology. Various three dimensional ultrasonic neuronavigational systems are known including SonoWand® and such navigational systems may be utilised according to various embodiments.

Experimental results are presented which demonstrate how the combination of rapid evaporative ionisation mass spectrometry ("REIMS") together with Raman spectroscopy enables a high degree of tissue specificity to be achieved especially by analysing the tissue sample in the phospholipid region.

The various embodiments which are disclosed enable healthy tissue to be accurately distinguished from cancerous tissue and in particular enable different brain cancers to be accurately determined during an operation. The combination of Raman spectroscopy and rapid evaporative ionisation mass spectrometry ("REIMS") is particularly beneficial as it enables important information to be provided to a surgeon and the disclosed technique is beneficial in the assessment of tumour margins which can beneficially lead to an increase in the survival rate of patients.

Further details of a combined Raman spectroscopy and rapid evaporative ionisation mass spectrometry ("REIMS") method for the in situ identification of brain tumours during surgery are disclosed below.

Although the following disclosure relates inter alia to improvements in the assessment of tumour margins during brain surgery, it should be understood that further embodiments are contemplated wherein other parts of the body or other organs may be sampled using Raman spectroscopy (or another chemical sensing method) followed by analysis using an ambient ion source such as a rapid evaporative ionisation mass spectrometry ("REIMS") ion source. In particular, it should be understood that ambient ionisation ion sources other than a rapid evaporative ionisation mass spectrometry ("REIMS") ion source may be used.

In accordance with various embodiments chemical data may be acquired from a target (which may comprise in vivo, ex vivo or in vitro biological tissue, a bacterial or fungal colony or a more general organic target such as a plastic).

The method may further comprise using the chemical or other non-mass spectrometric data to determine one or more regions of interest of the target.

The chemical or other non-mass spectrometric data may comprise data selected from the group consisting of: (i) Raman spectroscopy data; (ii) chemical composition data; (iii) fluorescence data; (iv) absorption data; (v) reflectance data; (vi) transmission data; (vii) elastic scattering data; (viii) Fourier Transform Infra-Red Spectroscopy (FTIR) data; and (ix) interferometry data.

The first device may comprise or form part of an ambient ion or ionisation source or the first device may generate the aerosol, smoke or vapour for subsequent ionisation by an ambient ion or ionisation source or other ionisation source.

The target may comprise native or unmodified target material.

The native or unmodified target material may be unmodified by the addition of a matrix or reagent.

The first device may be arranged and adapted to generate aerosol, smoke or vapour from one or more regions of the target without the target requiring prior preparation.

The first device may comprise an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a focussed or unfocussed ultrasonic ablation device; (xxii) a microwave resonance device; and (xxiii) a pulsed plasma RF dissection device.

The step of using the first device to generate aerosol, smoke or vapour from one or more regions of the target further may comprise contacting the target with one or more electrodes.

The one or more electrodes may comprise a bipolar device or a monopolar device.

The one or more electrodes may comprise a rapid evaporation ionization mass spectrometry ("REIMS") device.

The method may further comprise applying an AC or RF voltage to the one or more electrodes in order to generate the aerosol, smoke or vapour.

The step of applying the AC or RF voltage to the one or more electrodes may comprise applying one or more pulses of the AC or RF voltage to the one or more electrodes.

The step of applying the AC or RF voltage to the one or more electrodes may cause heat to be dissipated into the target.

The step of using the first device to generate aerosol, smoke or vapour from one or more regions of the target further may comprise irradiating the target with a laser.

The first device may be arranged and adapted to generate aerosol from one or more regions of the target by direct evaporation or vaporisation of target material from the target by Joule heating or diathermy.

The step of using the first device to generate aerosol, smoke or vapour from one or more regions of the target further may comprise directing ultrasonic energy into the target.

The aerosol may comprise uncharged aqueous droplets optionally comprising cellular material.

At least 50%, 55%, 60%, 65%, 70%, 75%, 80%, 85%, 90% or 95% of the mass or matter generated by the first device and which forms the aerosol may be in the form of droplets.

The first device may be arranged and adapted to generate aerosol wherein the Sauter mean diameter ("SMD", d32) of the aerosol may be in a range: (i) <5 µm; (ii) 5-10 µm; (iii) 10-15 µm; (iv) 15-20 µm; (v) 20-25 µm; or (vi) >25 µm.

The aerosol may traverse a flow region with a Reynolds number (Re) in the range: (i) <2000; (ii) 2000-2500; (iii) 2500-3000; (iv) 3000-3500; (v) 3500-4000; or (vi) >4000.

Substantially at the point of generating the aerosol, the aerosol may comprise droplets having a Weber number (We) selected from the group consisting of: (i) <50; (ii) 50-100; (iii) 100-150; (iv) 150-200; (v) 200-250; (vi) 250-300; (vii) 300-350; (viii) 350-400; (ix) 400-450; (x) 450-500; (xi) 500-550; (xii) 550-600; (xiii) 600-650; (xiv) 650-700; (xv) 700-750; (xvi) 750-800; (xvii) 800-850; (xviii) 850-900; (xix) 900-950; (xx) 950-1000; and (xxi) >1000.

Substantially at the point of generating the aerosol, the aerosol may comprise droplets having a Stokes number ($S_k$) in the range: (i) 1-5; (ii) 5-10; (iii) 10-15; (iv) 15-20; (v) 20-25; (vi) 25-30; (vii) 30-35; (viii) 35-40; (ix) 40-45; (x) 45-50; and (xi) >50.

Substantially at the point of generating the aerosol, the aerosol may comprise droplets having a mean axial velocity selected from the group consisting of: (i) <20 m/s; (ii) 20-30 m/s; (iii) 30-40 m/s; (iv) 40-50 m/s; (v) 50-60 m/s; (vi) 60-70 m/s; (vii) 70-80 m/s; (viii) 80-90 m/s; (ix) 90-100 m/s; (x) 100-110 m/s; (xi) 110-120 m/s; (xii) 120-130 m/s; (xiii) 130-140 m/s; (xiv) 140-150 m/s; and (xv) >150 m/s.

The target may comprise biological tissue, biological matter, a bacterial colony or a fungal colony.

The biological tissue may comprise human tissue or non-human animal tissue.

The biological tissue may comprise in vivo biological tissue.

The biological tissue may comprise ex vivo biological tissue.

The biological tissue may comprise in vitro biological tissue.

The biological tissue may comprise: (i) adrenal gland tissue, appendix tissue, bladder tissue, bone, bowel tissue, brain tissue, breast tissue, bronchi, coronal tissue, ear tissue, esophagus tissue, eye tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, ureter tissue, urethra tissue, soft and connective tissue, peritoneal tissue, blood vessel tissue and/or fat tissue; (ii) grade I, grade II, grade III or grade IV cancerous tissue; (iii) metastatic cancerous tissue; (iv) mixed grade cancerous tissue; (v) a sub-grade cancerous tissue; (vi) healthy or normal tissue; or (vii) cancerous or abnormal tissue.

The first device may comprise a point of care ("POC"), diagnostic or surgical device.

The method may further comprise ionising at least some of the aerosol, smoke or vapour so as to generate analyte ions.

The method may further comprise directing or aspirating at least some of the aerosol, smoke or vapour into a vacuum chamber of a mass spectrometer.

The method may further comprise ionising at least some the aerosol, smoke or vapour within a or the vacuum chamber of the mass spectrometer so as to generate a plurality of analyte ions.

The method may further comprise causing the aerosol, smoke or vapour to impact upon a collision surface located within a vacuum chamber of the mass spectrometer so as to generate a plurality of analyte ions.

The method may further comprise mass analysing and/or ion mobility analysing the analyte ions in order to obtain mass spectrometric data and/or ion mobility data.

Various embodiments are contemplated wherein analyte ions generated by an ambient ionisation ion source are then subjected either to: (i) mass analysis by a mass analyser such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly ion mobility analysis (IMS) and/or differential ion mobility analysis (DMA) and/or Field Asymmetric Ion Mobility Spectrometry (FAIMS) analysis followed by secondly mass analysis by a mass analyser such as a quadrupole mass analyser or a Time of Flight mass analyser (or vice versa). Various embodiments also relate to an ion mobility spectrometer and/or mass analyser and a method of ion mobility spectrometry and/or method of mass analysis.

The method may further comprise mass analysing and/or ion mobility analysing the aerosol, smoke or vapour or ions derived from the aerosol, smoke or vapour in order to obtain mass spectrometric data and/or ion mobility data.

The method may further comprise analysing the mass spectrometric data and/or ion mobility data in order either: (i) to distinguish between healthy and diseased tissue; (ii) to distinguish between potentially cancerous and non-cancerous tissue; (iii) to distinguish between different types or grades of cancerous tissue; (iv) to distinguish between different types or classes of target material; (v) to determine whether or not one or more desired or undesired substances are present in the target; (vi) to confirm the identity or authenticity of the target; (vii) to determine whether or not one or more impurities, illegal substances or undesired substances are present in the target; (viii) to determine whether a human or animal patient may be at an increased risk of suffering an adverse outcome; (ix) to make or assist in the making a diagnosis or prognosis; and (x) to inform a surgeon, nurse, medic or robot of a medical, surgical or diagnostic outcome.

The step of analysing the mass spectrometric data and/or ion mobility data may comprise performing a supervised or unsupervised multivariate statistical analysis of the mass spectrometric data and/or ion mobility data.

The multivariate statistical analysis may be selected from the group consisting of: (i) principal component analysis ("PCA"); and (ii) linear discriminant analysis ("LDA").

The step of analysing the mass spectrometric data and/or ion mobility data may further comprise analysing a profile of the aerosol, smoke or vapour or a profile of ions derived from the aerosol, smoke or vapour.

The profile may be selected from the group consisting of: (i) a lipidomic profile; (ii) a fatty acid profile; (iii) a phospholipid profile; (iv) a phosphatidic acid (PA) profile; (v) a phosphatidylethanolamine (PE) profile; (vi) a phosphatidylglycerol (PG) profile; (vii) a phosphatidylserines (PS) profile; (viii) a phosphatidylinositol (PI) profile; or (ix) a triglyceride (TG) profile.

The method may further comprise using one or more Raman spectroscopy sensors, detectors or devices to obtain the chemical or other non-mass spectrometric data.

The method may further comprise determining the intensity of Raman scattered light as a function of wavenumber.

The method may further comprise analysing Raman spectroscopy data in order to determine data relating to vibrations of molecular bonds present within the target.

The method may further comprise using the one or more Raman spectroscopy sensors, detectors or devices to obtain the chemical or other non-mass spectrometric data with or without the one or more Raman spectroscopy sensors, detectors or devices physically contacting the target.

The method may further comprise determining a Raman spectrum or Raman profile of one or more regions of the target.

The method may further comprise using the chemical or other non-mass spectrometric data to determine one or more regions of interest of the target by determining one or more regions of the target which have a different Raman spectrum, Raman profile or Raman spectral feature relative to normal tissue, surrounding tissue, a control sample, a control region, control data or predetermined data.

The method may further comprise using the chemical or other non-mass spectrometric data to determine one or more regions of interest of the target by determining whether or not a region of the target has a higher or lower Raman peak intensity relative to normal tissue, surrounding tissue, a control sample, a control region, control data or predetermined data.

The method may further comprise directing light or ultra-violet radiation on to the target.

The ultra-violet radiation may have a wavelength in a range selected from the group consisting of: (i) 100-150 nm; (ii) 150-200 nm; (iii) 200-250 nm; (iv) 250-300 nm; (v) 300-350 nm; and (vi) 350-400 nm.

The method may further comprise detecting light or electromagnetic radiation emitted from the target.

The method may further comprise determining a fluorescence or autofluorescence profile or spectrum.

The fluorescence or autofluorescence profile or spectrum may comprise a measure of the intensity of light or electromagnetic radiation emitted from the target as a function of frequency or wavelength.

The method may further comprise comparing a fluorescence or autofluorescence profile or spectrum relating to a region of the target with a fluorescence or autofluorescence profile or spectrum obtained from a control sample, a control region, control data or predetermined data in order to determining one or more regions of interest of the target.

The method may further comprise directing light or infra-red radiation on to the target.

The light or infra-red radiation may have a wavelength in a range selected from the group consisting of: (i) 400-450 nm; (ii) 450-500 nm; (iii) 500-550 nm; (iv) 550-600 nm; (v) 600-650 nm; (vi) 650-700 nm; (vii) 700-750 nm; (viii) 750-800 nm; (ix) 800-850 nm; (x) 850-900 nm; (xi) 900-950 nm; (xii) 950-1000 nm; (xiii) 1000-1100 nm; (xiv) 1100-1200 nm; (xv) 1200-1300 nm; (xvi) 1300-1400 nm; (xvii) 1400-1500 nm; (xviii) 1500-1600 nm; (xix) 1600-1700 nm; (xx) 1700-1800 nm; (xxi) 1800-1900 nm; (xxii) 1900-2000 nm; (xxiii) 2000-2100 nm; (xxiv) 2100-2200 nm; (xxv) 2200-2300 nm; (xxvi) 2300-2400 nm; (xxvii) 2400-2500 nm; (xxviii) 2500-2600 nm; (xxix) 2600-2700 nm; (xxx) 2700-2800 nm; (xxxi) 2800-2900 nm; and (xxxii) 2900-3000 nm.

The method may further comprise directing white light on to the target.

The method may further comprise detecting light or infra-red radiation reflected by or from the target.

The method may further comprise determining an absorbance, transmission or reflectance profile or spectrum of a region of the target.

The absorbance, transmission or reflectance profile or spectrum may comprise a measure of the intensity of light absorbed by, transmitted by or reflected by the target as a function of frequency or wavelength.

The method may further comprise comparing an absorbance, transmission or reflectance profile or spectrum relating to a region of the target with an absorbance, transmission or reflectance profile or spectrum obtained from a control sample, a control region, control data or predetermined data in order to determine one or more regions of interest of the target.

The method may further comprise directing ultra-violet radiation, light or infra-red radiation on to the target.

The method may further comprise directing ultra-violet radiation, light or infra-red radiation on to the target in order to produce an interferogram as used in FTIR. Additionally or alternatively the method may comprise the application of an IR-transparent material such as KBr into one of the analysis beams to increase the optical path length.

The ultra-violet radiation, light or infra-red radiation may have a wavelength in a range selected from the group consisting of: (i) 300-350 nm; (ii) 350-400 nm; (iii) 400-450 nm; (iv) 450-500 nm; (v) 500-500 nm; (vi) 500-550 nm; (vii) 550-600 nm; (viii) 600-650 nm; (ix) 650-700 nm; (x) 700-750 nm; (xi) 750-800 nm; (xii) 800-850 nm; (xiii) 850-900 nm; (xiv) 900-950 nm; (xv) 950-1000 nm; (xvi) 1000-1100 nm; (xvii) 1100-1200 nm; (xviii) 1200-1300 nm; (xix) 1300-1400 nm; (xx) 1400-1500 nm; (xxi) 1500-1600 nm; (xxii) 1600-1700 nm; (xxiii) 1700-1800 nm; (xxiv) 1800-1900 nm; (xxv) 1900-2000 nm; (xxvi) 2000-2100 nm; (xxvii) 2100-2200 nm; (xxviii) 2200-2300 nm; (xxix) 2300-2400 nm; (xxx) 2400-2500 nm; (xxxi) 2500-2600 nm; (xxxii) 2600-2700 nm; (xxxiii) 2700-2800 nm; (xxxiv) 2800-2900 nm; and (xxxv) 2900-3000 nm.

The method may further comprise directing white light on to the target.

The method may further comprise detecting ultra-violet radiation, light or infra-red radiation reflected or scattered by the target.

The method may further comprise determining a scattered light intensity profile or spectrum of a region of the target.

The scattered light intensity profile or spectrum may comprise a measure of the intensity of light scattered by the target as a function of frequency or wavelength.

The step of determining from the chemical or other non-mass spectrometric data one or more regions of interest of the target may comprise comparing a scattered light intensity profile or spectrum relating to a region of the target with a scattered light intensity profile or spectrum obtained from a control sample, a control region, control data or predetermined data.

The method may further comprise using the chemical or other non-mass spectrometric data to determine the margins or bounds of one or more regions of interest of the target.

The one or more regions of interest may comprise cancerous biological tissue or a tumour.

The cancerous biological tissue or the tumour may comprise either: (i) grade I, grade II, grade III or grade IV cancerous tissue; (ii) metastatic cancerous tissue; (iii) mixed grade cancerous tissue; or (iv) a sub-grade cancerous tissue.

The method may further comprise determining from the chemical or other non-mass spectrometric data either: (i) one or more physical properties of the target; (ii) one or more chemical properties of the target; (iii) one or more physico-chemical properties of the target; or (iv) one or more mechanical properties of the target.

The method may further comprise using one or more contrast agents to enhance the chemical data which is acquired.

The one or more contrast agents may comprise one or more fluorescent contrast agents.

The one or more contrast agents may comprise one or more visible dyes.

The one or more contrast agents may comprise one or more radiocontrast agents.

The one or more contrast agents may comprise one or more optical, near infrared ("NIR"), fluorescent, autofluorescent or diagnostic contrast agents.

The one or more contrast agents may be selected from the group consisting of: (i) indocyanine green ("ICG") and derivatives or conjugates of indocyanine green including indotricarbocyanine; (ii) diethylthiatricarbocyanine iodide ("DTTCI") and derivatives or conjugates of diethylthiatricarbocyanine iodide; (iii) rhodamine B and derivatives or conjugates of rhodamine B; (iv) photodynamic therapy ("PDT") agents including hexylpyropheophorbide ("HPPH"); (v) a cyanine dye including Cy 5.5 dyes; and (vi) bifunctional contrast agents.

The one or more contrast agents may comprise nanoparticles.

The one or more contrast agents may comprise: (i) magnetic or ferromagnetic nanoparticles; (ii) gold nanoparticles; (iii) metallic nanoparticles; (iv) functionalised nanoparticles; (v) nanospheres, nanorods, nanostars or nanoshells; (vi) levan nanoparticles; or (vii) copper, zinc, titanium, magnesium, alginate, alloy or silver nanoparticles.

The one or more contrast agents may be exogenous to the target. Alternatively, the one or more contrast agents may be endogenous to the target.

According to another aspect there is provided a method of ambient ionisation comprising a method as disclosed above.

According to another aspect there is provided a method of rapid evaporation ionization mass spectrometry ("REIMS") comprising a method as disclosed above.

According to another aspect there is provided a method of analysis comprising a method as disclosed above.

According to another aspect there is provided a method of surgery, diagnosis, therapy or medical treatment comprising a method as disclosed above.

According to another aspect there is provided a non-surgical, non-therapeutic method of mass spectrometry and/or method of ion mobility spectrometry comprising a method as disclosed above.

According to another aspect there is provided a method of mass spectrometry and/or a method of ion mobility spectrometry comprising a method as disclosed above.

According to another aspect there is provided apparatus comprising:

a device arranged and adapted to obtain chemical or other non-mass spectrometric data from one or more regions of a target; and a first device for generating aerosol, smoke or vapour from one or more regions of the target.

The apparatus may further comprise a control system arranged and adapted to use the chemical or other non-mass spectrometric data to determine one or more regions of interest of the target.

The chemical or other non-mass spectrometric data may comprise data selected from the group consisting of: (i) Raman spectroscopy data; (ii) chemical composition data; (iii) fluorescence data; (iv) absorption data; (v) reflectance data; (vi) transmission data; (vii) elastic scattering data; (viii) Fourier Transform Infra-Red Spectroscopy (FTIR) data; and (ix) interferometry data.

The first device may comprise or form part of an ambient ion or ionisation source or the first device may generate the aerosol, smoke or vapour for subsequent ionisation by an ambient ion or ionisation source or other ionisation source.

The target may comprise native or unmodified target material.

The native or unmodified target material may be unmodified by the addition of a matrix or reagent.

The first device may be arranged and adapted to generate aerosol, smoke or vapour from one or more regions of the target without the target requiring prior preparation.

The first device may comprise an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a focussed or unfocussed ultrasonic ablation device; (xxii) a microwave resonance device; and (xxiii) a pulsed plasma RF dissection device.

The first device may be arranged and adapted to generate aerosol, smoke or vapour from one or more regions of the target by contacting the target with one or more electrodes.

The one or more electrodes may comprise: (i) a monopolar device, wherein the method optionally further comprises providing a separate return electrode; (ii) a bipolar device; or (iii) a multi phase RF device, wherein the method optionally further comprises providing a separate return electrode or electrodes.

The one or more electrodes may comprise a rapid evaporation ionization mass spectrometry ("REIMS") device.

The apparatus may further comprise a device arranged and adapted to apply an AC or RF voltage to the one or more electrodes in order to generate the aerosol, smoke or vapour.

The device for applying the AC or RF voltage to the one or more electrodes may be arranged to apply one or more pulses of the AC or RF voltage to the one or more electrodes.

Application of the AC or RF voltage to the one or more electrodes may cause heat to be dissipated into the target.

The first device may comprise a laser for irradiating the target.

The first device may be arranged and adapted to generate aerosol from one or more regions of the target by direct evaporation or vaporisation of target material from the target by Joule heating or diathermy.

The first device may be arranged and adapted to direct ultrasonic energy into the target.

The aerosol may comprise uncharged aqueous droplets optionally comprising cellular material.

At least 50%, 55%, 60%, 65%, 70%, 75%, 80%, 85%, 90% or 95% of the mass or matter generated by the first device and which forms the aerosol may be in the form of droplets.

The first device may be arranged and adapted to generate aerosol wherein the Sauter mean diameter ("SMD", d32) of the aerosol may be in a range: (i) <5 µm; (ii) 5-10 µm; (iii) 10-15 µm; (iv) 15-20 µm; (v) 20-25 µm; or (vi) >25 µm.

The aerosol may traverse a flow region with a Reynolds number (Re) in the range: (i) <2000; (ii) 2000-2500; (iii) 2500-3000; (iv) 3000-3500; (v) 3500-4000; or (vi) >4000.

Substantially at the point of generating the aerosol, the aerosol may comprise droplets having a Weber number (We) selected from the group consisting of: (i) <50; (ii) 50-100; (iii) 100-150; (iv) 150-200; (v) 200-250; (vi) 250-300; (vii) 300-350; (viii) 350-400; (ix) 400-450; (x) 450-500; (xi) 500-550; (xii) 550-600; (xiii) 600-650; (xiv) 650-700; (xv) 700-750; (xvi) 750-800; (xvii) 800-850; (xviii) 850-900; (xix) 900-950; (xx) 950-1000; and (xxi) >1000.

Substantially at the point of generating the aerosol, the aerosol may comprise droplets having a Stokes number ($S_k$) in the range: (i) 1-5; (ii) 5-10; (iii) 10-15; (iv) 15-20; (v) 20-25; (vi) 25-30; (vii) 30-35; (viii) 35-40; (ix) 40-45; (x) 45-50; and (xi) >50.

Substantially at the point of generating the aerosol, the aerosol may comprise droplets having a mean axial velocity selected from the group consisting of: (i) <20 m/s; (ii) 20-30 m/s; (iii) 30-40 m/s; (iv) 40-50 m/s; (v) 50-60 m/s; (vi) 60-70 m/s; (vii) 70-80 m/s; (viii) 80-90 m/s; (ix) 90-100 m/s; (x) 100-110 m/s; (xi) 110-120 m/s; (xii) 120-130 m/s; (xiii) 130-140 m/s; (xiv) 140-150 m/s; and (xv) >150 m/s.

The target may comprise biological tissue, biological matter, a bacterial colony or a fungal colony.

The biological tissue may comprise human tissue or non-human animal tissue.

The biological tissue may comprise in vivo biological tissue.

The biological tissue may comprise ex vivo biological tissue.

The biological tissue may comprise in vitro biological tissue.

The biological tissue comprise: (i) adrenal gland tissue, appendix tissue, bladder tissue, bone, bowel tissue, brain tissue, breast tissue, bronchi, coronal tissue, ear tissue, esophagus tissue, eye tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, ureter tissue, urethra tissue, soft and connective tissue, peritoneal tissue, blood vessel tissue and/or fat tissue; (ii) grade I, grade II, grade III or grade IV cancerous tissue; (iii) metastatic cancerous tissue; (iv) mixed grade cancerous tissue; (v) a sub-grade cancerous tissue; (vi) healthy or normal tissue; or (vii) cancerous or abnormal tissue.

The first device may comprise a point of care ("POC"), diagnostic or surgical device.

The apparatus may further comprise an ion source for ionising at least some of the aerosol, smoke or vapour so as to generate analyte ions.

The apparatus may further comprise a device for directing or aspirating at least some of the aerosol, smoke or vapour into a vacuum chamber of a mass spectrometer and/or ion mobility spectrometer.

The apparatus may further comprise a device for ionising at least some the aerosol, smoke or vapour within a or the vacuum chamber of the mass spectrometer and/or ion mobility spectrometer so as to generate a plurality of analyte ions.

The apparatus may further comprise a device for directing the aerosol, smoke or vapour to impact upon a collision surface located within a vacuum chamber of the mass spectrometer and/or ion mobility spectrometer so as to generate a plurality of analyte ions.

The apparatus may further comprise a mass analyser and/or ion mobility spectrometer for mass analysing and/or ion mobility separating the analyte ions in order to obtain mass spectrometric data and/or ion mobility data.

The apparatus may further comprise a mass analyser and/or ion mobility spectrometer for mass analysing and/or ion mobility separating the aerosol, smoke or vapour or ions derived from the aerosol, smoke or vapour in order to obtain mass spectrometric data and/or ion mobility data.

The apparatus may further comprise a control system arranged and adapted to analyse the mass spectrometric data and/or ion mobility data in order either: (i) to distinguish between healthy and diseased tissue; (ii) to distinguish between potentially cancerous and non-cancerous tissue; (iii) to distinguish between different types or grades of cancerous tissue; (iv) to distinguish between different types or classes of target material; (v) to determine whether or not one or more desired or undesired substances are present in the target; (vi) to confirm the identity or authenticity of the target; (vii) to determine whether or not one or more impurities, illegal substances or undesired substances are present in the target; (viii) to determine whether a human or animal patient may be at an increased risk of suffering an adverse outcome; (ix) to make or assist in the making a diagnosis or prognosis; and (x) to inform a surgeon, nurse, medic or robot of a medical, surgical or diagnostic outcome.

The control system may be arranged and adapted to perform a supervised or unsupervised multivariate statistical analysis of the mass spectrometric data and/or ion mobility data.

The multivariate statistical analysis be may be selected from the group consisting of: (i) principal component analysis be ("PCA"); and (ii) linear discriminant analysis ("LDA").

The apparatus may further comprise a control system arranged and adapted to analyse a profile of the aerosol, smoke or vapour or a profile of ions derived from the aerosol, smoke or vapour.

The profile may be selected from the group consisting of: (i) a lipidomic profile; (ii) a fatty acid profile; (iii) a phospholipid profile; (iv) a phosphatidic acid (PA) profile; (v) a phosphatidylethanolamine (PE) profile; (vi) a phosphatidylglycerol (PG) profile; (vii) a phosphatidylserines (PS) profile; (viii) a phosphatidylinositol (PI) profile; or (ix) a triglyceride (TG) profile.

The apparatus may further comprise one or more Raman spectroscopy sensors, detectors or devices for obtaining the chemical or other non-mass spectrometric data.

The apparatus may further comprise a control system arranged and adapted to determine the intensity of Raman scattered light as a function of wavenumber.

The apparatus may further comprise a control system arranged and adapted to analyse Raman spectroscopy data in order to determine data relating to vibrations of molecular bonds present within the target.

The one or more Raman spectroscopy sensors, detectors or devices may be arranged to obtain the chemical or other non-mass spectrometric data with or without the one or more Raman spectroscopy sensors, detectors or devices physically contacting the target.

The apparatus may further comprise a control system arranged and adapted to determine a Raman spectrum or Raman profile of one or more regions of the target.

The apparatus may further comprise a control system arranged and adapted to determine one or more regions of interest of the target by determining one or more regions of the target which have a different Raman spectrum, Raman profile or Raman spectral feature relative to normal tissue, surrounding tissue, a control sample, a control region, control data or predetermined data.

The apparatus may further comprise a control system arranged and adapted to determine one or more regions of interest of the target by determining whether or not a region of the target may have a higher or lower Raman peak intensity relative to normal tissue, surrounding tissue, a control sample, a control region, control data or predetermined data.

The apparatus may further comprise a device for directing light or ultra-violet radiation on to the target.

The ultra-violet radiation may have a wavelength in a range selected from the group consisting of: (i) 100-150 nm; (ii) 150-200 nm; (iii) 200-250 nm; (iv) 250-300 nm; (v) 300-350 nm; and (vi) 350-400 nm.

The apparatus may further comprise a detector for detecting light or electromagnetic radiation emitted from the target.

The apparatus may further comprise a control system arranged and adapted to determine a fluorescence or autofluorescence profile or spectrum.

The fluorescence or autofluorescence profile or spectrum may comprise a measure of the intensity of light or electromagnetic radiation emitted from the target as a function of frequency or wavelength.

The apparatus may further comprise a control system arranged and adapted to compare a fluorescence or autofluorescence profile or spectrum relating to a region of the target with a fluorescence or autofluorescence profile or spectrum obtained from a control sample, a control region, control data or predetermined data in order to determining one or more regions of interest of the target.

The apparatus may further comprise a device arranged to direct light or infra-red radiation on to the target.

The light or infra-red radiation may have a wavelength in a range selected from the group consisting of: (i) 400-450 nm; (ii) 450-500 nm; (iii) 500-550 nm; (iv) 550-600 nm; (v) 600-650 nm; (vi) 650-700 nm; (vii) 700-750 nm; (viii) 750-800 nm; (ix) 800-850 nm; (x) 850-900 nm; (xi) 900-950 nm; (xii) 950-1000 nm; (xiii) 1000-1100 nm; (xiv) 1100-1200 nm; (xv) 1200-1300 nm; (xvi) 1300-1400 nm; (xvii) 1400-1500 nm; (xviii) 1500-1600 nm; (xix) 1600-1700 nm; (xx) 1700-1800 nm; (xxi) 1800-1900 nm; (xxii) 1900-2000 nm; (xxiii) 2000-2100 nm; (xxiv) 2100-2200 nm; (xxv) 2200-2300 nm; (xxvi) 2300-2400 nm; (xxvii) 2400-2500 nm; (xxviii) 2500-2600 nm; (xxix) 2600-2700 nm; (xxx) 2700-2800 nm; (xxxi) 2800-2900 nm; and (xxxii) 2900-3000 nm.

The apparatus may further comprise a device arranged to direct white light on to the target.

The apparatus may further comprise a device arranged to detect light or infra-red radiation reflected by or from the target.

The apparatus may further comprise a control system arranged and adapted to determine an absorbance, transmission or reflectance profile or spectrum of a region of the target.

The absorbance, transmission or reflectance profile or spectrum may comprise a measure of the intensity of light absorbed by, transmitted by or reflected by the target as a function of frequency or wavelength.

The apparatus may further comprise a control system arranged and adapted to compare an absorbance, transmission or reflectance profile or spectrum relating to a region of the target with an absorbance, transmission or reflectance profile or spectrum obtained from a control sample, a control region, control data or predetermined data in order to determine one or more regions of interest of the target.

The apparatus may further comprise a device arranged and adapted to direct ultra-violet radiation, light or infra-red radiation on to the target.

The ultra-violet radiation, light or infra-red radiation may have a wavelength in a range selected from the group consisting of: (i) 300-350 nm; (ii) 350-400 nm; (iii) 400-450 nm; (iv) 450-500 nm; (v) 500-500 nm; (vi) 500-550 nm; (vii) 550-600 nm; (viii) 600-650 nm; (ix) 650-700 nm; (x) 700-750 nm; (xi) 750-800 nm; (xii) 800-850 nm; (xiii) 850-900 nm; (xiv) 900-950 nm; (xv) 950-1000 nm; (xvi) 1000-1100 nm; (xvii) 1100-1200 nm; (xviii) 1200-1300 nm; (xix) 1300-1400 nm; (xx) 1400-1500 nm; (xxi) 1500-1600 nm; (xxii) 1600-1700 nm; (xxiii) 1700-1800 nm; (xxiv) 1800-1900 nm; (xxv) 1900-2000 nm; (xxvi) 2000-2100 nm; (xxvii) 2100-2200 nm; (xxviii) 2200-2300 nm; (xxix) 2300-2400 nm; (xxx) 2400-2500 nm; (xxxi) 2500-2600 nm; (xxxii) 2600-2700 nm; (xxxiii) 2700-2800 nm; (xxxiv) 2800-2900 nm; and (xxxv) 2900-3000 nm.

The apparatus may further comprise a device arranged to direct white light on to the target.

The apparatus may further comprise a detector for detecting ultra-violet radiation, light or infra-red radiation reflected or scattered by the target.

The apparatus may further comprise a control system arranged and adapted to determine a scattered light intensity profile or spectrum of a region of the target.

The scattered light intensity profile or spectrum may comprise a measure of the intensity of light scattered by the target as a function of frequency or wavelength.

The apparatus may further comprise a control system arranged and adapted to compare a scattered light intensity profile or spectrum relating to a region of the target with a scattered light intensity profile or spectrum obtained from a control sample, a control region, control data or predetermined data.

The apparatus may further comprise a control system arranged and adapted to use the chemical or other non-mass spectrometric data to determine the margins or bounds of one or more regions of interest of the target.

The one or more regions of interest may comprise cancerous biological tissue or a tumour.

The cancerous biological tissue or the tumour may comprise either: (i) grade I, grade II, grade III or grade IV cancerous tissue; (ii) metastatic cancerous tissue; (iii) mixed grade cancerous tissue; or (iv) a sub-grade cancerous tissue.

The apparatus may further comprise a control system arranged and adapted to determine from the chemical or other non-mass spectrometric data either: (i) one or more physical properties of the target; (ii) one or more chemical properties of the target; (iii) one or more physico-chemical properties of the target; or (iv) one or more mechanical properties of the target.

The apparatus may further comprise using one or more contrast agents to enhance the chemical data.

The one or more contrast agents may comprise one or more fluorescent contrast agents.

The one or more contrast agents may comprise one or more visible dyes.

The one or more contrast agents may comprise one or more radiocontrast agents.

The one or more contrast agents may comprise one or more optical, near infrared ("NIR"), fluorescent, autofluorescent or diagnostic contrast agents.

The one or more contrast agents may be selected from the group consisting of: (i) indocyanine green ("ICG") and derivatives or conjugates of indocyanine green including indotricarbocyanine; (ii) diethylthiatricarbocyanine iodide ("DTTCI") and derivatives or conjugates of diethylthiatricarbocyanine iodide; (iii) rhodamine B and derivatives or conjugates of rhodamine B; (iv) photodynamic therapy ("PDT") agents including hexylpyropheophorbide ("HPPH"); (v) a cyanine dye including Cy 5.5 dyes; and (vi) bifunctional contrast agents.

The one or more contrast agents may comprise nanoparticles.

The one or more contrast agents may comprise: (i) magnetic or ferromagnetic nanoparticles; (ii) gold nanoparticles; (iii) metallic nanoparticles; (iv) functionalised nanoparticles; (v) nanospheres, nanorods, nanostars or nanoshells; (vi) levan nanoparticles; or (vii) copper, zinc, titanium, magnesium, alginate, alloy or silver nanoparticles.

The one or more contrast agents may be exogenous to the target. Alternatively, the one or more contrast agents may be endogenous to the target.

According to another aspect there is provided an ambient ionisation ion source comprising apparatus as disclosed above.

According to another aspect there is provided a rapid evaporation ionization mass spectrometry ("REIMS") ion source comprising apparatus as disclosed above.

According to another aspect there is provided analysis apparatus as disclosed above.

According to another aspect there is provided a mass spectrometer and/or ion mobility spectrometer comprising apparatus as disclosed above.

According to another aspect there is provided a method of rapid evaporative ionisation mass spectrometry ("REIMS") comprising:

using a Raman spectroscopy probe to sample a site;
generating an aerosol from the site; and
mass analysing and/or ion mobility analysing the aerosol or analyte ions derived from the aerosol.

The site may comprise a surgical site.

The step of using the Raman spectroscopy probe to sample the site may comprise using information derived from the probe to determine the margins or bounds of one or more undesired objects at the site.

The one or more undesired objects may comprise cancerous biological tissue or a tumour.

The cancerous biological tissue or the tumour may comprise grade I, grade II, grade III or grade IV cancerous tissue.

The step of mass analysing and/or ion mobility analysing the aerosol or analyte ions derived from the aerosol further may comprise distinguishing between healthy tissue and non-healthy or cancerous tissue.

The step of mass analysing and/or ion mobility analysing the aerosol or analyte ions derived from the aerosol further may comprise distinguishing between different types or grades of cancerous tissue.

The method may further comprise localising one or more sampling points using ultrasound.

The method may further comprise using an electrosurgical device to sample the site at one or more sampling points.

The electrosurgical device may comprise a bipolar device.

The method may further comprise applying an AC or RF voltage to the electrosurgical device in order to remove, resect or sample biological material from the site.

According to another aspect there is provided a method of surgery comprising a method as disclosed above.

The method may comprise a method of brain surgery.

According to another aspect there is provided apparatus for performing rapid evaporative ionisation mass spectrometry ("REIMS") comprising:

a Raman spectroscopy probe for sampling a site;
a device for generating an aerosol from the site; and
a mass analyser and/or ion mobility analyser for mass analysing and/or ion mobility analysing the aerosol or analyte ions derived from the aerosol.

According to another aspect there is provided a method of analysing a sample comprising:

using a Raman spectroscopy probe to sample a site;
generating an aerosol from the site; and
mass analysing and/or ion mobility analysing the aerosol or analyte ions derived from the aerosol.

The step of generating an aerosol further may comprise using a laser to generate the aerosol.

The step of generating an aerosol may further comprise contacting the site with one or more electrodes and applying an AC or RF voltage to the one or more electrodes.

According to another aspect there is provided apparatus for analysing a sample comprising:

a Raman spectroscopy probe for sampling a site;
a device for generating an aerosol from the site; and
a mass analyser and/or ion mobility analyser for mass analysing and/or ion mobility analysing the aerosol or analyte ions derived from the aerosol.

According to another aspect there is provided a method of biological tissue typing comprising:

contacting a portion of tissue with one or more electrodes;
applying an AC or RF voltage to the one or more electrodes in order to generate an aerosol from the portion of tissue;
mass analysing and/or ion mobility analysing the aerosol or analyte ions derived from the aerosol in order to generate mass spectral data and/or ion mobility data; and
analysing the mass spectral data and/or ion mobility data in order to distinguish between different types of tissue.

The different types of tissue may comprise different grades, forms or types of cancerous biological tissue or tumours.

The step of analysing the mass spectral data in order to distinguish between different types of tissue further may comprise distinguishing between grade I and/or grade II and/or grade III and/or grade IV cancerous tissue.

According to another aspect there is provided apparatus for biological tissue typing comprising:

one or more electrodes which may be arranged and adapted to contact a portion of tissue;
a device for applying an AC or RF voltage to the one or more electrodes in order to generate an aerosol from the portion of tissue;
a mass analyser and/or ion mobility analyser for mass analysing and/or ion mobility analysing the aerosol or analyte ions derived from the aerosol in order to generate mass spectral data; and
a control system for analysing the mass spectral data and/or ion mobility data in order to distinguish between different types of tissue.

Various embodiments are contemplated which relate to generating smoke, aerosol or vapour from a target (details of which are provided elsewhere herein) using an ambient ionisation ion source. The aerosol, smoke or vapour may then be mixed with a matrix and aspirated into a vacuum chamber of a mass spectrometer and/or ion mobility spectrometer. The mixture may be caused to impact upon a collision surface causing the aerosol, smoke or vapour to be ionised by impact ionization which results in the generation of analyte ions. The resulting analyte ions (or fragment or product ions derived from the analyte ions) may then be mass analysed and/or ion mobility analysed and the resulting mass spectrometric data and/or ion mobility spectrometric data may be subjected to multivariate analysis or other mathematical treatment in order to determine one or more properties of the target in real time.

According to an embodiment the first device for generating aerosol, smoke or vapour from the target may comprise a tool which utilises an RF voltage, such as a continuous RF waveform.

Other embodiments are contemplated wherein the first device for generating aerosol, smoke or vapour from the target may comprise an argon plasma coagulation ("APC") device. An argon plasma coagulation device involves the use of a jet of ionised argon gas (plasma) that is directed through a probe. The probe may be passed through an endoscope. Argon plasma coagulation is essentially a non-contact process as the probe is placed at some distance from the target. Argon gas is emitted from the probe and is then ionized by a high voltage discharge (e.g., 6 kV). High-frequency electric current is then conducted through the jet of gas, resulting in coagulation of the target on the other end of the jet. The depth of coagulation is usually only a few millimetres.

The first device, surgical or electrosurgical tool, device or probe or other sampling device or probe disclosed in any of the aspects or embodiments herein may comprise a non-contact surgical device, such as one or more of a hydrosurgical device, a surgical water jet device, an argon plasma coagulation device, a hybrid argon plasma coagulation device, a water jet device and a laser device.

A non-contact surgical device may be defined as a surgical device arranged and adapted to dissect, fragment, liquefy, aspirate, fulgurate or otherwise disrupt biologic tissue without physically contacting the tissue. Examples include laser devices, hydrosurgical devices, argon plasma coagulation devices and hybrid argon plasma coagulation devices.

As the non-contact device may not make physical contact with the tissue, the procedure may be seen as relatively safe and can be used to treat delicate tissue having low intracellular bonds, such as skin or fat.

According to various embodiments the mass spectrometer and/or ion mobility spectrometer may obtain data in negative ion mode only, positive ion mode only, or in both positive and negative ion modes. Positive ion mode spectrometric data may be combined or concatenated with negative ion mode spectrometric data. Negative ion mode can provide particularly useful spectra for classifying aerosol, smoke or vapour samples, such as aerosol, smoke or vapour samples from targets comprising lipids.

Ion mobility spectrometric data may be obtained using different ion mobility drift gases, or dopants may be added to the drift gas to induce a change in drift time of one or more species. This data may then be combined or concatenated.

It will be apparent that the requirement to add a matrix or a reagent directly to a sample may prevent the ability to perform in vivo analysis of tissue and also, more generally, prevents the ability to provide a rapid simple analysis of target material.

According to other embodiments the ambient ionisation ion source may comprise an ultrasonic ablation ion source or a hybrid electrosurgical-ultrasonic ablation source that generates a liquid sample which is then aspirated as an aerosol. The ultrasonic ablation ion source may comprise a focused or unfocussed ultrasound.

Optionally, the first device comprises or forms part of an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a hybrid CUSA-diathermy device; (xxii) a focussed or unfocussed ultrasonic ablation device; (xxiii) a hybrid focussed or unfocussed ultrasonic ablation and diathermy device; (xxiv) a microwave resonance device; (xxv) a pulsed plasma RF dissection device; (xxvi) an argon plasma coagulation device; (xxvi) a hybrid pulsed plasma RF dissection and argon plasma coagulation device; (xxvii) a hybrid pulsed plasma RF dissection and JeDI device; (xxviii) a surgical water/saline jet device; (xxix) a hybrid electrosurgery and argon plasma coagulation device; and (xxx) a hybrid argon plasma coagulation and water/saline jet device.

BRIEF DESCRIPTION OF THE DRAWINGS

Various embodiments will now be described, by way of example only, and with reference to the accompanying drawings in which:

FIG. 12 shows a method of analysis that comprises building a classification library according to various embodiments;

FIG. 13 shows a method of analysis that comprises using a classification library according to various embodiments;

FIG. 16 shows on the left-hand side a case study of a patient suffering from Glioblastoma multiforme ("GBM") and shows a 3D image of the patient's brain which is overlayed by real time ultrasonic image and wherein an aerosol was generated by rapid evaporative ionisation mass spectrometry ("REIMS") from six sampling points (which are shown on the image) during surgery, wherein corresponding mass spectra which were recorded at each sampling point are shown (right bottom) together with a 3D PCA plot of all sampling point taken during the surgery and as labelled by a neuropathologist;

DETAILED DESCRIPTION

Figure 1:
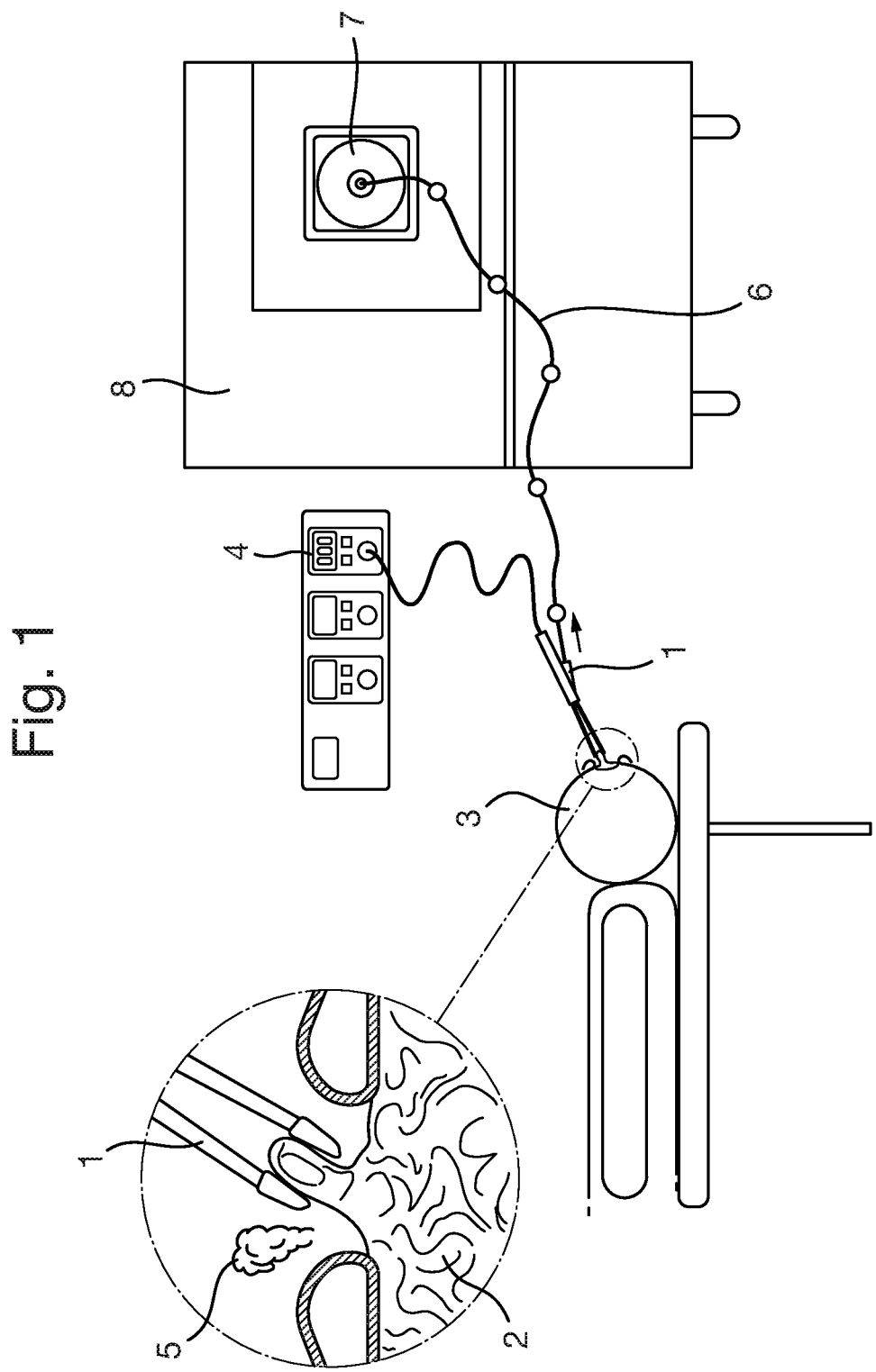
FIG. 1 illustrates a method of rapid evaporative ionisation mass spectrometry ("REIMS") wherein an RF voltage is applied to bipolar forceps resulting in the generation of an aerosol or surgical plume which is then captured through an irrigation port of the bipolar forceps and is then transferred to a mass spectrometer for mass analysis.

Various embodiments will now be described in more detail below which in general relate to obtaining chemical or other non-mass spectrometric data from one or more regions of a target (e.g., in vivo tissue) and then generating an aerosol, surgical smoke or vapour from one or more regions of the target using an ambient ionisation ion source.

The aerosol, surgical smoke or vapour is then aspirated into a vacuum chamber of a mass spectrometer and is caused to impact upon a collision surface causing the aerosol, smoke or vapour to be ionised by impact ionisation which results in the generation of analyte ions.

The resulting analyte ions (or fragment or product ions derived from the analyte ions) are then mass analysed and the resulting mass spectrometric data and/or ion mobility data may then be subjected to multivariate analysis in order to determine one or more properties of the target in real time.

For example, the multivariate analysis may enable a determination to be made as to whether or not a portion of tissue which is currently being resected is cancerous or not.

The use of chemical data enables tissue which is of potential concern to be identified either prior to and/or during a surgical procedure and enables a surgeon to have a greater confidence that all undesired or potentially cancerous tissue is both located and completely removed whilst at the same time ensuring that the minimum amount of healthy tissue is removed.

Ambient Ionisation Ion Sources

According to various embodiments a device is used to generate an aerosol, smoke or vapour from one or more regions of a target (e.g., in vivo tissue). The device may comprise an ambient ionisation ion source which is characterised by the ability to generate analyte aerosol, smoke or vapour from a native or unmodified target. For example, other types of ionisation ion sources such as Matrix Assisted Laser Desorption Ionisation ("MALDI") ion sources require a matrix or reagent to be added to the sample prior to ionisation.

It will be apparent that the requirement to add a matrix or a reagent to a sample prevents the ability to perform in vivo analysis of tissue and also, more generally, prevents the ability to provide a rapid simple analysis of target material.

In contrast, therefore, ambient ionisation techniques are particularly advantageous since firstly they do not require the addition of a matrix or a reagent (and hence are suitable for the analysis of in vivo tissue) and since secondly they enable a rapid simple analysis of target material to be performed.

A number of different ambient ionisation techniques are known and are intended to fall within the scope of the present invention. As a matter of historical record, Desorption Electrospray Ionisation ("DESI") was the first ambient ionisation technique to be developed and was disclosed in 2004. Since 2004, a number of other ambient ionisation techniques have been developed. These ambient ionisation techniques differ in their precise ionisation method but they share the same general capability of generating gas-phase ions directly from native (i.e. untreated or unmodified) samples. A particular advantage of the various ambient ionisation techniques which are intended to fall within the scope of the present invention is that the various ambient ionisation techniques do not require any prior sample preparation. As a result, the various ambient ionisation techniques enable both in vivo tissue and ex vivo tissue samples to be analysed without necessitating the time and expense of adding a matrix or reagent to the tissue sample or other target material.

A list of ambient ionisation techniques which are intended to fall within the scope of the present invention are given in the following table:

| Acronym | Ionisation technique |
|---|---|
| DESI | Desorption electrospray ionization |
| DeSSI | Desorption sonic spray ionization |
| DAPPI | Desorption atmospheric pressure photoionization |
| EASI | Easy ambient sonic-spray ionization |
| JeDI | Jet desorption electrospray ionization |
| TM-DESI | Transmission mode desorption electrospray ionization |
| LMJ-SSP | Liquid microjunction-surface sampling probe |
| DICE | Desorption ionization by charge exchange |
| Nano-DESI | Nanospray desorption electrospray ionization |
| EADESI | Electrode-assisted desorption electrospray ionization |
| APTDCI | Atmospheric pressure thermal desorption chemical ionization |
| V-EASI | Venturi easy ambient sonic-spray ionization |
| AFAI | Air flow-assisted ionization |
| LESA | Liquid extraction surface analysis |
| PTC-ESI | Pipette tip column electrospray ionization |
| AFADESI | Air flow-assisted desorption electrospray ionization |
| DEFFI | Desorption electro-flow focusing ionization |
| ESTASI | Electrostatic spray ionization |
| PASIT | Plasma-based ambient sampling ionization transmission |
| DAPCI | Desorption atmospheric pressure chemical ionization |

-continued

| Acronym | Ionisation technique |
| --- | --- |
| DART | Direct analysis in real time |
| ASAP | Atmospheric pressure solid analysis probe |
| APTDI | Atmospheric pressure thermal desorption ionization |
| PADI | Plasma assisted desorption ionization |
| DBDI | Dielectric barrier discharge ionization |
| FAPA | Flowing atmospheric pressure afterglow |
| HAPGDI | Helium atmospheric pressure glow discharge ionization |
| APGDDI | Atmospheric pressure glow discharge desorption ionization |
| LTP | Low temperature plasma |
| LS-APGD | Liquid sampling-atmospheric pressure glow discharge |
| MIPDI | Microwave induced plasma desorption ionization |
| MFGDP | Microfabricated glow discharge plasma |
| RoPPI | Robotic plasma probe ionization |
| PLASI | Plasma spray ionization |
| MALDESI | Matrix assisted laser desorption electrospray ionization |
| ELDI | Electrospray laser desorption ionization |
| LDTD | Laser diode thermal desorption |
| LAESI | Laser ablation electrospray ionization |
| CALDI | Charge assisted laser desorption ionization |
| LA-FAPA | Laser ablation flowing atmospheric pressure afterglow |
| LADESI | Laser assisted desorption electrospray ionization |
| LDESI | Laser desorption electrospray ionization |
| LEMS | Laser electrospray mass spectrometry |
| LSI | Laser spray ionization |
| IR-LAMICI | Infrared laser ablation metastable induced chemical ionization |
| LDSPI | Laser desorption spray post-ionization |
| PAMLDI | Plasma assisted multiwavelength laser desorption ionization |
| HALDI | High voltage-assisted laser desorption ionization |
| PALDI | Plasma assisted laser desorption ionization |
| ESSI | Extractive electrospray ionization |
| PESI | Probe electrospray ionization |
| ND-ESSI | Neutral desorption extractive electrospray ionization |
| PS | Paper spray |
| DIP-APCI | Direct inlet probe-atmospheric pressure chemical ionization |
| TS | Touch spray |
| Wooden-tip | Wooden-tip electrospray |
| CBS-SPME | Coated blade spray solid phase microextraction |
| TSI | Tissue spray ionization |
| RADIO | Radiofrequency acoustic desorption ionization |
| LIAD-ESI | Laser induced acoustic desorption electrospray ionization |
| SAWN | Surface acoustic wave nebulization |
| UASI | Ultrasonication-assisted spray ionization |
| SPA-nanoESI | Solid probe assisted nanoelectrospray ionization |
| PAUSI | Paper assisted ultrasonic spray ionization |
| DPESI | Direct probe electrospray ionization |
| ESA-Py | Electrospray assisted pyrolysis ionization |
| APPIS | Ambient pressure pyroelectric ion source |
| RASTIR | Remote analyte sampling transport and ionization relay |
| SACI | Surface activated chemical ionization |
| DEMI | Desorption electrospray metastable-induced ionization |
| REIMS | Rapid evaporative ionization mass spectrometry |
| SPAM | Single particle aerosol mass spectrometry |
| TDAMS | Thermal desorption-based ambient mass spectrometry |
| MAII | Matrix assisted inlet ionization |
| SAII | Solvent assisted inlet ionization |
| SwiFERR | Switched ferroelectric plasma ionizer |
| LPTD | Leidenfrost phenomenon assisted thermal desorption |

According to an embodiment the ambient ionisation ion source may comprise a rapid evaporative ionisation mass spectrometry ("REIMS") ion source wherein a RF voltage is applied to one or more electrodes in order to generate an aerosol or plume of surgical smoke by Joule heating.

However, it will be appreciated that other ambient ion sources including those referred to above may also be utilised. For example, according to another embodiment the ambient ionisation ion source may comprise a laser ionisation ion source. According to an embodiment the laser ionisation ion source may comprise a mid-IR laser ablation ion source. For example, there are several lasers which emit radiation close to or at 2.94 µm which corresponds with the peak in the water absorption spectrum. According to various embodiments the ambient ionisation ion source may comprise a laser ablation ion source having a wavelength close to 2.94 µm on the basis of the high absorption coefficient of water at 2.94 µm. According to an embodiment the laser ablation ion source may comprise a Er:YAG laser which emits radiation at 2.94 µm.

Other embodiments are contemplated wherein a mid-infrared optical parametric oscillator ("OPO") may be used to produce a laser ablation ion source having a longer wavelength than 2.94 µm. For example, an Er:YAG pumped ZGP-OPO may be used to produce laser radiation having a wavelength of e.g. 6.1 µm, 6.45 µm or 6.73 µm. In some situations it may be advantageous to use a laser ablation ion source having a shorter or longer wavelength than 2.94 µm since only the surface layers will be ablated and less thermal damage may result. According to an embodiment a $Co:MgF_2$ laser may be used as a laser ablation ion source wherein the laser may be tuned from 1.75-2.5 µm. According to another embodiment an optical parametric oscillator ("OPO") system pumped by a Nd:YAG laser may be used to produce a laser ablation ion source having a wavelength between 2.9-3.1 µm. According to another embodiment a $CO_2$ laser having a wavelength of 10.6 µm may be used to generate the aerosol, smoke or vapour.

According to other embodiments the ambient ionisation ion source may comprise an ultrasonic ablation ion source which generates a liquid sample which is then aspirated as an aerosol. The ultrasonic ablation ion source may comprise a focused or unfocussed source.

According to an embodiment the first device for generating aerosol, smoke or vapour from one or more regions of a target may comprise an electrosurgical tool which utilises a continuous RF waveform. According to other embodiments a radiofrequency tissue dissection system may be used which is arranged to supply pulsed plasma RF energy to a tool. The tool may comprise, for example, a PlasmaBlade®. Pulsed plasma RF tools operate at lower temperatures than conventional electrosurgical tools (e.g. 40-170° C. c.f. 200-350° C.) thereby reducing thermal injury depth. Pulsed waveforms and duty cycles may be used for both cut and coagulation modes of operation by inducing electrical plasma along the cutting edge(s) of a thin insulated electrode.

Rapid Evaporative Ionisation Mass Spectrometry ("REIMS")

FIG. 1 illustrates a method of rapid evaporative ionisation mass spectrometry ("REIMS") wherein bipolar forceps 1 may be brought into contact with in vivo tissue 2 of a patient 3. In the example shown in FIG. 1, the bipolar forceps 1 may be brought into contact with brain tissue 2 of a patient 3 during the course of a surgical operation on the patient's brain. An RF voltage from an RF voltage generator 4 may be applied to the bipolar forceps 1 which causes localised Joule or diathermy heating of the tissue 2. As a result, an aerosol or surgical plume 5 is generated. The aerosol or surgical plume 5 may then be captured or otherwise aspirated through an irrigation port of the bipolar forceps 1. The irrigation port of the bipolar forceps 1 is therefore reutilised as an aspiration port. The aerosol or surgical plume 5 may then be passed from the irrigation (aspiration) port of the bipolar forceps 1 to tubing 6 (e.g. ⅛" or 3.2 mm diameter Teflon® tubing). The tubing 6 is arranged to transfer the aerosol or surgical plume 5 to an atmospheric pressure interface 7 of a mass spectrometer 8 and/or ion mobility analyser.

According to various embodiments a matrix comprising an organic solvent such as isopropanol may be added to the aerosol or surgical plume 5 at the atmospheric pressure interface 7. The mixture of aerosol 3 and organic solvent may then be arranged to impact upon a collision surface within a vacuum chamber of the mass spectrometer and/or ion mobility analyser 8. According to one embodiment the collision surface may be heated. The aerosol is caused to ionise upon impacting the collision surface resulting in the generation of analyte ions. The ionisation efficiency of generating the analyte ions may be improved by the addition of the organic solvent. However, the addition of an organic solvent is not essential.

Analyte ions which are generated by causing the aerosol, smoke or vapour 5 to impact upon the collision surface are then passed through subsequent stages of the mass spectrometer (and/or ion mobility analyser) and are subjected to mass analysis in a mass analyser (and/or ion mobility analysis). The mass analyser may, for example, comprise a quadrupole mass analyser or a Time of Flight mass analyser.

Figure 2:
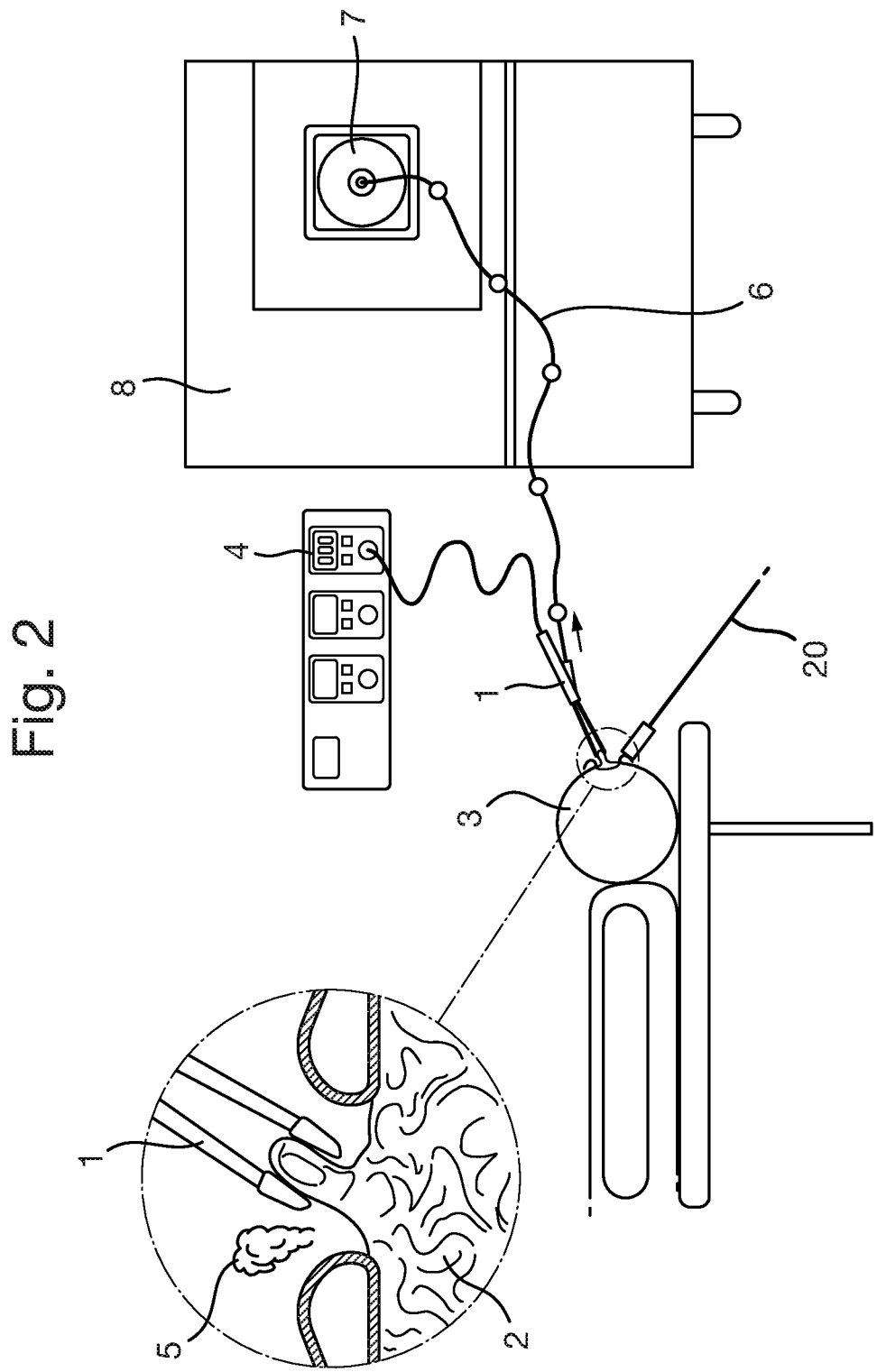
FIG. 2 illustrates a general embodiment wherein one or more chemical sensors are used to obtain chemical data from a target (e.g. in vivo tissue) prior to activating a rapid evaporative ionisation mass spectrometry ("REIMS") ion source to inter alia analyse the target and to determine, for example, whether or not the tissue is cancerous.

FIG. 2 illustrates a general embodiment wherein one or more chemical sensors 20 are used to obtain chemical data from a target 2 (e.g. in vivo tissue) prior to activating a rapid evaporative ionisation mass spectrometry ("REIMS") ion source 1 which inter alia samples tissue 2 and enables a determination to be made, for example, as to whether or not the issue is cancerous.

According to various embodiments the one or more sensor devices 20 may be used to obtain chemical (or other closely related) non-mass spectrometric data from the target (e.g. either in vivo or ex vivo biological tissue). The one or more chemical sensor devices 20 may be arranged, for example, to obtain from the target: (i) Raman spectroscopy data; (ii) chemical composition data; (iii) fluorescence data; (iv) absorption data; (v) reflectance data; (vi) transmission data; (vii) elastic scattering data; (viii) Fourier Transform Infra-Red Spectroscopy (FTIR) data; and (ix) interferometry data.

A number of different embodiments are contemplated and will be described in more detail below wherein chemical (or other closely related) data is acquired using one or more chemical sensors or devices 20 and wherein the chemical data may then be used, for example, to guide a user (e.g. a surgeon) performing a surgical, diagnostic or other procedure utilising an ambient ionisation ion source to one or more regions of particular interest on a target (e.g. in vivo or ex vivo tissue).

By way of example only, the one or more chemical sensors or devices 20 may be utilised to determine regions of tissue of a patient which have a different Raman spectroscopy, chemical composition, fluorescence, absorption, reflectance, transmission or elastic scattering profile compared to surrounding tissue. As will be appreciated, portions of tissue which have a different Raman spectroscopy, chemical composition, fluorescence, absorption, reflectance, transmission or elastic scattering profile compared to surrounding tissue may comprise diseased or potentially cancerous tissue. It is known, for example, that potentially cancerous tissue may be denser than healthy tissue and may have a highly vascular nature. Accordingly, potentially cancerous tissue may have a different water content to that of surrounding healthy tissue, may have a higher or different temperature to that of healthy tissue and have different chemical properties to that of surrounding healthy tissue.

According to an embodiment the additional or confirmatory information provided by the one or more chemical sensors 20 may be used to help determine the margins or bounds of healthy, potentially cancerous, cancerous, potentially diseased or diseased biological tissue or the margins or bounds of a tumour.

The cancerous biological tissue or the tumour may comprise grade I, grade II, grade III or grade IV cancerous tissue.

The one or more chemical sensors 20 may be used to help determine physical, chemical or other non-mass spectrometric data and in particular may be used to determine the margins or bounds between different types or grades of diseased or cancerous tissue.

The different grades of cancerous tissue may be selected from the group consisting of: (i) grade I cancerous tissue; (ii) grade II cancerous tissue; (iii) grade III cancerous tissue; and (iv) grade IV cancerous tissue.

According to various embodiments a determination from the chemical or other non-mass spectrometric data may be made to determine either: (i) one or more physical properties of the target; (ii) one or more chemical properties of the target; (iii) one or more physico-chemical properties of the target; or (iv) one or more mechanical properties of the target.

Optimised Operational Parameters of an Ambient Ionisation Surgical or Diagnostic Tool may be Programmed or Set Dependent upon Data Acquired from One or More Chemical Sensors According to an embodiment one or more operational parameters of an ambient ionisation surgical or diagnostic tool may be arranged to vary or otherwise be optimised during a surgical or diagnostic procedure based upon the acquired chemical data.

For example, according to an embodiment the energy dissipated into surrounding tissue may be arranged to reduce as the surgical or diagnostic device approaches a vital organ.

According to various embodiments one more operational parameters of an ambient ionisation ion source may be varied or controlled depending upon the specific type of tissue which is being probed. The type of tissue may be known in advance or may be determined from imaging, chemical, physical or other data. For example, according to an embodiment if a tissue or tumour has a soft or gelatinous texture or the probe is in close proximity to a sensitive region of the body (e.g. the probe is in close proximity to important nerves) than the power and/or duty cycle of the ambient ionisation ion source may be reduced, varied or otherwise altered.

According to another embodiment, one or more operational parameters of an ambient ionisation surgical or other tool may be set based upon the acquired chemical data. For example, one or more operational parameters of an ambient ionisation surgical tool may be set based upon the type or grade of cancerous tissue identified by the one or more chemical sensors or devices 20 or based upon the nature of the diseased tissue identified by the one or more chemical sensors or devices 20.

Different operational parameters may be used depending upon whether operating upon healthy tissue, clearly cancerous tissue or at the cancer margin.

According to various embodiments the chemical or other non-mass spectrometric data may include spatial information and hence the variation of tissue as a function of depth within an organ may be determined. Accordingly, previously acquired chemical data may be used to set various operational parameters of an ambient ionisation surgical tool as the surgical tool moves deeper into (or out of) an organ or closer to (or away from) an organ or specific tissue types.

Furthermore, various ionisation parameters may be varied as the ambient ionisation surgical tool moves deeper into (or out of) an organ or closer to (or away from) an organ or specific tissue types.

As the ambient ionisation surgical tool makes an initial cut into an organ one or more ionisation parameters (e.g. the composition of a matrix added to the aerosol, smoke or vapour released from the tissue, the temperature of a ionisation collision surface, the voltage applied to an ionisation collision surface etc.) may be optimised for the surgical conditions (e.g. initial blood loss, tissue composition) experienced when cutting into the organ. As the ambient ionisation surgical tool moves deeper into (or out of) the organ or closer to (or away from) an organ or specific tissue types the optimum ionisation parameters for the surgical tool may change reflecting e.g. a different degree of blood loss and a different composition of the tissue. Accordingly, one or more ionisation parameters (e.g. the composition of matrix added to aerosol, smoke or vapour released from the tissue, the temperature of a ionisation collision surface, the voltage applied to an ionisation collision surface etc.) may be arranged also to change or vary in order to match the changing surgical conditions and optionally based upon the acquired chemical data.

Numerous different embodiments are contemplated wherein various operational parameters of a surgical device or diagnostic tool which incorporates an ambient ionisation ion source (e.g. a rapid evaporative ionisation mass spectrometry ("REIMS") ion source) may be varied based upon the acquired chemical data.

According to various embodiments an ion mode of the mass spectrometer may be selected based upon chemical, physical, imaging or other data taken or determined from the cutting site.

According to further embodiments one or more operational parameters of the mass spectrometer may be changed or altered based upon, subsequent to or during the process of making a diagnosis (e.g. of cancerous or healthy tissue). For example, one or more operational parameters may be changed upon confirmation. The one or more operational parameters which may be changed or optimised depending upon the stage of analysis (e.g. exploratory, diagnosis or confirmation) include optimisation of: (i) inlet conditions including inlet voltages, type and flow rate of optional matrix added to aerosol flow, Venturi suction etc.; (ii) fragmentation conditions for aerosol including flow rates and temperature of collision surface, heated coil parameters etc.; (iii) downstream ion optics including ion path; and (iv) mass analysis steps including selection of mass peak(s) for further diagnosis, performing MS/MS experiments, fragmenting analyte ions of interest and mass analysing subsequent daughter, fragment or product ions.

Multivariate Analysis—Developing a Model for Classification

By way of example, a method of building a classification model using multivariate analysis of plural reference sample spectra will now be described.

Figure 3:
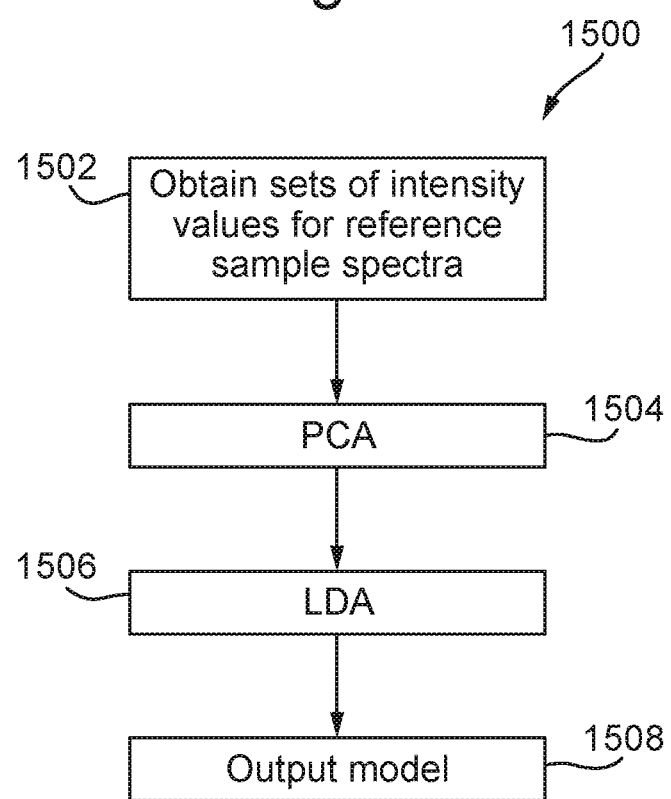
FIG. 3 shows a method of analysis that comprises building a classification model according to various embodiments.

FIG. 3 shows a method 1500 of building a classification model using multivariate analysis. In this example, the method comprises a step 1502 of obtaining plural sets of intensity values for reference sample spectra. The method then comprises a step 1504 of unsupervised principal component analysis (PCA) followed by a step 1506 of supervised linear discriminant analysis (LDA). This approach may be referred to herein as PCA-LDA. Other multivariate analysis approaches may be used, such as PCA-MMC. The PCA-LDA model is then output, for example to storage, in step 1508.

The multivariate analysis such as this can provide a classification model that allows an aerosol, smoke or vapour sample to be classified using one or more sample spectra obtained from the aerosol, smoke or vapour sample. The multivariate analysis will now be described in more detail with reference to a simple example.

Figure 4:
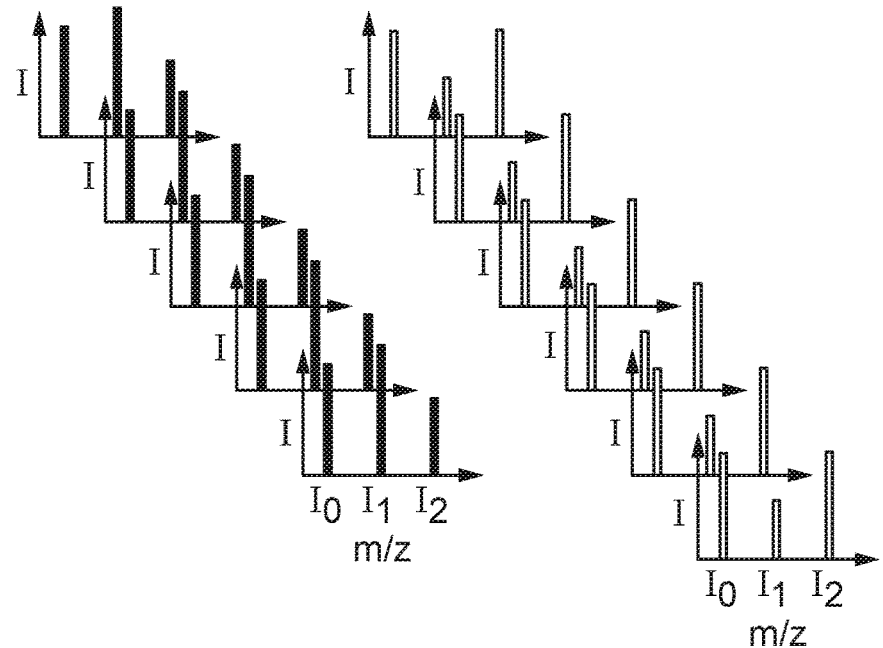
FIG. 4 shows a set of reference sample spectra obtained from two classes of known reference samples.

FIG. 4 shows a set of reference sample spectra obtained from two classes of known reference samples. The classes may be any one or more of the classes of target described herein. However, for simplicity, in this example the two classes will be referred as a left-hand class and a right-hand class.

Each of the reference sample spectra has been pre-processed in order to derive a set of three reference peak-intensity values for respective mass to charge ratios in that reference sample spectrum. Although only three reference peak-intensity values are shown, it will be appreciated that many more reference peak-intensity values (e.g., ~100 reference peak-intensity values) may be derived for a corresponding number of mass to charge ratios in each of the reference sample spectra. In other embodiments, the reference peak-intensity values may correspond to: masses; mass to charge ratios; ion mobilities (drift times); and/or operational parameters.

Figure 5:
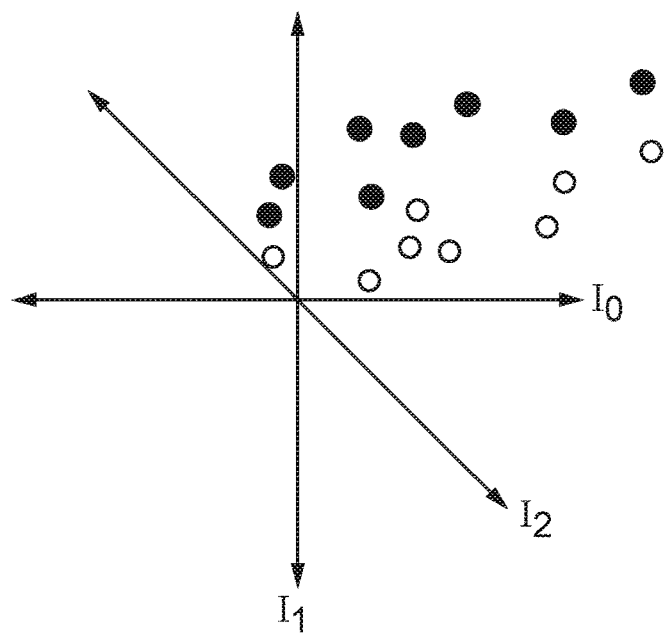
FIG. 5 shows a multivariate space having three dimensions defined by intensity axes, wherein the multivariate space comprises plural reference points, each reference point corresponding to a set of three peak intensity values derived from a reference sample spectrum.

FIG. 5 shows a multivariate space having three dimensions defined by intensity axes. Each of the dimensions or intensity axes corresponds to the peak-intensity at a particular mass to charge ratio. Again, it will be appreciated that there may be many more dimensions or intensity axes (e.g., ~100 dimensions or intensity axes) in the multivariate space. The multivariate space comprises plural reference points, with each reference point corresponding to a reference sample spectrum, i.e., the peak-intensity values of each reference sample spectrum provide the co-ordinates for the reference points in the multivariate space.

The set of reference sample spectra may be represented by a reference matrix D having rows associated with respective reference sample spectra, columns associated with respective mass to charge ratios, and the elements of the matrix being the peak-intensity values for the respective mass to charge ratios of the respective reference sample spectra.

In many cases, the large number of dimensions in the multivariate space and matrix D can make it difficult to group the reference sample spectra into classes. PCA may accordingly be carried out on the matrix D in order to calculate a PCA model that defines a PCA space having a reduced number of one or more dimensions defined by principal component axes. The principal components may be selected to be those that comprise or "explain" the largest variance in the matrix D and that cumulatively explain a threshold amount of the variance in the matrix D.

Figure 6:
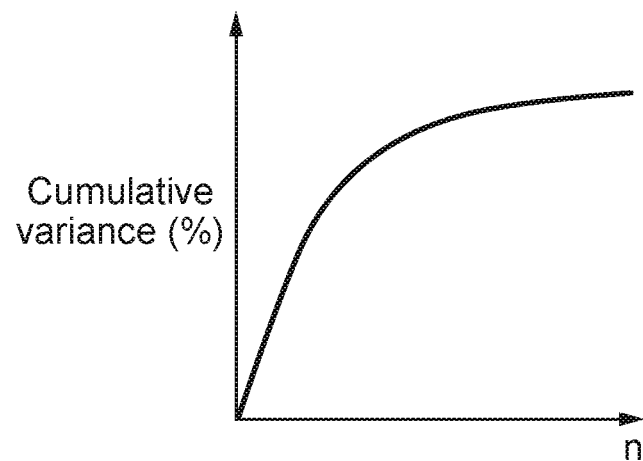
FIG. 6 shows a general relationship between cumulative variance and number of components of a PCA model.

FIG. 6 shows how the cumulative variance may increase as a function of the number n of principal components in the PCA model. The threshold amount of the variance may be selected as desired.

The PCA model may be calculated from the matrix D using a non-linear iterative partial least squares (NIPALS) algorithm or singular value decomposition, the details of which are known to the skilled person and so will not be described herein in detail. Other methods of calculating the PCA model may be used.

The resultant PCA model may be defined by a PCA scores matrix S and a PCA loadings matrix L. The PCA may also produce an error matrix E, which contains the variance not explained by the PCA model. The relationship between D, S, L and E may be:

$$D = SL^T + E \quad (1)$$

Figure 7:
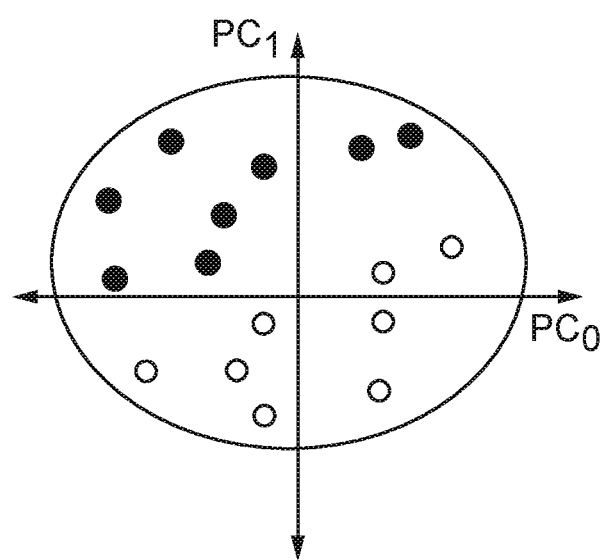
FIG. 7 shows a PCA space having two dimensions defined by principal component axes, wherein the PCA space comprises plural transformed reference points or scores, each transformed reference point or score corresponding to a reference point of FIG. 5.

FIG. 7 shows the resultant PCA space for the reference sample spectra of FIGS. 4 and 5. In this example, the PCA model has two principal components $PC_0$ and $PC_1$ and the PCA space therefore has two dimensions defined by two principal component axes. However, a lesser or greater number of principal components may be included in the PCA model as desired. It is generally desired that the number of principal components is at least one less than the number of dimensions in the multivariate space.

The PCA space comprises plural transformed reference points or PCA scores, with each transformed reference point or PCA score corresponding to a reference sample spectrum of FIG. 4 and therefore to a reference point of FIG. 5.

As is shown in FIG. 7, the reduced dimensionality of the PCA space makes it easier to group the reference sample spectra into the two classes. Any outliers may also be identified and removed from the classification model at this stage.

Further supervised multivariate analysis, such as multi-class LDA or maximum margin criteria (MMC), in the PCA space may then be performed so as to define classes and, optionally, further reduce the dimensionality.

As will be appreciated by the skilled person, multi-class LDA seeks to maximise the ratio of the variance between classes to the variance within classes (i.e., so as to give the largest possible distance between the most compact classes possible). The details of LDA are known to the skilled person and so will not be described herein in detail.

The resultant PCA-LDA model may be defined by a transformation matrix U, which may be derived from the PCA scores matrix S and class assignments for each of the transformed spectra contained therein by solving a generalised eigenvalue problem.

The transformation of the scores S from the original PCA space into the new LDA space may then be given by:

$$Z = SU \quad (2)$$

wherein the matrix Z contains the scores transformed into the LDA space.

Figure 8:
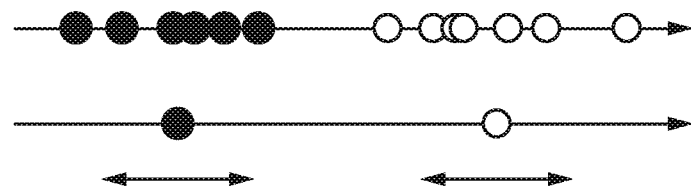
FIG. 8 shows a PCA-LDA space having a single dimension or axis, wherein the LDA is performed based on the PCA space of FIG. 7, the PCA-LDA space comprising plural further transformed reference points or class scores, each further transformed reference point or class score corresponding to a transformed reference point or score of FIG. 7.

FIG. 8 shows a PCA-LDA space having a single dimension or axis, wherein the LDA is performed in the PCA space of FIG. 7. As is shown in FIG. 8, the LDA space comprises plural further transformed reference points or PCA-LDA scores, with each further transformed reference point corresponding to a transformed reference point or PCA score of FIG. 7.

In this example, the further reduced dimensionality of the PCA-LDA space makes it even easier to group the reference sample spectra into the two classes. Each class in the PCA-LDA model may be defined by its transformed class average and covariance matrix or one or more hyperplanes (including points, lines, planes or higher order hyperplanes) or hypersurfaces or Voronoi cells in the PCA-LDA space.

The PCA loadings matrix L, the LDA matrix U and transformed class averages and covariance matrices or hyperplanes or hypersurfaces or Voronoi cells may be output to a database for later use in classifying an aerosol, smoke or vapour sample.

The transformed covariance matrix in the LDA space $V'_g$ for class g may be given by:

$$V'_g = U^T V_g U \quad (3)$$

wherein $V_g$ are the class covariance matrices in the PCA space.

The transformed class average position $z_g$ for class g may be given by:

$$s_g U = z_g \quad (4)$$

wherein $s_g$ is the class average position in the PCA space.

Multivariate Analysis—Using a Model for Classification

By way of example, a method of using a classification model to classify an aerosol, smoke or vapour sample will now be described.

Figure 9:
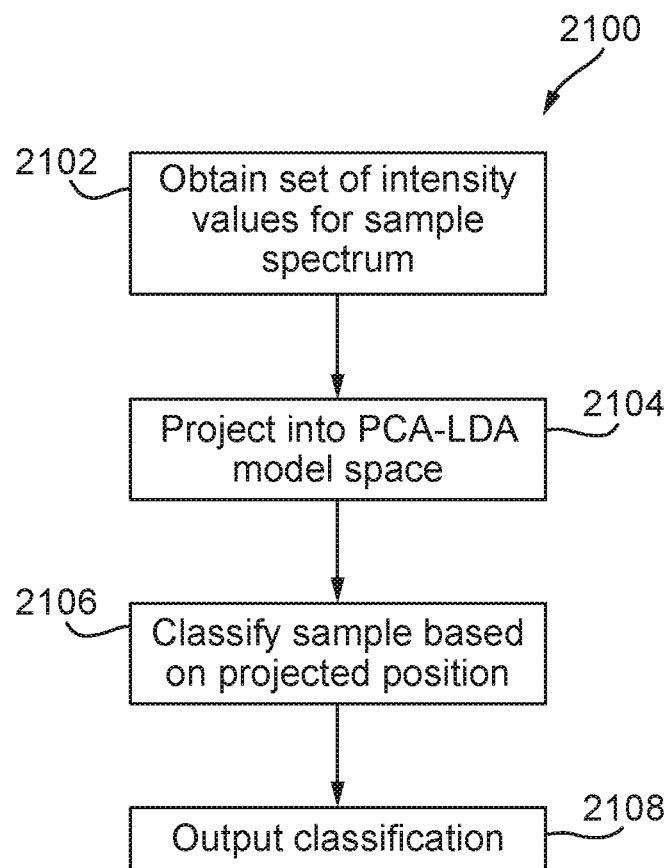
FIG. 9 shows a method of analysis that comprises using a classification model according to various embodiments.

FIG. 9 shows a method 2100 of using a classification model. In this example, the method comprises a step 2102 of obtaining a set of intensity values for a sample spectrum. The method then comprises a step 2104 of projecting the set of intensity values for the sample spectrum into PCA-LDA model space. Other classification model spaces may be used, such as PCA-MMC. The sample spectrum is then classified at step 2106 based on the project position and the classification is then output in step 2108.

Classification of an aerosol, smoke or vapour sample will now be described in more detail with reference to the simple PCA-LDA model described above.

Figure 10:
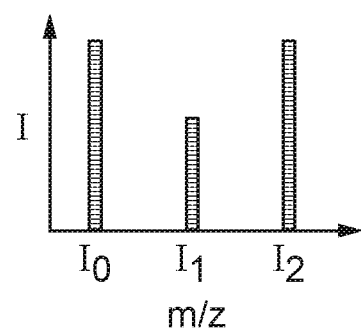
FIG. 10 shows a sample spectrum obtained from an unknown sample.

FIG. 10 shows a sample spectrum obtained from an unknown aerosol, smoke or vapour sample. The sample spectrum has been pre-processed in order to derive a set of three sample peak-intensity values for respective mass to charge ratios. As mentioned above, although only three sample peak-intensity values are shown, it will be appreciated that many more sample peak-intensity values (e.g., ~100 sample peak-intensity values) may be derived at many more corresponding mass to charge ratios for the sample spectrum. Also, as mentioned above, in other embodiments, the sample peak-intensity values may correspond to: masses; mass to charge ratios; ion mobilities (drift times); and/or operational parameters.

The sample spectrum may be represented by a sample vector $d_x$, with the elements of the vector being the peak-intensity values for the respective mass to charge ratios. A transformed PCA vector $s_x$ for the sample spectrum can be obtained as follows:

$$d_x L = s_x \quad (5)$$

Then, a transformed PCA-LDA vector $z_x$ for the sample spectrum can be obtained as follows:

$$s_x U = z_x \quad (6)$$

Figure 11:
FIG. 11 shows the PCA-LDA space of FIG. 8, wherein the PCA-LDA space further comprises a PCA-LDA projected sample point derived from the peak intensity values of the sample spectrum of FIG. 10.

FIG. 11 again shows the PCA-LDA space of FIG. 8. However, the PCA-LDA space of FIG. 11 further comprises the projected sample point, corresponding to the transformed PCA-LDA vector $z_x$, derived from the peak intensity values of the sample spectrum of FIG. 11.

In this example, the projected sample point is to one side of a hyperplane between the classes that relates to the right-hand class, and so the aerosol, smoke or vapour sample may be classified as belonging to the right-hand class.

Alternatively, the Mahalanobis distance from the class centres in the LDA space may be used, where the Mahalanobis distance of the point $z_x$ from the centre of class g may be given by the square root of:

$$(z_x-z_g)^T (V'_g)^{-1} (z_x-z_g) \tag{7}$$

and the data vector $d_x$ may be assigned to the class for which this distance is smallest.

In addition, treating each class as a multivariate Gaussian, a probability of membership of the data vector to each class may be calculated.

Library Based Analysis—Developing a Library for Classification

By way of example, a method of building a classification library using plural input reference sample spectra will now be described.

FIG. 12 shows a method 2400 of building a classification library. In this example, the method comprises a step 2402 of obtaining plural input reference sample spectra and a step 2404 of deriving metadata from the plural input reference sample spectra for each class of sample. The method then comprises a step 2406 of storing the metadata for each class of sample as a separate library entry. The classification library is then output, for example to electronic storage, in step 2408.

A classification library such as this allows an aerosol, smoke or vapour sample to be classified using one or more sample spectra obtained from the aerosol, smoke or vapour sample. The library based analysis will now be described in more detail with reference to an example.

In this example, each entry in the classification library is created from plural pre-processed reference sample spectra that are representative of a class. In this example, the reference sample spectra for a class are pre-processed according to the following procedure:

First, a re-binning process is performed. In this embodiment, the data are resampled onto a logarithmic grid with abscissae:

$$x_i = \left\lfloor N_{chan} \log \frac{m}{M_{min}} \bigg/ \log \frac{M_{max}}{M_{min}} \right\rfloor \tag{8}$$

wherein $N_{chan}$ is a selected value and denotes the nearest integer below x. In one example, $N_{chan}$ is $2^{12}$ or 4096.

Then, a background subtraction process is performed. In this embodiment, a cubic spline with k knots is then constructed such that p % of the data between each pair of knots lies below the curve. This curve is then subtracted from the data. In one example, k is 32. In one example, p is 5. A constant value corresponding to the q % quantile of the intensity subtracted data is then subtracted from each intensity. Positive and negative values are retained. In one example, q is 45.

Then, a normalisation process is performed. In this embodiment, the data are normalised to have mean $\bar{y}_i$. In one example, $\bar{y}_i=1$.

An entry in the library then consists of metadata in the form of a median spectrum value $\mu_i$ and a deviation value $D_i$ for each of the $N_{chan}$ points in the spectrum.

The likelihood for the i'th channel is given by:

$$Pr(y_i | \mu_i, D_i) = \frac{1}{D_i} \frac{C^{C-1/2} \Gamma(C)}{\sqrt{\pi}\, \Gamma(C-1/2)} \frac{1}{\left(C + \frac{(y_i - \mu_i)^2}{D_i^2}\right)^C} \tag{9}$$

where $\frac{1}{2} \leq C < \infty$ and where $\Gamma(C)$ is the gamma function.

The above equation is a generalised Cauchy distribution which reduces to a standard Cauchy distribution for C=1 and becomes a Gaussian (normal) distribution as C→∞. The parameter $D_i$ controls the width of the distribution (in the Gaussian limit $D_i = \sigma_i$ is simply the standard deviation) while the global value C controls the size of the tails.

In one example, C is 3/2, which lies between Cauchy and Gaussian, so that the likelihood becomes:

$$Pr(y_i | \mu_i, D_i) = \frac{3}{4} \frac{1}{D_i} \frac{1}{(3/2 + (y_i - \mu_i)^2 / D_i^2)^{3/2}} \tag{10}$$

For each library entry, the parameters $\mu_i$ are set to the median of the list of values in the i'th channel of the input reference sample spectra while the deviation $D_i$ is taken to be the interquartile range of these values divided by $\sqrt{2}$. This choice can ensure that the likelihood for the i'th channel has the same interquartile range as the input data, with the use of quantiles providing some protection against outlying data.

Library Based Analysis—Using a Library for Classification

By way of example, a method of using a classification library to classify an aerosol, smoke or vapour sample will now be described.

FIG. 13 shows a method 2500 of using a classification library. In this example, the method comprises a step 2502 of obtaining a set of plural sample spectra. The method then comprises a step 2504 of calculating a probability or classification score for the set of plural sample spectra for each class of sample using metadata for the class entry in the classification library. The sample spectra are then classified at step 2506 and the classification is then output in step 2508.

Classification of an aerosol, smoke or vapour sample will now be described in more detail with reference to the classification library described above.

In this example, an unknown sample spectrum y is the median spectrum of a set of plural sample spectra. Taking the median spectrum y can protect against outlying data on a channel by channel basis.

The likelihood $L_s$ for the input data given the library entry s is then given by:

$$L_s = Pr(y|\mu,D) = \Pi_{i=1}^{N_{chan}} Pr(y_i|\mu_i,D_i) \tag{11}$$

wherein $\mu_i$ and $D_i$ are, respectively, the library median values and deviation values for channel i. The likelihoods $L_s$ may be calculated as log likelihoods for numerical safety.

The likelihoods $L_s$ are then normalised over all candidate classes 's' to give probabilities, assuming a uniform prior probability over the classes. The resulting probability for the class $\tilde{s}$ is given by:

$$Pr(\tilde{s} | y) = \frac{L_{\tilde{s}}^{(1/F)}}{\Sigma_s L_s^{(1/F)}} \tag{12}$$

The exponent (1/F) can soften the probabilities which may otherwise be too definitive. In one example, F=100. These probabilities may be expressed as percentages, e.g., in a user interface.

Alternatively, RMS classification scores $R_s$ may be calculated using the same median sample values and derivation values from the library:

$$R_s(y, \mu, D) = \sqrt{\frac{1}{N_{chan}} \sum_{i=1}^{N_{chan}} \frac{(y_i - \mu_i)^2}{D_i^2}} \quad (13)$$

Again, the scores $R_s$ are normalised over all candidate classes 's'.

The aerosol, smoke or vapour sample may then be classified as belonging to the class having the highest probability and/or highest RMS classification score.

Raman Sampling System

Figure 14:
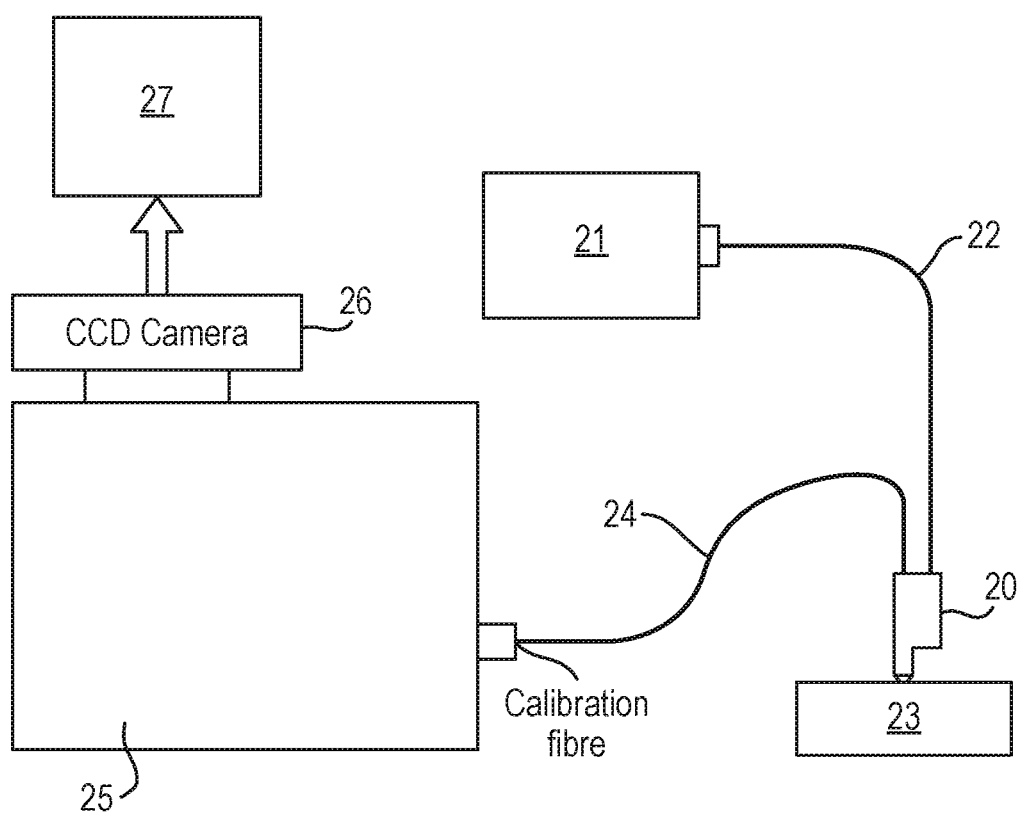
FIG. 14 shows a Raman sampling system according to an embodiment.

FIG. 14 shows a Raman sampling system according to an embodiment and comprises an excitation source 21, light delivery and collection optics 22,24, a spectrograph 25 and a detector 26.

The Raman sampling system as shown in FIG. 10 comprises a Raman probe 20 connected to a laser 21 (e.g. a diode laser 21) via a single optical delivery fibre 22. The delivery optical fibre 22 delivers laser light from the diode laser 21 to a target 23 (which may comprise in vivo biological tissue). Scattered light from the target 23 is collected by one or more collection optical fibres 24 which may comprise a bundle of optical fibres. The scattered light is passed by the one or more collection optical fibres 24 to a spectrograph 25. Raman spectra output from the spectrograph 25 is recorded or detected by a charge-coupled device ("CCD") camera or detector 26 and a signal is output to a computer 27. The spectrograph 25 may comprise one or more holographic optical elements to disperse the incident light onto a flat imaging plane that coincides with the detector 26. A CCD camera or detector 26 may be placed in the image plane of the spectrograph 25 to capture the dispersed light and the resulting image may be displayed by the computer 27.

Other embodiments are contemplated wherein the delivery fibre 22 may comprise a plurality of delivery fibres 22.

The spectrograph 25 may comprise a transmissive imaging spectrograph with a volume phase holographic grating and the CCD camera or detector 26 may according to an embodiment comprise a NIR optimised back-illumination deep-depletion CCD array. The CCD may have a 16 bit dynamic range and may be liquid nitrogen cooled to −120° C. The f-number of the spectrograph 25 (f=2.2) may be arranged to substantially match the numerical aperture (N.A.=0.22) of the one or more collection fibres 24.

Laser light sources are preferred for Raman spectroscopy due to their high power output and narrow bandwidth. For biological tissues a NIR laser may be used because of its deep penetration depth and the lower level of tissue autofluorescence under NIR excitation. 700-1000 μm may be regarded as an optical window for biological tissues.

According to various embodiments the laser 21 may be arranged to emit laser radiation at a wavelength of e.g. 632 nm, 690 nm, 785 nm, 810 nm, 830 nm or 1064 nm. It will be understood, however, that other embodiments are contemplated wherein the laser 21 may be arranged to emit laser radiation at other wavelengths. Shorter wavelengths may be used for ex vivo thin tissue samples. Both pulsed and continuous wave (CW) lasers may be used for Raman spectroscopy. For conventional Raman spectroscopy continuous wave lasers are most commonly used.

The laser diode 21 may comprise an external-cavity stabilised diode laser or a solid-state diode laser.

CCD detectors 26 are ideal for NIR Raman spectroscopy since they are linear, have a good dynamic range and have a high quantum efficiency in the NIR.

Raman spectroscopy utilises inelastically scattered laser light to provide detailed information about vibrations of molecular bonds. The Raman effect can be described as the inelastic scatter of light by the molecules of a sample. As a result, the energy of the scattered photons, and hence the wavelength, is different from that of the incident photons. These wavelength shifts are directly proportional to specific molecular vibrational modes. A Raman spectrum, which is a plot of intensity versus wavelength shift, provides information about the molecular constituents and microenvironment within a sample. Each chemical moiety in a sample has a unique molecular structure. Accordingly, the composition of a sample can be determined through analysis of a Raman spectrum.

A Raman spectrum is a plot of intensity versus wavelength shift. The wavelength shift is usually presented in units of relative wavenumbers ($cm^{-1}$). This is calculated for Stokes Raman scatter for light having an excitation wavelength $\lambda_{ex}$ and peak position $\lambda$ both in cm units:

$$\text{wavenumber} = \frac{1}{\lambda_{ex}} - \frac{1}{\lambda} \quad (14)$$

Relative wavenumbers are used so that spectra collected with different excitation wavelengths can be compared with each other.

One advantage of Raman spectroscopy is that a typical Rama spectrum will comprise relatively sharp peaks. This is in contrast to fluorescence spectroscopy where there are a limited number of fluorophores and the broad peaks make it harder to extract parameters from the unresolved spectral features. In fact, much of the structure of fluorescence spectra of biological tissue is due to the spectral contributions of oxyhemoglobin and deoxyhemoglobin rather than fluorescence.

Unlike infra-red absorption spectroscopy, water does not have an adverse effect on Raman spectra. Therefore, hydrated samples such as in vivo tissue may be studied and no sample preparation is required.

It can be shown from classical theory that the magnitude of the frequency shift is equal to the frequency of the participating molecular vibrational modes. Light scattered with decreased frequency, and hence a longer wavelength, is referred to as Stokes Raman scatter whilst the converse is referred to as anti-Stokes Raman scatter. At room temperature anti-Stokes Raman scatter is much weaker than Stokes Raman scatter.

Absorbed light will shift a molecule to an excited energy level. In the case of Rayleigh (elastic) scatter, light is absorbed, the molecule is excited from a ground state $n_0$ to a second excited level $n_2$, and then the molecule relaxes directly back from the second excited level $n_2$ to the ground state $n_0$ with a photon being emitted and without an exchange of energy.

Stokes Raman scatter occurs after absorption of an incident photon whereupon the molecule is excited from the ground state $n_0$ to the second excited level $n_2$ and then the molecule relaxes from the second excited level $n_2$ to an intermediate first vibrational energy level $n_1$ which is above the ground state $n_0$.

If the molecule is already in an intermediate first excited vibrational energy level $n_1$ then an incident photon may cause excitation up to the second excited energy level $n_2$ with subsequent relaxation down to the ground state $n_0$ resulting in anti-Stokes Raman scatter of the incident photon with reduced wavelength.

The delivery optical fibre 22 may terminate with a short wavelength pass or a bandpass (first) filter. The first filter may be arranged to transmit laser excitation light from the diode laser 21 but block longer wavelength spectral background from the delivery optical fibre 22. The delivery optical fibre 22 may be multi-mode and have a core diameter of 100-200 μm. The delivery optical fibre 22 may according to an embodiment have a numerical aperture in the range 0.22-0.37.

The delivery optical fibre 22 may comprise a high-hydroxide ("high-OH") fibre having a high UV and visible wavelength transmission. Alternatively, the delivery optical fibre 22 may comprise a low-hydroxide ("low-OH") fibre for use in the NIR and IR wavelength range.

The one or more collection optical fibres 24 may be preceded by a long wavelength pass or notch (second) filter. The second filter may be arranged to transmit a Raman spectrum from the target 23 (e.g., tissue) whilst blocking laser light which may be backscattered from the surface of the target 23.

According to various embodiments inline bandpass or long pass filters may be deposited on the optical fibre tips to reduce noise.

According to an embodiment excitation laser light emitted by the delivery optical fibre 22 may pass through a collimating lens, a bandpass filter (e.g. 785±2.5 nm) and a focusing lens. The bandpass filter effectively rejects Raman scattering and fluorescence which may have arisen from within the delivery optical fibre 22.

The intensity of the laser 21 may be controlled so that the irradiance at the target does not exceed a desired limit. For example, according to an embodiment the irradiance on the surface of skin (or other tissue) may be kept below 1.63 W/cm$^2$ for a 785 nm laser beam in accordance with ANSI Standard Z136.1-1993 (American National Standards Institute).

According to another embodiment the excitation laser light may have a wavelength of 830 nm and be generated by a diode laser 21. However, other embodiments are contemplated wherein other types of lasers may be used and the wavelength of the laser may be varied.

According to an embodiment backscattered Raman light may be collected using an f/1.2 camera lens having, for example, a focal length of 50 mm. The camera lens may be arranged to collimate the Raman light before the Raman light is notch filtered and then focused onto a f/4 spectrograph 25 via a lens for detection by the CCD camera or detector 26.

According to another embodiment the backscattered Raman light may be collected by a double lens arrangement wherein the first lens is for signal collection and beam collimation and the second lens is for focusing the signal into the collection optical fibres 24. The lenses may be arranged to have a focal length of 50 mm and to have a numerical aperture (NA) which substantially matches that of the collection optical fibre 24.

A longpass filter may be located between the first and second lenses. According to an embodiment the longpass filter may comprise an interference filter having a pass band 800-1200 nm. The longpass filter may be arranged to attenuate elastically scattered light whilst allowing passage of Raman scattered light.

The excitation light may be focused down to a spot size of approximately 100 μm diameter and the diameter of the collection fibre 24 may be approximately 1 mm.

The excitation optical fibre 22 and/or the collection optical fibre 24 may be fabricated from glass or from sapphire. Sapphire is of particular interest since it exhibits no fluorescence and only has a single sharp Raman band in normal regions of interest. Sapphire is also hard and durable.

According to an embodiment the Raman probe 20 may comprise a single central excitation fibre having e.g. a 200 μm diameter core which may be provided with an aluminium jacket for optical isolation so as to prevent cross talk with a plurality of collection fibres which may be arranged in a circular fashion around the central excitation fibre.

The collection fibres which may be arranged around the central excitation fibre may result in a probe having an overall diameter of 1.75 mm. The bundle of fibres may be encased in a black Teflon® coating for binding and protection and the Raman probe may have an overall length of approx. 4 m.

The Raman probe 20 may be provided in various different configurations. For example, according to an embodiment the Raman probe 20 may comprise a single ring of collection fibres 24 provided around a single central excitation fibre 22. Alternatively, according to another embodiment the Raman probe 20 may comprise a double ring of collection fibres 24 provided around a single central excitation fibre 22.

The single or double ring of collection fibres 24 may, for example, comprise 6, 7, 8, 9, 10, 11, 12, 13, 14, 15, 16, 17, 18, 19, 20 or >20 collection fibres.

According to another embodiment the collection optical fibres 24 may comprise a collection of 5-10, 10-20, 20-30, 30-40, 40-50, 50-60 or >60 low-OH fibres (100 μm core diameter).

The excitation laser may have a power of ~100 mW and the Raman probe 20 may be operated so that the one or more collection fibres 24 collect Raman light for a period of time of e.g. approx. 1 s, 2 s, 5 s, 10 s, 20 s, 30 s, 40 s, 50 s or 60 s.

The Raman probe 20 may be arrange to record Raman light having a wavenumber in the range of 800 to 1800 cm$^{-1}$. However, it will be understood by those skilled in the art that the range of 800 to 1800 cm$^{-1}$ should not be construed as being limiting. For example, according to other various embodiments Raman features or shifts in the range from 600 to 2000 cm$^{-1}$ may be determined.

According to various embodiments the Raman probe 20 may comprise an in vivo Raman spectroscopy system ("IVRS") and the Raman probe 20 may be used as part of an endoscopic tool.

For example, according to an embodiment the Raman probe 20 may be used as an in vivo endoscopic tool for obtaining Raman spectra from human gastrointestinal tissues. According to an embodiment the Raman probe 20 may utilise a 785 nm laser source and the laser light may be arranged to have a power of 100 mW. Raman spectra may be obtained during a collection time of e.g. 5 s.

According to an embodiment calcium fluoride ($CaF_2$) optical windows and other optical components may be used since $CaF_2$ has an excellent Raman window since it has a high transmission in the NIR, a low Raman scattering cross section which produces a single weak peak at 320 cm$^{-1}$ and a refractive index of ~1.4 which approximately matches the index of refraction of tissue.

Raman System Initialisation

The Raman system may be calibrated prior to clinical use. For example, the Raman system may be wavelength calibrated and the system spectral response may also be calibrated. The Raman signal may be subjected to intensity calibration and the CCD signal emitted from the CCD camera 26 may be processed to effect dark noise subtraction. The CCD dark noise may be measured before each measurement and may then be sequentially subtracted immediately after each CCD readout event.

Wavelength calibration may be performed using cyclohexane, acetone and barium sulfate in combination with an Hg—Ar lamp. A fifth order polynomial fitting may be used to correlate the CCD pixels with the wavelengths.

The computer 27 may be arranged to load databases and files needed for PCA and LDS analysis of the Raman spectra and/or associated mass spectra.

Various known algorithms may be applied to the obtained Raman spectra in order to remove any NIR autofluorescence background which may be superimposed upon the Raman signal.

Raman Spectroscopy and Analysis of Skin Cancer

Human skin may be analysed using non-invasive optical techniques including infrared (IR) spectroscopy and Raman spectroscopy. IR and Raman spectroscopy are similar in that they both probe the vibrational properties of molecules according to differing underlying physical principles. IR spectroscopy is based on the absorption properties of the sample tissue where the signal intensity follows Beer's law whereas Raman spectroscopy relies on detecting photons which are scattered inelastically by the sample tissue. The intensity of the Raman shift is directly proportional to molecular concentration and is independent of sample thickness.

It is known that Raman analysis of skin tissue results in prominent spectral features being observed in the range 800-1800 cm$^{-1}$ and in particular major vibrational bands around 855 cm$^{-1}$, 938 cm$^{-1}$, 1002 cm$^{-1}$, 1080 cm$^{-1}$, 1269 cm$^{-1}$, 1301 cm$^{-1}$, 1445 cm$^{-1}$, 1655 cm$^{-1}$ and 1745 cm$^{-1}$. The strongest band is located around 1445 cm$^{-1}$ and is assigned to the CH$_2$ deformations of proteins and lipids. The 1655 cm$^{-1}$ and 1269 cm$^{-1}$ bands are assigned to protein vibrational modes involving amide I and amide III.

It is also known that Raman analysis of skin shows major Raman peaks around 851 cm$^{-1}$, 962 cm$^{-1}$, 1065 cm$^{-1}$, 1258 cm$^{-1}$, 1297 cm$^{-1}$, 1437 cm$^{-1}$, 1542 cm$^{-1}$, 1653 cm$^{-1}$, 1737 cm$^{-1}$, 2159 cm$^{-1}$, 2698 cm$^{-1}$, 2828 cm$^{-1}$, 2879 cm$^{-1}$ and 2987 cm$^{-1}$.

Basal cell carcinoma ("BCC") originates in the kertatinocytes of the epidermis. It is known that NIR Raman spectra of basal cell carcinoma tissue samples show an intensity decrease of the amide III region at 1230-1290 cm$^{-1}$ relative to the lipid region at 1290-1330 cm$^{-1}$. A decrease in intensity may also be observed at the amino acid region of 830-900 cm$^{-1}$ and 900-990 cm$^{-1}$. In particular, the following spectral regions have been found to differ with pathology: 900-984 cm$^{-1}$ (amino acids), 1290-1350 cm$^{-1}$ (lipids), 1600-1725 cm$^{-1}$ (amide I) and 2800-3000 cm$^{-1}$ (C—H region).

Raman spectra of skin tissue exhibit collagen features from the dermis due to proline and hydroxyproline side chain peaks at 855 cm$^{-1}$ and 936 cm$^{-1}$.

It is apparent, therefore, that Raman spectra may be used to help identify potentially cancerous skin tissue in combination with analysis using an ambient ionisation ion source.

Raman Spectroscopy and Analysis of Gynaecological Cancer

It is known that the relative intensities of peaks around 1262 cm$^{-1}$ (amide III), 1445 cm$^{-1}$ (CH bend) and 1659 cm$^{-1}$ (amide I) may be used to classify normal and malignant gynaecological tissue.

For uterine and cervical cancers the intensity of a peak around 1657 cm$^{-1}$ may be reduced relative to the 1445 cm$^{-1}$ band possibly due to changes in the protein-lipoprotein composition of the tissue.

A broadening of the amide III band for uterine, endometrial and ovarian cancers is also observed and may be indicative of a degradation in the elastin content.

It is apparent, therefore, that Raman spectra may be used to help identify potentially cancerous or diseased gynaecological tissue in combination with analysis using an ambient ionisation ion source.

Ultraviolet Resonance Raman Spectroscopy ("UVRRS")

Ultraviolet resonance Raman spectroscopy ("UVRRS") relates to a variant of Raman spectroscopy wherein when the excitation wavelength matches an absorption band of the sample then the intensity of the Raman signal is increased by several orders of magnitude. As a result, the signal to noise ratio is dramatically increased and tissue fluorescence may also be circumvented.

Embodiments are contemplated wherein ultraviolet resonance Raman spectroscopy data may be acquired and used to help identify potentially cancerous or diseased tissue in combination with analysis using an ambient ionisation ion source.

Raman Spectroscopy and Analysis of Breast Tissue

Breast tissue is an excellent candidate for Raman spectroscopy since it has a high concentration of fatty acids which produces a strong Raman scatter and results in spectra which have an excellent signal to noise ratio ("SNR").

It has been shown, for example, that it is possible to use Raman spectroscopy to detect silicone (polydimethylsiloxane gel) in lymph nodes due, for example, to leakage of breast implants with subsequent leakage and contamination of the lymph nodes.

Embodiments are contemplated wherein Raman spectroscopy data may be acquired and used to help identify potentially cancerous, diseased or contaminated breast tissue in combination with analysis using an ambient ionisation ion source.

Raman Spectroscopy and Analysis of Formalin Fixed Tissues

Raman spectroscopy may be used to analyse both formalin and paraffin-fixed tissue samples. Fixing a tissue sample with formalin introduces spectral contamination of an additional band around 1040 cm$^{-1}$.

Raman spectroscopy may also be performed on tissue samples which have been stored frozen. Tissue samples may be freeze stored at −85° C. in optimal-cutting temperature ("OCT") media. Prior to analysis by Raman spectroscopy, the tissues should be pre-thawed at room temperature for 15 min, removed from the OCT and immersed in phosphate buffered saline ("PBS") for an additional 15 minutes. Raman spectroscopy may then be performed on the sample immersed in PBS.

Embodiments are therefore contemplated wherein Raman spectroscopy data may be acquired and used to help analyse ex vivo tissue including formalin fixed and frozen fixed tissue in combination with analysis using an ambient ionisation ion source.

Raman Spectroscopy and Analysis of Bone and Skull

Bone consists of hydrated inorganic extracellular matrices of carbonated calcium phosphates that are rich in collagen. The organic component also includes small amounts of glycosaminoglycans, glycoproteins, lipids and peptides. Conventional X-ray diffraction analysis of bone has a number of drawbacks whereas Raman spectroscopy may be used to obtain data both from the organic and inorganic components of bone.

Characteristic Raman peaks of skull are observed at around 800 $cm^{-1}$, 851 $cm^{-1}$, 950 $cm^{-1}$, 1065 $cm^{-1}$, 1335 $cm^{-1}$, 1442 $cm^{-1}$, 1542 $cm^{-1}$, 1653 $cm^{-1}$, 1725 $cm^{-1}$, 2139 $cm^{-1}$ and 2917 $cm^{-1}$.

Both skull and teeth have a strong Raman peak around 950 $cm^{-1}$ coming from calcium hydroxylapatite.

Embodiments are contemplated wherein Raman spectroscopy data may be acquired and used to help analyse bone and skull in combination with analysis using an ambient ionisation ion source.

According to various embodiments biological tissue or portions of bone or skull may be irradiated using a laser in order to generate an aerosol or surgical smoke. The aerosol or surgical smoke may then be analysed using laser induced breakdown spectroscopy ("LIBS").

Raman Spectroscopy and Analysis of Teeth

The major hard component of teeth is dentine which bound by cementum at the root and a thin layer of enamel at the exposed crown. These materials are composed of approximately 70% inorganic apatite within an organic matrix that is predominantly collagen I. Smaller concentrations of protein, lipids and peptides are also present. Enamel, the hardest tissue in the human body, has the lowest concentration of organic matter and does not contain collagen.

NIR Raman spectroscopy can provide information about both the mineral and organic components of teeth.

Characteristic Raman peaks of teeth are observed around 800 $cm^{-1}$, 851 $cm^{-1}$, 950 $cm^{-1}$, 1065 $cm^{-1}$, 1335 $cm^{-1}$, 1442 $cm^{-1}$, 1542 $cm^{-1}$, 1653 $cm^{-1}$, 1725 $cm^{-1}$, 2139 $cm^{-1}$ and 2917 $cm^{-1}$.

Both skull and teeth have a strong Raman peak around 950 $cm^{-1}$ coming from calcium hydroxylapatite.

Embodiments are contemplated wherein Raman spectroscopy data may be acquired and used to help analyse teeth in combination with analysis using an ambient ionisation ion source.

According to various embodiments biological tissue or portions of teeth may be irradiated using a laser in order to generate an aerosol or surgical smoke. The aerosol or surgical smoke may then be analysed using laser induced breakdown spectroscopy ("LIBS").

Raman Spectroscopy and Analysis of Blood, Blood Pellets and Serum

Raman spectra generated from blood and blood pellets are near identical and suggest that the observed spectral features are due mainly to red blood cells. Major Raman peaks are observed around 742 $cm^{-1}$, 778 $cm^{-1}$, 991 $cm^{-1}$, 1074 $cm^{-1}$, 1120 $cm^{-1}$, 1160 $cm^{-1}$, 1210 $cm^{-1}$, 1335 $cm^{-1}$, 1383 $cm^{-1}$, 1442 $cm^{-1}$, 1542 $cm^{-1}$, 1614 $cm^{-1}$, 2159 $cm^{-1}$ and 2914 $cm^{-1}$. Highly oxygenated blood also shows additional peaks around 1375 $cm^{-1}$, 1590 $cm^{-1}$ and 1640 $cm^{-1}$.

Serum exhibits major Raman peaks around 820 $cm^{-1}$, 1044 $cm^{-1}$, 1335 $cm^{-1}$, 1383 $cm^{-1}$, 1442 $cm^{-1}$, 1542 $cm^{-1}$, 1614 $cm^{-1}$, 1653 $cm^{-1}$, 2159 $cm^{-1}$, 2646 $cm^{-1}$ and 2914 $cm^{-1}$.

Embodiments are contemplated wherein Raman spectroscopy data may be acquired and used to help analyse blood, blood pellets and serum in combination with analysis using an ambient ionisation ion source.

Raman Spectroscopy and Analysis of Adipose Tissue and Fatty Acids

Adipose tissue is loose connective tissue composed of adipocytes and its main role is to store energy in the form of fat. Adipose tissue exhibits characteristic Raman peaks around 1065 $cm^{-1}$, 1270 $cm^{-1}$, 1298 $cm^{-1}$, 1437 $cm^{-1}$ and 1650 $cm^{-1}$ in the low frequency region and peaks around 2828 $cm^{-1}$, 2879 $cm^{-1}$ and 2970 $cm^{-1}$ in the high frequency region.

Palmitic acid is one of the most common saturated fatty acids found in animals and plants and occurs mainly as its ester in triglycerides (fats). All saturated fatty acids including lauric acid, myristic acid, palmitic acid and stearic acid have similar Raman spectra with strong peaks around 1063 $cm^{-1}$, 1128 $cm^{-1}$, 1296 $cm^{-1}$ and 1438 $cm^{-1}$.

Embodiments are contemplated wherein Raman spectroscopy data may be acquired and used to help analyse adipose tissue and fatty acids in combination with analysis using an ambient ionisation ion source.

Raman Spectroscopy and Analysis of Skeletal Muscles

Skeletal muscles comprise contractile tissue and the characteristic Raman peaks of skeletal muscles are located around 851 $cm^{-1}$, 962 $cm^{-1}$, 1065 $cm^{-1}$, 1258 $cm^{-1}$, 1297 $cm^{-1}$, 1437 $cm^{-1}$, 1542 $cm^{-1}$, 1653 $cm^{-1}$ and 1737 $cm^{-1}$ in the low frequency region and around 2159 $cm^{-1}$, 2698 $cm^{-1}$, 2828 $cm^{-1}$, 2914 $cm^{-1}$ and 2987 $cm^{-1}$ in the high frequency region.

Embodiments are contemplated wherein Raman spectroscopy data may be acquired and used to help analyse skeletal muscles in combination with analysis using an ambient ionisation ion source.

Raman Spectroscopy and Analysis of Brain Disease

Raman spectroscopy has been used to study both normal and diseased brain tissue. Brain tissue comprises approximately 70% protein, 12% lipid and 3-5% nucleic acid by dry weight and provides a strong Raman signal with NIR excitation.

Parkinson's disease is a progressive neurological disorder which results from the degeneration of the substantia nigra ("SN") in the basal ganglia.

Glioblastoma multiforme ("GBM"), which originate from glial cells, are the most severe malignant brain tumours due to their invasive nature and high morbidity. Diagnosis and grading is dependent upon the tumour origin, mitotic activity and endothelial proliferation. Conventional grading of brain tumours relies on biopsies which carries a risk of bleeding and subsequent brain damage.

Embodiments are contemplated wherein Raman spectroscopy data may be acquired and used to help analyse brain disease in combination with analysis using an ambient ionisation ion source.

Raman Spectroscopy and Analysis of Gastrointestinal (GI) Tract Diseases and Disorders Barrett's esophagus ("BE") is a premalignant condition where normal squamous spithelium (SQ) lining is replaced with glandular columnar epthelium. Patients with BE have an increased risk of developing esophageal adenocarcinoma (AC). Dysplasia (DYS), defined as unequivocal neoplastic epithelium, is an important marker for an increased risk of malignancy.

Characteristic Raman peaks of normal stomach tissue are observed around 828 $cm^{-1}$, 851 $cm^{-1}$, 991 $cm^{-1}$, 1044 $cm^{-1}$, 1258 $cm^{-1}$, 1302 $cm^{-1}$, 1442 $cm^{-1}$, 1653 $cm^{-1}$, 1725 $cm^{-1}$, 2139 $cm^{-1}$, 2177 $cm^{-1}$ and 2917 $cm^{-1}$.

Characteristic Raman peaks of normal small intestine tissue are observed around 828 $cm^{-1}$, 921 $cm^{-1}$, 991 $cm^{-1}$, 1044 $cm^{-1}$, 1258 $cm^{-1}$, 1074 $cm^{-1}$, 1160 $cm^{-1}$, 1258 $cm^{-1}$, 1302 $cm^{-1}$, 1335 $cm^{-1}$, 1442 $cm^{-1}$, 1542 $cm^{-1}$, 1653 $cm^{-1}$, 1725 $cm^{-1}$, 2139 $cm^{-1}$, 2177 $cm^{-1}$, 2870 $cm^{-1}$ and 2917 $cm^{-1}$.

Characteristic Raman peaks of normal colorectal tissue are observed around 1080 $cm^{-1}$, 1260 $cm^{-1}$, 1300 $cm^{-1}$, 1450 $cm^{-1}$, 1650 $cm^{-1}$ and 1750 $cm^{-1}$.

Characteristic Raman peaks of normal bladder tissue are observed around 828 $cm^{-1}$, 921 $cm^{-1}$, 1044 $cm^{-1}$, 1442 $cm^{-1}$, 1653 $cm^{-1}$, 1725 $cm^{-1}$, 2139 $cm^{-1}$ and 2917 $cm^{-1}$.

Embodiments are contemplated wherein Raman spectroscopy data may be acquired and used to help analyse gastrointestinal (GI) tract diseases and disorders in combination with analysis using an ambient ionisation ion source.

According to various embodiments biological tissue or portions of gastrointestinal tract may be irradiated using a laser or a rapid evaporative ionisation mass spectrometry ("REIMS") ionisation source in order to generate an aerosol or surgical smoke.

Raman Spectroscopy and Analysis of Lung Tissue

Characteristic Raman peaks of lung tissue are observed around 800 $cm^{-1}$, 991 $cm^{-1}$, 1044 $cm^{-1}$, 1302 $cm^{-1}$, 1335 $cm^{-1}$, 1442 $cm^{-1}$, 1542 $cm^{-1}$, 1590 $cm^{-1}$, 1614 $cm^{-1}$, 1653 $cm^{-1}$, 1725 $cm^{-1}$, 2139 $cm^{-1}$ and 2917 $cm^{-1}$. Lung tissue has a special characteristic peak at 1590 $cm^{-1}$.

Embodiments are contemplated wherein Raman spectroscopy data may be acquired and used to help analyse lung tissue diseases in combination with analysis using an ambient ionisation ion source.

Raman Spectroscopy and Analysis of Colorectal Cancers

Colorectal cancers following a similar progression of disease to that of gastrointestinal cancers and begins with dysplasia. Subtle changes in the bands around 1340 $cm^{-1}$, 1458 $cm^{-1}$, 1576 $cm^{-1}$ and 1662 $cm^{-1}$ are indicative of an increase in both the nucleic acid and lipid content for adenocarcinoma.

Embodiments are contemplated wherein Raman spectroscopy data may be acquired and used to help analyse colorectal cancers in combination with analysis using an ambient ionisation ion source.

Raman Spectroscopy and Analysis of Kidney, Liver and Spleen Tissue

Characteristic Raman peaks of kidney tissue are observed around 876 $cm^{-1}$, 1031 $cm^{-1}$, 1335 $cm^{-1}$, 1442 $cm^{-1}$, 1542 $cm^{-1}$, 1623 $cm^{-1}$, 1653 $cm^{-1}$, 1725 $cm^{-1}$, 2127 $cm^{-1}$, 2159 $cm^{-1}$ and 2914 $cm^{-1}$.

Characteristic Raman peaks of liver tissue are observed around 851 $cm^{-1}$, 1044 $cm^{-1}$, 1335 $cm^{-1}$, 1442 $cm^{-1}$, 1542 $cm^{-1}$, 1585 $cm^{-1}$, 1623 $cm^{-1}$, 1653 $cm^{-1}$, 1725 $cm^{-1}$, 2159 $cm^{-1}$, 2870 $cm^{-1}$ and 2914 $cm^{-1}$.

Characteristic Raman peaks of spleen tissue are observed around 828 $cm^{-1}$, 1017 $cm^{-1}$, 1442 $cm^{-1}$, 1542 $cm^{-1}$, 1623 $cm^{-1}$, 1725 $cm^{-1}$, 2127 $cm^{-1}$, 2151 $cm^{-1}$, 2747 $cm^{-1}$ and 2914 $cm^{-1}$.

Embodiments are contemplated wherein Raman spectroscopy data may be acquired and used to help analyse kidney, liver and spleen tissue in combination with analysis using an ambient ionisation ion source.

Brain Tumours

The brain is the centre of the nervous system and comprises two broad classes of cells namely neurons and glia.

Brain tissue has characteristic Raman peaks around 962 $cm^{-1}$, 991 $cm^{-1}$, 1044 $cm^{-1}$, 1302 $cm^{-1}$, 1442 $cm^{-1}$, 1542 $cm^{-1}$, 1614 $cm^{-1}$, 1653 $cm^{-1}$, 1725 $cm^{-1}$, 2139 $cm^{-1}$, 2879 $cm^{-1}$ and 2917 $cm^{-1}$. Brain tissue has a strong lipid peak around 2879 $cm^{-1}$.

Brain tumours have been induced in mice by injecting a suspension of the D-54MG malignant human glioma cell line into severe compromised immune deficient (scid) mice. Possible glioma markers were identified by Raman spectroscopy at around 1158 $cm^{-1}$, 1362 $cm^{-1}$, 1390 $cm^{-1}$ and 1550 $cm^{-1}$.

Human brain tumours have also been studied using Raman spectroscopy. It has been observed that the amide III band shifts from 1245 to 1268 $cm^{-1}$ in glioma grade III brain tumours which is indicative of a change from α-helix to random coil secondary protein structure. The tumours also have an enhanced peak at 1130 $cm^{-1}$ (C—C stretch) due to the trans configuration of the lipid hydrocarbon chains which suggested a loss of fluidity of these lipids which was also reflected in the lipid peaks of the CH stretching region at 2800-2950 $cm^{-1}$. It has also been observed that the polysaccharide peak at 856 $cm^{-1}$ is enhanced for tumours and may be used to monitor tumour development.

Embodiments are contemplated wherein Raman spectroscopy data may be acquired and used to help analyse brain tumours in combination with analysis using an ambient ionisation ion source.

Raman Spectroscopy and Analysis of Arteries and Heart Tissue

Heart attacks, which result mostly from coronary atherosclerosis, account for approximately 20-25% of all deaths in the United States. Arteries are composed of three layers namely the intima, media and adventitia. Atherosclerosis occurs when the intima thickens due an increase in the collagen content. This results in the build up of fats and necrotic tissue, which if left unchecked, results in the formation of plaques. Subsequent accumulations of calcium may result in calcium hydroxyapatite deposits in the artery wall which may further occlude blood flow and result in conditions such as heart disease.

Normal aorta are dominated by protein peaks at 1252 $cm^{-1}$, 1452 $cm^{-1}$ and 1658 $cm^{-1}$. Raman spectra of atheromatous plaques exhibit many peaks below 1000 $cm^{-1}$ which are attributed to cholesterol. Peaks are also observed at 630 $cm^{-1}$ and 1070 $cm^{-1}$ which correlate with calcium hydroxyapatite and carbonate apatites respectively.

Atherosclerotic aorta has been observed to comprise 47% total cholesterol (c.f. 6% for normal tissue).

Characteristic Raman peaks of heart tissue are observed around 962 $cm^{-1}$, 1031 $cm^{-1}$, 1302 $cm^{-1}$, 1335 $cm^{-1}$, 1442 $cm^{-1}$, 1542 $cm^{-1}$, 1623 $cm^{-1}$, 1653 $cm^{-1}$, 1725 $cm^{-1}$, 2127 $cm^{-1}$, 2159 $cm^{-1}$, 2870 $cm^{-1}$ and 2914 $cm^{-1}$.

Embodiments are contemplated wherein Raman spectroscopy data may be acquired and used to help analyse arteries and heart tissue in combination with analysis using an ambient ionisation ion source.

Raman Spectroscopy and Analysis of Organs

Main Raman peaks coming from proteins, lipids and DNS appear in similar positions of Raman spectra of all tissues because all tissues have protein molecules, phospholipids, DNA and RNA. Raman peaks around 1270 $cm^{-1}$, 1310 $cm^{-1}$, 1445 $cm^{-1}$, 1660 $cm^{-1}$ and 2900 $cm^{-1}$ originate from lipids and proteins and are clearly observed in every organ.

Embodiments are contemplated wherein Raman spectroscopy data may be acquired and used to help analyse organ tissue in combination with analysis using an ambient ionisation ion source.

Fluorescence Background Tissue

Autofluorescence background can influence the measurement of Raman spectra from organs. The main fluorophores in biological tissue are pyridinic (NADPH) and flavin coenzymes (FAD), collagen and elastin.

Contrast Agents and Nanoparticles

The near-infrared ("NIR") may be used to interrogate tissues in combination with NIR excitable dyes or contrast agents.

Various embodiments are contemplated wherein endogenous or exogenous contrast agents may be used to enhance image data, physical data, chemical data or other data which may be acquired according to various embodiments.

A number of different contrast agents may be used to enhance image data, physical data, chemical data or other data which, for example, may fluorescence when illuminated with infrared radiation having a wavelength in the range 700-900 nm. The wavelength range 700-900 nm may be considered to comprise a therapeutic window since in vivo tissue exhibits a low absorbance in this wavelength range. Absorption occurs primarily from tissue chromophores of oxy- and deoxyhemoglobin, fat, melanin and water.

It will be understood that the ability to detect potentially abnormal or diseased tissue by imaging, chemical, physical or other techniques depends principally upon there being a contrast between healthy and diseased tissue.

Alternatively, abnormal or diseased tissue can be differentiated from healthy tissue on the basis of the two different tissue types having different scattering properties.

Although the wavelength range 700-900 nm is of particular interest due to the low absorbance in this wavelength range, infrared radiation in this wavelength range can also exhibit a relatively high scattering coefficient.

Embodiments are contemplated wherein imaging data, chemical data, physical data or other data may be obtained by detecting differences in the scattering of infrared radiation within the wavelength range 700-900 nm between healthy and diseased tissue.

Embodiments are also contemplated wherein one or more exogenous contrast agents may be used to analyse in vivo, ex vivo or in vitro tissue samples, biological matter, organic matter (including plastics), one or more bacterial colonies or one or more fungal colonies. According to an embodiment one or more exogenous fluorescence contrast agents may be provided or added to the tissue in order to augment endogenous contrast.

The one or more contrast agents may comprise one or more fluorescent contrast agents.

The one or more contrast agents may comprise one or more visible dyes.

The one or more contrast agents may comprise one or more radiocontrast agents.

The one or more contrast agents may comprise one or more optical, near infrared ("NIR"), fluorescent, autofluorescent or diagnostic contrast agents.

According to various embodiments the one or more contrast agents may be selected from the group consisting of: (i) indocyanine green ("ICG") and derivatives or conjugates of indocyanine green including indotricarbocyanine; (ii) diethylthiatricarbocyanine iodide ("DTTCI") and derivatives or conjugates of diethylthiatricarbocyanine iodide; (iii) rhodamine B and derivatives or conjugates of rhodamine B; (iv) photodynamic therapy ("PDT") agents including hexylpyropheophorbide ("HPPH"); (v) a cyanine dye including Cy 5.5 dyes; and (vi) bifunctional contrast agents.

Indocyanine green ("ICG") is of particular interest since it has FDA approval for systemic administration. Indocyanine is excited at about 780 nm and emits at 830 nm. Indocyanine green will dissolve in blood and will bind to proteins such as albumin and lipoproteins. ICG is a nonspecific agent and is cleared rapidly from the blood. However, ICG tends to collect in regions of dense vascularity through extravascation. ICG may be administered to a patient at a dose of 0.2 mg/kg intravenously. Derivatives and conjugates of ICG may also be used.

Various embodiments are contemplated wherein ICG is excited using a 780 nm laser and fluorescent spectra at 830 nm are detected using a gain modulated image intensified charge coupled camera (ICCD).

Other embodiments are contemplated wherein magnetic nanoparticles ("MNPs") may be used as a contrast agent. The magnetic nanoparticles may comprise ferromagnetic iron oxide i.e. magnetite ($Fe_3O_4$) or maghemite ($\gamma$-$Fe_2O_3$) having a diameter in the range 1-100 nm. According to an embodiment the nanoparticles may have a diameter in the range 1-10, 10-20, 20-30, 30-40, 40-50, 50-60, 60-70, 70-80, 80-90 or 90-100 nm. In particular, various embodiments are contemplated wherein nanoparticles having a core diameter in the range of 5-15 nm may be used as contrast agents. In particular, as the size of the nanoparticles is reduced then the characteristics of the nanoparticles changes from having multi-domain ferromagnetic characteristics to having single domain characteristics and finally to having superparamagnetic characteristics. In particular, small nanoparticles having a diameter in the range 5-15 nm exhibit superparamagnetic properties having no hysteresis losses and will generate heat as a result of relaxational losses, mainly Néel relaxation loss. The inherent ferromagnetic properties of magnetic nanoparticles provides contrast enhancement with magnetic resonance ("MR") imaging. For example, accumulation of magnetic nanoparticles in brain tumours appears as a hypointensity on T2-weighted imaging including gradient echo imaging.

Magnetic nanoparticles may also be functionalised to target cancer cells thereby enabling cancerous tissue to be identified by magnetic resonance imaging.

According to an embodiment ultrasmall superparamagnetic iron oxide nanoparticles ("USPIONPs") may be used.

In addition to using nanoparticles to accumulate within cancerous tissue, according to further embodiments the nanoparticles may be heated by applying a magnetic field and in particular an alternating magnetic field ("AMF") which produces heat via relaxational loss via the Brownian Néel relaxation process or by hysteresis loss. As a result, potentially cancerous tissue can be identified on the basis of having an elevated or hyperthermic temperature relative to surrounding normal healthy tissue. Accordingly, thermal detection techniques in conjunction with the heating of nanoparticles which have accumulated in cancerous tissue may be used to visualise, image or target potentially cancerous tissue.

Further embodiments are contemplated wherein nanoparticles which have accumulated in cancerous tissue may be heated up to temperatures>40° C. in order to selectively target and kill cancerous cells. For example, heating cancerous cells to a temperature around 45° C. can cause cancer cells to undergo apoptosis or necrosis. Furthermore, locally heating cancerous cells can increase the blood flow to the cancerous cells which can, for example, result in an improved delivery of chemotherapeutic agents to the cancerous cells. Also, cancer cells are more heat sensitive than normal tissue and so heat can be selectively applied to cancer cells in order to kill cancer cells without damaging surrounding normal or healthy tissue.

According to an embodiment the nanoparticles may comprise a polysiloxane matrix (Si) wherein chelating species such as diethylene triamine pentaacetic acid (DTPA) at the surface of the particles allows the complexation of metallic elements such as gadolinium (Gd), silicon (Si), calcium (Ca) and iron (Fe).

According to other embodiments the nanoparticles may be heated by radiofrequency capacitive heating wherein, for example, an alternating electrical current at 8 MHz may be applied and the temperature of tissues located between the electrodes increases. Magnetite cationic liposomes (MCLs) may be used and when injected into cancer cells the cancerous tissue may reach a temperature which is 2-3° C. above that of healthy tissue.

Other embodiments are contemplated wherein antibodies containing a ferromagnetic component may be used as a contrast agent.

The one or more contrast agents may be exogenous or endogenous to the target.

As is well known, fluorophores may be activated to an excited state by absorbing a photon and may then relax to a ground state in a non-radiative manner. Alternatively, the fluorophore may relax to the ground state in a radiative (fluorescence) manner. The fluorescence lifetime $\tau$ is equivalent to the mean time that a fluorophores remains in its activated state and the quantum efficiency is the proportion of relaxations which occur radiatively.

Other mechanisms are known wherein the excited state can undergo intersystem crossing to an intermediate excited state wherein the spin state of the electron is flipped and the relaxation of the intermediate excited state is forbidden until the electron spin is reversed. The lifetimes of the intermediate excited state may be of the order of microseconds to milliseconds and are termed phosphorescence.

Fluorescence radiative decay can be affected by pH, oxygenation, free ion concentrations, glucose and other analytes. Fluorescence can therefore provide an optical imaging ability which is not otherwise directly detectable.

According to an embodiment the fluorescence spectra of tissue may be analysed in order to determine the pH, oxygenation level or quantum efficiency of the tissue.

Other embodiments are contemplated wherein gamma ray imaging may be performed and optionally a technetium-99 sulfur colloid may be injected into the target tissue for analysis.

According to various embodiments gold nanoparticles ("Au NPs" or "GNPs") may be used as contrast agents. Gold nanoparticles may be formed by a laser ablation method wherein a gold target in water is subjected to pulsed laser irradiation. Colloidal gold can also be prepared by citrate reduction. Various other physical methods of producing gold nanoparticles are known including inert gas condensation, thermolysis of gold(I) complex, radiolysis of gold salts, photochemistry and sonochemistry. Chemical methods of producing gold nanoparticles are known including emulsification, reduction of gold ions in the presence of a disperant, seed-mediated growth, use of reverse micelles and phase transfer reactions. Gold nanoparticles may also be biosynthesised by certain types of fungi including *Fusarium oxysporum, Verticillium* sp. and *Colletotrichum* sp. Gold nanoparticles have also been synthesized within HEK-293, HeLa, SiHa and SKNSH cells.

Gold nanoparticles may be readily functionalised generally through thiol linkages to provide functionalised gold nanoparticles (fGNPs) The surface of gold nanoparticles may be functionalised with e.g. cyclodextrin as a drug pocket having hydrophobic cavities, antibodies as a targeting moiety and poly(ethleneglycol) (PEG) as an anti-fouling shell. Anti-cancer drugs may be encapsulated into the hydrophobic cavity of the cyclodextrin and the gold nanoparticles may therefore be used as a drug delivery system (DDS).

According to various embodiments gold nanoparticles and in particular functionalised gold nanoparticles as described above may be used as contrast agents.

Gold nanoparticles cause local heating when irradiated with light (800-1200 nm) and hence gold nanoparticles may be used in the photothermal destruction of tumours according to various embodiments.

Plasmonic gold nanoparticles may be used for cancer diagnosis and photothermal therapy. Surface plasmon resonance ("SPR") leads to strong electromagnetic fields on the surface of gold nanoparticles which enhances all radiative properties such as absorption and scattering. In particular, Raman scattering is enhanced. Additionally, strongly absorbed light may be quickly converted to heat via a series of nonradiative processes.

Gold nanoparticles can be optically tuned by shape and structure and for example gold nanorods having different optical properties to gold nanospheres can be produced. The aspect ratio can be precisely controlled by changing experimental parameters in a seed-mediation growth method.

Gold nanoshells (comprising a silica core around 100 nm with a thin shell of gold a few nanometers thick) and gold nanocages may also be produced. Gold nanospheres, nanorods, nanostars and nanoshells may be used as contrast agents according to various embodiments.

According to an embodiment gold nanoparticles may be used for cancer imaging. It is known that gold nanoparticles scatter strongly and the scattering properties depend upon the size, shape and structure of the nanoparticles. According to an embodiment gold nanoparticles having a diameter 30-100 nm may be used. Such nanoparticles scatter intensely and can be detected using a microscope under dark field illumination conditions.

The gold nanoparticles may be conjugated with, for example, anti-epidermal growth factor receptors (anti-EGFR) antibodies (or other antibodies) to recognise the EGFR proteins (or other proteins) of cancer cells and tissues. The regular or well organised scattering pattern of nanoparticles bound to cancer cells can be readily distinguished from the random distribution of nanoparticles around healthy cells and this difference in scattering pattern may be utilised according to various embodiments.

The nanoparticles may be excited by white light from a halogen lamp.

According to an embodiment, functionalised gold nanoparticles may be distributed across the surface of a target (such as biological in vivo or ex vivo tissue) and the gold nanoparticles may preferentially bind to cancerous cells. As a result, cancerous regions of tissue can be identified by illuminating the target and either analysing the scattering pattern or measuring the scattered intensity of light.

For example, gold nanoparticles may have a strong surface plasmon resonance ("SPR") around 540 nm on the cell monolayer with the result that the nanoparticles scatter strongly in the green to yellow range of the visible spectrum. Similarly, gold nanorods may be constructed which exhibit a strong surface plasmon resonance ("SPR") around 800 nm giving an intense red colour.

Accordingly, gold nanoparticles may be used as imaging, physical or chemical contrast agents according to various embodiments.

Surface plasmon resonance ("SPR") effects also enhance the Raman scattering of adjacent molecules because the Raman intensity is directly proportional to the square of the field intensity imposed on the molecules. This phenomenon is termed as surface enhanced Raman scattering ("SERS").

According to an embodiment gold nanoparticles may be utilised in order to enhance Raman scattering of adjacent molecules. The gold nanoparticles may be either symmetric or asymmetric. According to an embodiment the gold nanoparticles may be asymmetric (e.g. nanorods) since asymmetric nanoparticles provide a larger Raman enhancement due to the lightening rod effect.

One particular advantage of using gold nanoparticles and surface enhance Raman scattering is that this approach greatly enhances detection sensitivity and decreases signal acquisition time.

According to another embodiment a Raman tag may be used as a spectroscopic imaging probe. The Raman tag may comprise organic dye molecules with aromatic structures which have relatively high Raman cross sections. Its fluorescence is quenched when they are adsorbed on to metallic nanoparticles and thus Raman signals are able to be detected.

The Raman tags may be physically adsorbed or chemically conjugated with both Raman tag and cancer targeting ligands.

According to other embodiments levan nanoparticles may be utilised for targeted cancer imaging. Levan is a biocompatible carbohydrate polymer that consists of β-D-fructofuranose attached by β-(2,6) linkages and is used in biomedical applications. According to an embodiment Indocyanine green (ICG) may be encapsulated in levan nanoparticles by self-assembly and the levan-ICG nanoparticles may be used for cancer imaging.

Various embodiments are contemplated wherein a target which may comprise biological tissue may be subjected to Raman or laser imaging (transmission or fluorescence) using nanoparticles such as gold nanoparticles are described above as contrast agents. One or more regions of interest may then be identified and the regions of interest may then be subjected to analysis using a first device to generate aerosol, smoke or vapour. The first device may comprise an ambient ionisation ion source such as a rapid evaporative ionisation mass spectrometry ("REIMS") ion source.

Other embodiments are contemplated wherein chemical tags (such as luminescent tags) may be used in combination with an ambient ionisation ion source such as a rapid evaporative ionisation mass spectrometry ("REIMS") ion source. For example, according to an embodiment a luminescent imaging, physical or chemical contrast agent may be modified with the inclusion of a ligand that is readily ionisable by an ambient ionisation ion source such as a rapid evaporative ionisation mass spectrometry ("REIMS") ion source. The contrast agents, tags or nanoparticles may be detected by mass spectrometry if an undesired (or desired) target or undesired (or desired) tissue is ablated. The tagging chemical may have fluorescent, magnetic, chemical, physical or other imaging properties and a part of the molecule may be arranged so as to ionise well for mass spectrometry analysis. For example, as described above, Indocyanine green (ICG) may be encapsulated into levan nanoparticles or more generally in functionalised nanoshells which are functionalised so as to target cancerous tissue or other undesired target material. Embodiments are contemplated wherein ICG (or other chemicals) which may be encapsulated within functionalised nanoparticles or nanoshells (which may be functionalised so as to target cancerous tissue) may be detected by mass spectrometry. Other embodiments are contemplated wherein one or more different markers other than ICG may be encapsulated into nanoparticles which target cancerous tissue. These one or more markers may then identified by mass spectrometry and a determination may be made that the tissue which is currently being analysed comprises cancerous tissue or otherwise comprises undesired target material.

Embodiments are contemplated wherein target experiments may be performed wherein a target is subjected to mass spectrometry analysis with a view to seeking to identify portions of target or tissue which include (or conversely do not include) a contrast agent, chemical tag, marker or nanoparticle wherein the contrast agent, chemical tag, marker or nanoparticle has been functionalised so as to target a particular target e.g. cancerous tissue. According to various embodiment identifying the presence of the contrast agent, chemical tag, marker or nanoparticle thereby enables a determination to be made that the target or tissue which is currently being analysed comprises cancerous tissue (or otherwise desired or undesired target material).

According to an embodiment the step of using physical or other non-mass spectrometric data to determine one or more regions of interest may comprise the use of targeted nanoparticles containing or comprising a metal which is intended to change the electrical impedance of a targeted tissue type. As detailed above, metallic nanoparticles may be functionalised so that they adhere to specific types of tissue or other surfaces. One or more regions of interest of a target may be identified by determining one or more regions of a target (e.g., tissue) having a different impedance to other target areas due to the presence of targeted or functionalised nanoparticles which preferentially adhere to certain specific target areas (e.g., cancerous tissue).

Photothermal Therapy (PTT)

Gold nanoparticles absorb light much more strongly than organic dye molecules. Nearly 100% adsorbed light is converted to heat via nonradiative properties. Accordingly, gold nanoparticles may be used as photothermal contrast agents for photothermal therapy wherein photon energy is converted to heat sufficient to induce cellular damage via thermal effects such as hyperthermia, coagulation and evaporation.

Photothermal therapy may be performed using spherical gold nanoparticles in conjunction with either pulsed or continuous wave lasers.

Nanosecond pulsed lasers may be used in conjunction with PTT to provide highly selective and localised damage to cancer cells without affecting neighbouring healthy cells which may be only a few nanometers to tens of micrometers away.

For in vivo therapy of tumours under the skin or deeply seated tumours within tissue near infrared (NIR) light may be used because of its deep penetration ability due to minimal absorption by hemoglobin and water molecules.

According to an embodiment PEGylated gold nanoshells may used in conjunction with an ambient ionisation ion source since the absorption of gold nanoshells can be tuned to the NIR region. A continuous wave (cw) diode laser e.g. emitting at 820 nm with an irradiance of e.g. 35 W/cm$^2$ for 4 mins may be used to illuminate the gold nanoshells in order to cause cancer cell death of targeted cells.

The gold nanoshells may according to various embodiments be injected into the blood stream of a patient or spread upon the surface of a target or tissue sample.

Other embodiments are contemplated wherein PTT may be performed using gold nanorods. According to an embodiment a cw Ti:Saphhire laser emitting at 800 nm may be used in conjunction with gold nanorods.

According to an embodiment the target may be illuminated with either linearly polarized light or circularly polarized light. Illuminating gold nanorods with circularly polarized light is particularly beneficial as the light absorption by gold nanorods is enhanced leading to an ultra-low energy threshold for cancer killing.

It has been determined that a laser fluence of 30 J/cm$^2$ can result in an increase in temperature of the cells by about 10° C. which is sufficient to induce heat-stress cell death. Accordingly, a laser fluence of 30 J/cm$^2$ may be utilised according to various embodiments.

According to an embodiment gold nanorods may be conjugated to methoxy-poly (ethylene-glycol)-thiol having an average MW 5,000 (mPEG-SH-5000) and may be injected into a patient either intravenously and/or subcutaneously. Tumours or cancerous cells can be identified using transmission imaging of a NIR laser with a camera due to the NIR light absorption by the nanorods in the tumour.

Combination of Raman Spectroscopy with Rapid Evaporative Ionisation Mass Spectrometry ("REIMS") and Other Ambient Ionisation Techniques for the In Situ Identification of Tumours During Surgery According to an embodiment Raman spectroscopy may be combined with rapid evaporative ionization mass spectrometry ("REIMS") (or other ambient ionisation techniques) for the identification of tumours either during surgery or when analysing ex vivo tissue. Experimental data is presented below taken from the context of in vivo brain surgery. However, the approach of combining Raman spectroscopy with ambient ionisation techniques such as rapid evaporative ionization mass spectrometry ("REIMS") may be applied to other situations including other types of surgery and non-surgical applications.

Figure 15:
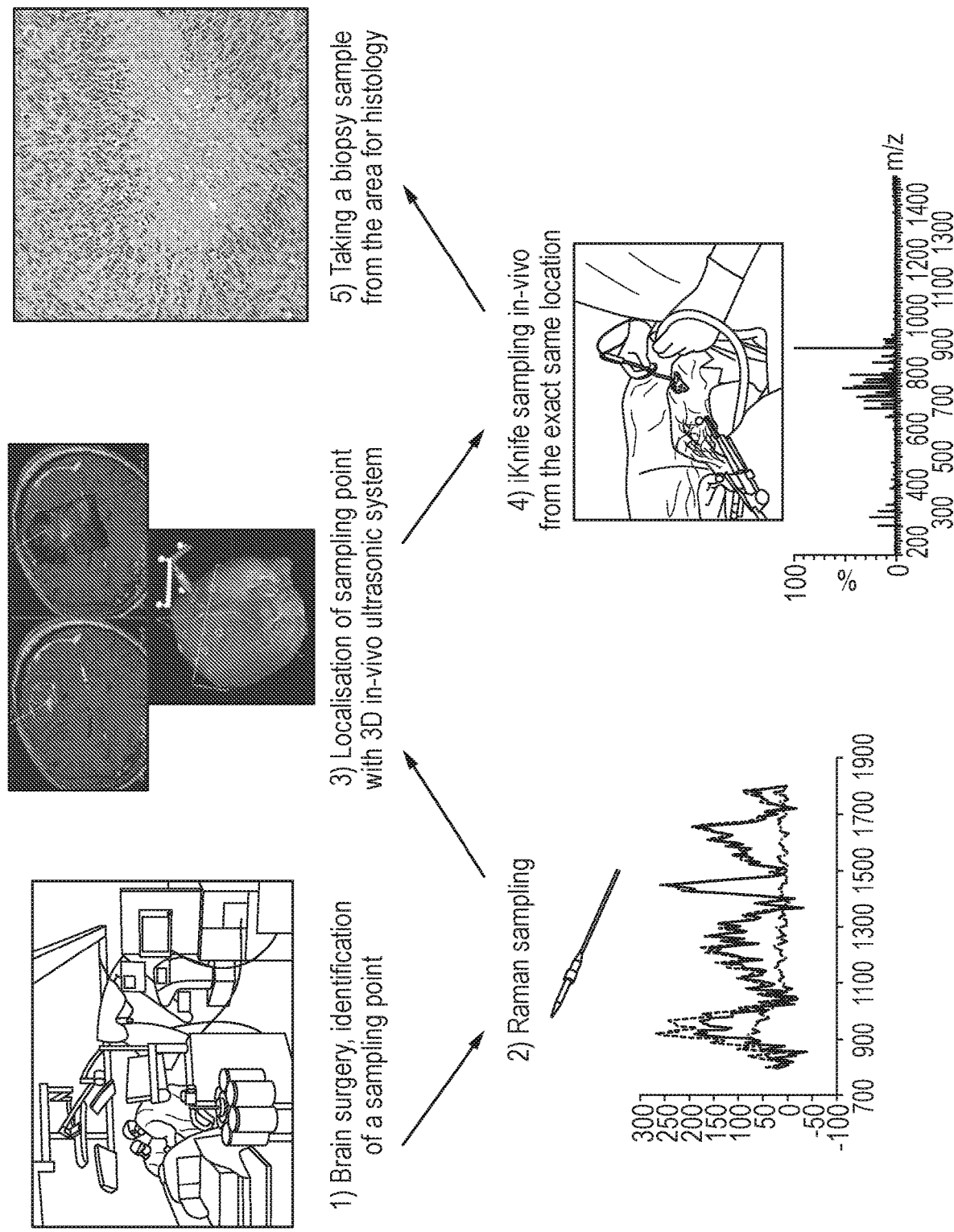
FIG. 15 shows illustrates an embodiment wherein various sampling points during brain surgery were subjected to Raman sampling and wherein the sampling points were then localised using a 3D in vivo ultrasonic system and rapid evaporative ionisation mass spectrometry ("REIMS") sampling was then performed at the same sampling points.

A sampling and validation method is summarized in FIG. 15. According to an embodiment one or more Raman sampling points may be identified. Raman sampling may then be performed at the sampling points. Localisation of the one or more Raman sampling points may then be performed using a 3D in vivo ultrasonic visualisation system.

Rapid evaporative ionisation mass spectrometry ("REIMS") sampling (or sampling using a different type of ambient ionisation ion source) may then be performed in vivo from exactly the same locations as the Raman sampling points. Furthermore, a biopsy sample may optionally be taken from the area for histological validation.

The target (e.g. surgical site) may first be sampled by Raman spectroscopy, followed by an ultrasonic reading and localization of the area. As a subsequent step rapid evaporative ionisation mass spectrometry ("REIMS") sampling (or another method of ambient ionisation) may then be performed using e.g. bipolar forceps or a laser ablation device. The rapid evaporative ionisation mass spectrometry ("REIMS") sampling (or other method of ambient ionisation) may then be followed by taking a core biopsy of the area for ex vivo analysis and histopathology.

According to an embodiment a number of different sampling points may be used during a surgical procedure. For example, according to an experiment which was performed and which is described in more detail below, 14 sampling points were used. However, it will be understood to those skilled in the art and a fewer or greater number of sampling points may be used.

A total of 24 patients were enrolled in one particular patient study involving rapid evaporative ionisation mass spectrometry ("REIMS") analysis of brain tumours during which additional Raman sampling was performed in nine cases.

FIG. 16 relates to a case study of one out of the 24 patients who were all suffering from different types of brain tumours. The particular patent who was the subject of the case study presented in FIG. 16 was patient #4 (IKBRA04) who had grade IV Glioblastoma multiforme ("GBM"). A full list of patients and their associated tumour type is given in the following table:

| Patient | Tumour type | WHO grade |
| --- | --- | --- |
| IKBRA01 | low grade oligodendroglioma | Grade II |
| IKBRA02 | low grade fibrillary astrocytoma | Grade II |
| IKBRA03 | Anaplastic astrocytoma | Grade III |
| IKBRA04 | Glioblastoma multiforme | Grade IV |
| IKBRA05 | Glioblastoma multiforme | Grade IV |
| IKBRA06 | Diffuse astrocytoma | |
| IKBRA07 | Anaplastic astrocytoma | Grade III |
| IKBRA08 | Meningioma | Grade I |
| IKBRA09 | Cystic gliosarcoma | |
| IKBRA10 | Anaplastic oligodendroglioma | Grade III |
| IKBRA11 | Glioblastoma multiforme | Grade IV |
| IKBRA12 | Glioblastoma multiforme | Grade IV |
| IKBRA13 | Fibrillary and gemistocytic astrocytoma | Grade II |
| IKBRA14 | Diffuse astrocytoma | Grade II |
| IKBRA15 | Ependymoma, cellular type | Grade II |
| IKBRA16 | Glioblastoma multiforme | Grade IV |
| IKBRA17 | Glioblastoma multiforme | Grade IV |
| IKBRA18 | Oligodendroglioma | Grade II |
| IKBRA19 | Giant Cell Glioblastoma | Grade IV |
| IKBRA20 | Anaplastic astrocytoma | Grade III |
| IKBRA21 | Low grade astrocytoma | Grade II |
| IKBRA22 | Low grade astrocytoma | Grade II |
| IKBRA23 | Recurrent glioblastoma | Grade IV |
| IKBRA24 | Anaplastic astrocytoma | Grade III |

The left-hand portion of FIG. 16 shows a 3D image of the brain of patient #4 which has been overlayed with a real time ultrasonic image. Six sampling points were taken using a rapid evaporative ionisation mass spectrometry ("REIMS") probe during surgery and are also depicted on the image shown in FIG. 16.

FIG. 16 also shows six corresponding mass spectra which were recorded wherein each mass spectrum corresponds to a different sampling point.

FIG. 16 also shows a 3D PCA plot of all sampling point taken during the surgery. The 3D PCA plot was labelled by a neuropathologist.

All in vivo and ex vivo sampling points are shown on the PCA plot shown in FIG. 16. It is apparent from FIG. 16 that normal grey and white matter group separately both from the cancerous samples and from each other.

Figure 17:
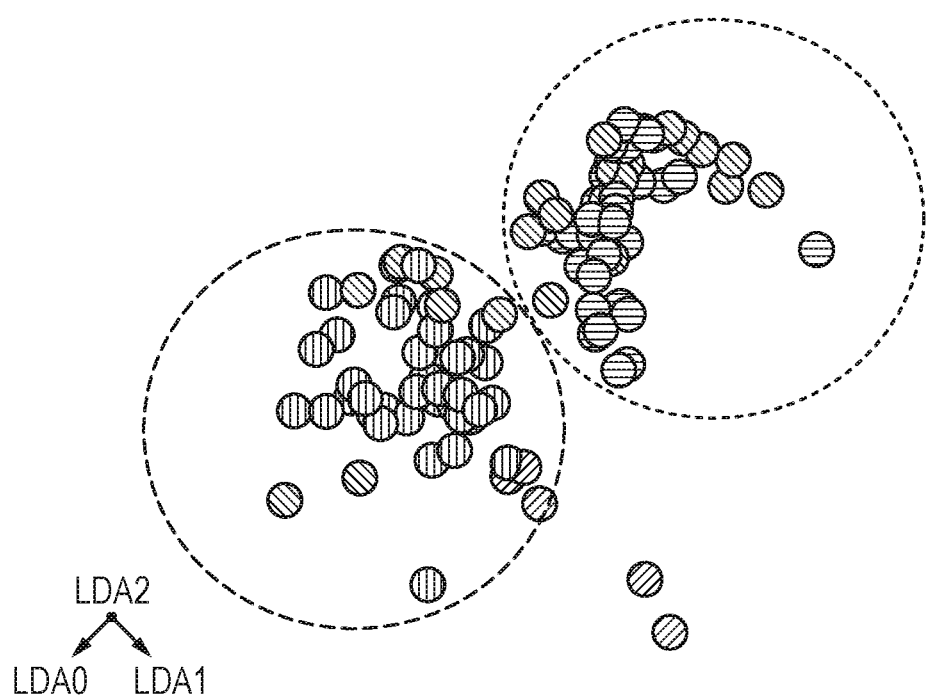
FIG. 17 shows a 3D pseudo LDA plot of ten patients who were suffering from four different tumour types and shows that high and low grade tumours separate well on the space although some grade III oligodendroglioma tumours group with low grade tumours.

Tumour Typing and Grading using a Rapid Evaporative Ionisation Mass Spectrometry ("REIMS") Probe FIG. 17 shows the result according to an embodiment of comparing patients with high grade (grade IV) Glioblastoma multiforme (e.g., Glioblastoma, giant cell Glioblastoma and recurrent Glioblastoma) and low grade (grade II and III) tumours (e.g. anaplastic astrocytoma, oligodendroglioma and diffuse astrocytoma).

It is apparent from FIG. 17 that high grade (grade IV) and low grade (grade II and III) tumours separated well on a 3D pseudo LDA plot.

Patients having intermediate grade III tumours grouped either with the high grade area of the space or with the low grade area of the space.

Embodiments are contemplated wherein the positioning of a sample in the 3D space may be used to predict the possible progression of an anaplastic astrocytoma in the future.

Comparison of Healthy and Cancerous Samples with Both Raman Spectroscopy and Rapid Evaporative Ionisation Mass Spectrometry ("REIMS") Sampling Patient #21 (IKBRA21) was suffering from a low grade (grade II) astrocytoma. The patient was subjected to a combination of Raman spectroscopy sampling and rapid evaporative ionisation mass spectrometry ("REIMS") sampling. Raman data from a total of 32 sampling points were recorded. 13 of these 32 sampling points corresponded with normal tissue, 18 of these 32 sampling points corresponded with cancerous tissue and 1 corresponded with background.

Rapid evaporative ionisation mass spectrometry ("REIMS") sampling was also performed at 14 of the 32 sampling points.

Figure 18:
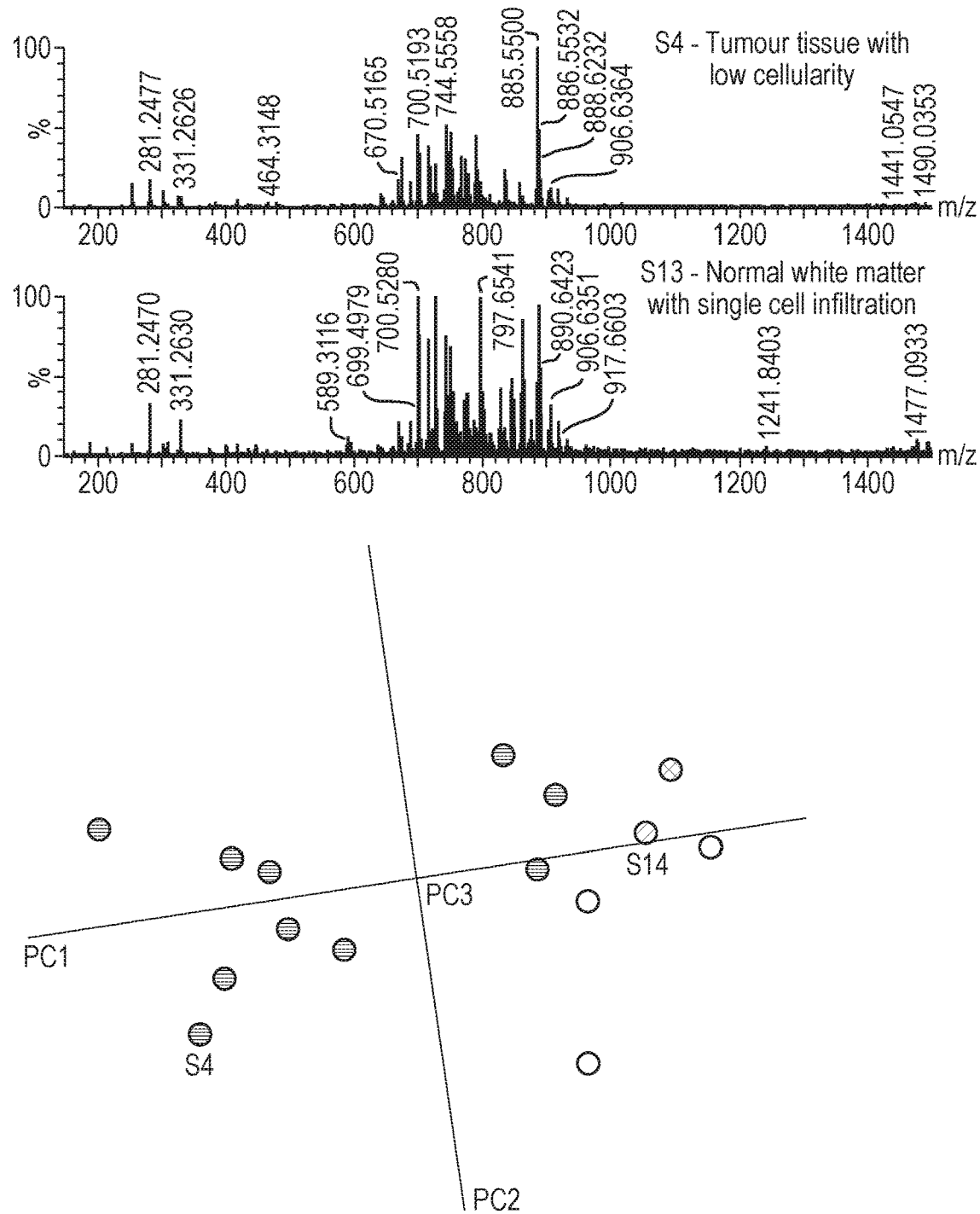
FIG. 18 shows (above) mass spectra obtained by rapid evaporative ionisation mass spectrometry ("REIMS") together with a 3D PCA plot (below) from two sampling points, one consisting mainly from tumour, the other mainly from normal white matter and wherein there is a visible difference in the phospholipid composition (a trend can be observed from right to left on the PCA plot showing the amount of infiltration within the normal brain cells)

FIG. 18 shows rapid evaporative ionisation mass spectrometry ("REIMS") mass spectra from two sampling points. Sampling point S4 corresponded with tumour tissue having a low cellularity. In particular, sampling point S4 corresponded with posterior medial superficial tumour. Fragments of the tumour tissue had low cellularity and some degree of reactive gliosis. Sampling point S14 corresponded with normal white matter have single cell infiltration. In particular, sampling point S14 corresponded with posterior base pot. Multiple fragments of white matter with reactive gliosis and single-cell tumour infiltration are present.

FIG. 18 also shows a 3D PCA plot corresponding to all sampling points taken throughout the surgery.

Figure 19:
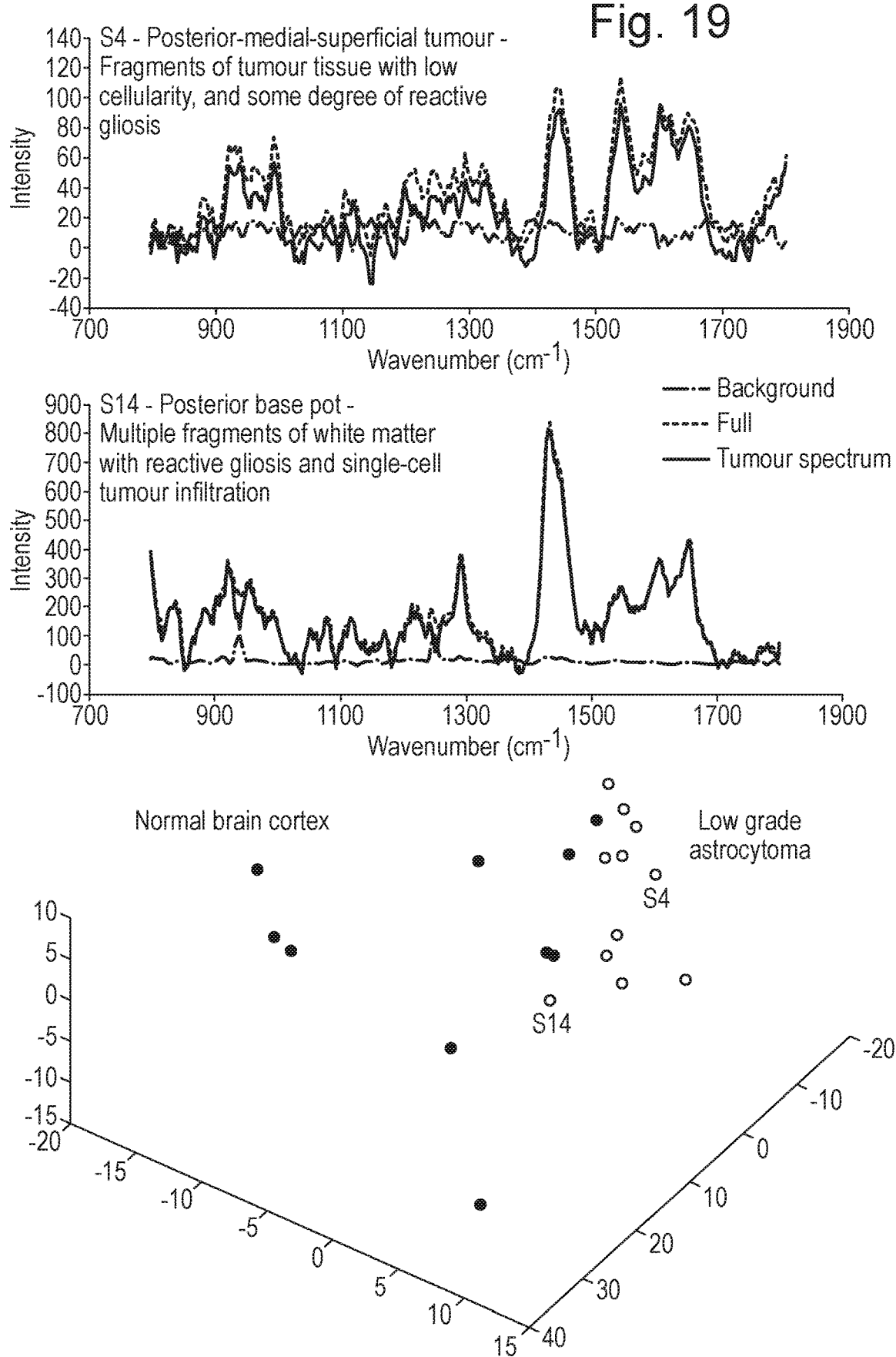
FIG. 19 shows Raman spectra (above) and a 3D PCA plot (below) from the same sampling points, one consisting mainly from the tumour, the other from normal white matter wherein the main differences observed on the PCA plot are due to the lipid vibration region.

FIG. 19 shows corresponding Raman spectra from sampling points S4 (tumour) and S14 (normal white matter) together with a 3D PCA plot from all sampling points taken throughout the surgery.

Both the Raman spectra and mass spectra obtained using an ambient ionisation ion source such as a rapid evaporative ionisation mass spectrometry ("REIMS") ion source have a tissue specific "fingerprint" in the phospholipid range. The main differences observed on the PCA plot are due to the lipid vibration region.

There are a number of sulfatides which are very specific for normal white matter of brain. For example, the following sulfatides are specific for normal white matter of the brain:

| m/z (calculated) | compound | formula |
|---|---|---|
| 888.624 | C24:1 sulfatide | $C_{48}H_{91}NO_{11}S$ |
| 906.635 | C24—OH sulfatide | $C_{48}H_{92}NO_{12}S$ |
| 916.655 | C26:1 sulfatide | $C_{50}H_{94}NO_{11}S$ |

The above described embodiments represent a novel protocol for intraoperative tissue identification and validation in surgical applications wherein both rapid evaporative ionisation mass spectrometry ("REIMS") technology and Raman spectroscopy are utilised. The various embodiments disclosed above show that both technologies are feasible for the distinction of healthy tissue and different brain cancers during an operation.

Raman spectroscopy, used as a non-invasive probe, is particularly suitable for providing initial information to a surgeon about where to start cutting, operating or resecting.

Rapid evaporative ionisation mass spectrometry ("REIMS") can provide more detailed and continuous information about the dissected tissue and may also be used to predict if a low grade tumour (e.g., grade II or III) has a high likelihood of progressing to a high grade tumour (e.g., grade IV) in the future or not.

The combination of Raman spectroscopy and rapid evaporative ionisation mass spectrometry ("REIMS") technologies enables molecular navigation in real-time and the combination of these two technologies enables important information to be provided to a surgeon in the assessment of tumour margins and tumour types (which can lead to an increase in the survival rate of patients).

Multivariate Analysis of Chemical Data

Various further embodiments are contemplated wherein the chemical data may itself be subjected to multivariate analysis in order to assist, for example, in the identification of the target and/or to filter out outliers.

Methods of Medical Treatment, Surgery and Diagnosis and Non-Medical Methods

Various different embodiments are contemplated. According to some embodiments the methods disclosed above may be performed on in vivo, ex vivo or in vitro tissue. The tissue may comprise human or non-human animal tissue. Embodiments are contemplated wherein the target may comprise biological tissue, a bacterial or fungal colony or more generally an organic target such as a plastic).

Various embodiments are contemplated wherein analyte ions generated by an ambient ionisation ion source are then subjected either to: (i) mass analysis by a mass analyser such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly (or vice versa) ion mobility analysis (IMS) and/or differential ion mobility analysis (DMA) and/or Field Asymmetric Ion Mobility Spectrometry (FAIMS) analysis followed by secondly (or vice versa) mass analysis by a mass analyser such as a quadrupole mass analyser or a Time of Flight mass analyser. Various embodiments also relate to an ion mobility spectrometer and/or mass analyser and a method of ion mobility spectrometry and/or method of mass analysis. Ion mobility analysis may be performed prior to mass to charge ratio analysis or vice versa.

Various references are made in the present application to mass analysis, mass analysers, mass analysing, mass spectrometric data, mass spectrometers and other related terms referring to apparatus and methods for determining the mass or mass to charge of analyte ions. It should be understood that it is equally contemplated that the present invention may extend to ion mobility analysis, ion mobility analysers, ion mobility analysing, ion mobility data, ion mobility spectrometers, ion mobility separators and other related terms referring to apparatus and methods for determining the ion mobility, differential ion mobility, collision cross section or interaction cross section of analyte ions. Furthermore, it should also be understood that embodiments are contemplated wherein analyte ions may be subjected to a combination of both ion mobility analysis and mass analysis i.e. that both (a) the ion mobility, differential ion mobility, collision cross section or interaction cross section of analyte ions together with (b) the mass to charge of analyte ions is determined. Accordingly, hybrid ion mobility-mass spectrometry (IMS-MS) and mass spectrometry-ion mobility (MS-IMS) embodiments are contemplated wherein both the ion mobility and mass to charge ratio of analyte ions generated e.g. by an ambient ionisation ion source are determined. Ion mobility analysis may be performed prior to mass to charge ratio analysis or vice versa. Furthermore, it should be understood that embodiments are contemplated wherein references to mass spectrometric data and databases comprising mass spectrometric data should also be understood as encompassing ion mobility data and differential ion mobility data etc. and databases comprising ion mobility data and differential ion mobility data etc. (either in isolation or in combination with mass spectrometric data).

Various surgical, therapeutic, medical treatment and diagnostic methods are contemplated.

However, other embodiments are contemplated which relate to non-surgical and non-therapeutic methods of mass spectrometry which are not performed on in vivo tissue. Other related embodiments are contemplated which are performed in an extracorporeal manner such that they are performed outside of the human or animal body.

Further embodiments are contemplated wherein the methods are performed on a non-living human or animal, for example, as part of an autopsy procedure.

Although the present invention has been described with reference to preferred embodiments, it will be understood by those skilled in the art that various changes in form and detail may be made without departing from the scope of the invention as set forth in the accompanying claims.

The invention claimed is:

1. A method comprising:
   directing light on to a target;
   obtaining or acquiring chemical or other non-mass spectrometric data from one or more regions of a target;
   wherein said target comprises native or unmodified target material which is unmodified by the addition of a matrix or reagent;
   using said chemical or other non-mass spectrometric data to determine one or more regions of interest of said target;
   using a first device to generate aerosol, smoke or vapour from the one or more regions of interest of said target, wherein said step of using said first device to generate aerosol, smoke or vapour from one or more regions of said target further comprises irradiating said target with a laser;
   causing said aerosol, smoke or vapour to impact upon a collision surface located within a vacuum chamber of a mass spectrometer and/or ion mobility separator so as to generate a plurality of analyte ions;
   mass analysing and/or ion mobility analysing said analyte ions derived in order to obtain mass spectrometric data and/or ion mobility data; and
   analysing a profile of said aerosol, smoke or vapour or a profile of ions derived from said aerosol, smoke or vapour.

2. The method as claimed in claim 1, wherein said light has a wavelength in a range selected from the group consisting of: (i) 400-450 nm; (ii) 450-500 nm; (iii) 500-500 nm; (iv) 500-550 nm; (v) 550-600 nm; (vi) 600-650 nm; (vii) 650-700 nm; (viii) 700-750 nm; and (ix) 750-800 nm.

3. The method as claimed in claim 1, wherein said chemical or other non-mass spectrometric data comprises Raman spectroscopy data.

4. The method as claimed in claim 1, wherein said profile is selected from the group consisting of: (i) a lipidomic profile; (ii) a fatty acid profile; (iii) a phospholipid profile; (iv) a phosphatidic acid (PA) profile; (v) a phosphatidylethanolamine (PE) profile; (vi) aphosphatidylglycerol (PG) profile; (vii) a phosphatidylserines (PS) profile; (viii) a phosphatidylinositol (PI) profile; or (ix) a triglyceride (TG) profile.

5. The method as claimed in claim 1, wherein said first device comprises or forms part of an ambient ion or ionisation source or wherein said first device generates said aerosol, smoke or vapour for subsequent ionisation by an ambient ion or ionisation source or other ionisation source.

6. The method as claimed in claim 1, wherein said first device is arranged and adapted to generate aerosol, smoke or vapour from one or more regions of said target without said target requiring prior preparation.

7. The method as claimed in claim 1, wherein the step of analysing said mass spectrometric data and/or ion mobility data comprises performing a supervised or unsupervised multivariate statistical analysis of said mass spectrometric data and/or ion mobility data.

8. The method as claimed in claim 7, wherein said multivariate statistical analysis is selected from the group consisting of: (i) principal component analysis ("PCA"); and (ii) linear discriminant analysis ("LDA").

9. The method as claimed in claim 1, further comprising determining a Raman spectrum or Raman profile of one or more regions of said target.

10. The method as claimed in claim 1, further comprising using said chemical or other non-mass spectrometric data to determine one or more regions of interest of said target by determining one or more regions of said target which have a different Raman spectrum, Raman profile or Raman spectral feature relative to normal tissue, surrounding tissue, a control sample, a control region, control data or predetermined data.

11. The method as claimed in claim 9, further comprising using said chemical or other non-mass spectrometric data to determine one or more regions of interest of said target by determining whether or not a region of said target has a higher or lower Raman peak intensity relative to normal tissue, surrounding tissue, a control sample, a control region, control data or predetermined data.

12. The method as claimed in claim 1, wherein said chemical or other non-mass spectrometric data comprises data selected from the group consisting of: (i) chemical composition data; (ii) fluorescence data; (iii) absorption data; (iv) reflectance data; (v) transmission data; (vi) elastic scattering data; (vii) Fourier Transform Infra-Red Spectroscopy (FTIR) data; and (viii) interferometry data.

* * * * *